(12) United States Patent
Scott et al.

(10) Patent No.: US 10,188,681 B2
(45) Date of Patent: *Jan. 29, 2019

(54) METHOD FOR INDUCING IMMUNE TOLERANCE USING NON-PROLIFERATIVE POLYMER-MODIFIED ALLOGENEIC LEUKOCYTES

(71) Applicant: CANADIAN BLOOD SERVICES, Ottawa (CA)

(72) Inventors: Mark D. Scott, Surrey (CA); Duncheng Wang, Greenville, NC (US); Wendy M. Toyofuku, Surrey (CA)

(73) Assignee: CANADIAN BLOOD SERVICES, Ottawa (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/414,396

(22) PCT Filed: Jul. 12, 2013

(86) PCT No.: PCT/CA2013/050547
§ 371 (c)(1),
(2) Date: Jan. 12, 2015

(87) PCT Pub. No.: WO2014/008612
PCT Pub. Date: Jan. 16, 2014

(65) Prior Publication Data
US 2015/0209387 A1    Jul. 30, 2015

Related U.S. Application Data

(60) Provisional application No. 61/670,694, filed on Jul. 12, 2012, provisional application No. 61/670,636, filed on Jul. 12, 2012.

(30) Foreign Application Priority Data

Jul. 12, 2012  (CA) ..................... 2782942

(51) Int. Cl.

| | |
|---|---|
| A01N 63/00 | (2006.01) |
| A61K 35/17 | (2015.01) |
| C12N 5/0783 | (2010.01) |
| A61K 39/00 | (2006.01) |
| C12N 15/113 | (2010.01) |
| A61K 9/00 | (2006.01) |
| A61K 35/14 | (2015.01) |
| A61K 47/69 | (2017.01) |
| A61K 35/00 | (2006.01) |
| A61K 35/12 | (2015.01) |
| A61K 47/60 | (2017.01) |

(52) U.S. Cl.
CPC ............ *A61K 35/17* (2013.01); *A61K 9/0019* (2013.01); *A61K 35/14* (2013.01); *A61K 39/001* (2013.01); *A61K 39/0008* (2013.01); *A61K 47/69* (2017.08); *A61K 47/6901* (2017.08); *C12N 5/0637* (2013.01); *C12N 5/0638* (2013.01); *C12N 15/113* (2013.01); *A61K 35/00* (2013.01); *A61K 47/60* (2017.08); *A61K 2035/122* (2013.01); *A61K 2035/124* (2013.01); *A61K 2039/515* (2013.01); *A61K 2039/577* (2013.01); *C12N 2310/141* (2013.01); *C12N 2500/50* (2013.01); *C12N 2501/00* (2013.01); *C12N 2501/65* (2013.01); *C12N 2502/1114* (2013.01)

(58) Field of Classification Search
None
See application file for complete search history.

(56) References Cited

U.S. PATENT DOCUMENTS

| | | | |
|---|---|---|---|
| 5,908,624 A | 6/1999 | Scott et al. | 424/93.7 |
| 8,007,784 B1 | 8/2011 | Scott et al. | 424/93.7 |
| 8,067,151 B2 | 11/2011 | Maurer et al. | 435/2 |
| 2003/0091541 A1 | 5/2003 | Ikehara et al. | 424/93.7 |
| 2005/0196386 A1 | 9/2005 | Blazar et al. | 424/93.7 |
| 2006/0062763 A1* | 3/2006 | Godfrey | C12N 5/0087 424/93.1 |
| 2007/0009497 A1 | 1/2007 | Steinman et al. | 424/93.21 |
| 2012/0093936 A1 | 4/2012 | Lindenberg et al. | 424/491 |
| 2014/0314866 A1 | 10/2014 | Brusko et al. | 424/501 |

FOREIGN PATENT DOCUMENTS

| | | |
|---|---|---|
| WO | WO 97/28254 | 8/1997 |
| WO | WO 02/072799 | 9/2002 |
| WO | WO 2007/120128 | 10/2007 |
| WO | WO 2009/106477 | 9/2009 |
| WO | WO 2011/053223 | 5/2011 |
| WO | WO 2012/065027 | 5/2012 |
| WO | WO 2014/008608 | 1/2014 |
| WO | WO 2015/003240 | 1/2015 |

OTHER PUBLICATIONS

Quinn et al., 2001, Best. Pract. Res. Clin. Rheum. vol. 15: 49-66.*
National Multiple Slcerosis Society, MS the disease, pp. 1-4.*
Progress in Autoimmune Disease Res. 2005, pp. 1-126.*
Scott et al., 1998, Current PHarm. Design, vol. 4: 423-438.*
Kaplan, Arth. Res. Ther. vol. 15: 219, pp. 1-9.*
Anderson MS, Bluestone JA. "The NOD mouse: a model of immune dysregulation." *Annu Rev Immunol.* 2005;23:447-85.
Bradley and Scott, "Immune complex binding by immunocamouflaged [poly(ethylene glycol)-grafted]erythrocytes", *Am J Hematol*, 82:970-975. 2007.

(Continued)

*Primary Examiner* — Amy E Juedes
(74) *Attorney, Agent, or Firm* — Norton Rose Fulbright US LLP

(57) ABSTRACT

This invention relates to cellular-based therapies for increasing the level of regulatory T cells (Treg) and/or decreasing the level of pro-inflammatory T cells (Th17) to induce anergy or immune tolerance. To provide these therapeutic effects, a non-proliferative allogeneic leukocyte population is contacted with another leukocyte population. The non-proliferative allogeneic leukocyte population is modified to bear on its surface a low-immunogenic biocompatible polymer so as to prevent pro-inflammatory allo-recognition with the latter leukocyte population. Cellular-based preparations and processes for achieving cellular therapy are also provided.

23 Claims, 23 Drawing Sheets

(56) References Cited

OTHER PUBLICATIONS

Bradley et al., "Interactions of IgM Abo antibodies and complement with methoxy-PEG-modified human RBCs", *Transfusion*, 41:1225-1233, 2001.

Chen and Scott, "Comparative Analysis of Polymer and Linker Chemistries on the Efficacy of Immunocamouflage of Murine Leukocytes", *Artif. Cells Blood Substit. Immobil. Biotechnol.*, 34:305-322, 2006.

Chen and Scott, "Current and future applications of immunological attenuation via pegylation of cells and tissue", *BioDrug*, 15:833-847, 2001.

Chen and Scott, "Immunocamouflage: Prevention of transfusion-induced graft-versus-host disease via polymer grafting of donor cells", *J. Biomed. Mater Res A.*, 67:626-636, 2003.

Le and Scott, "Immunocamouflage: The biophysical basis of immunoprotection by grafted methoxypoly(ethylene glycol) (mPEG)", *Acta Biomater*, 6:2631-2641, 2010.

McCoy and Scott, "Broad-Spectrum Antiviral Prophylaxis: Inhibition of Viral Infection by Polymer Grafting with Methoxypoly (ethylene glycol)", In: *Antiviral drug discovery for emerging diseases and bioterrorism threats.*, PF T, editor, Hoboken, NJ: Wiley & Sons; p. 379-395, 2005.

Murad et al., "Stealth Cells: Prevention of Major Histocompatibility Complex Class II-Mediated T-Cell Activation by Cell Surface Modification", *Blood*, 94:2135-2141, 1999.

Murad et al., "Structural and Functional consequences of Antigenic Modulation of Red Blood Cells With Methoxypoly(Ethylene Glycol)", *Blood*, 93:2121-2127, 1999.

O'Connell, RM et al. "MicroRNA-155 promotes autoimmune inflammation by enhancing inflammatory T cell development". *Immunity*. Oct. 29, 2010 (Oct. 29, 2010), vol. 33, pp. 607-619, ISSN : 1074-7613.

O'Neill and Bhardwaj, "Differentiation of Peripheral Blood Monocytes into Dendritic Cells", *Curr Protoc Immunol*, Chapter 22, Unit 22F.4.1-4.9, 2005.

Scott et al., "Chemical camouflage of antigenic determinants: Stealth erythrocytes", *Proc. Natl. Acad. Sci. USA*, 94:7566-7571, 1997.

Stahl, HF et al. "miR-155 inhibition Sensitizes CD4+ Th cells for TREG mediated suppression". *PLoS One*. Sep. 24, 2009 (Sep. 24, 2009), vol. 4, p. e7158, ISSN: 1932-6203.

Sutton and Scott, "The effect of grafted methoxypoly(ethylene glycol) chain length on the inhibition of respiratory syncytial virus (RSV) infection and proliferation", *Biomaterials*, 31:4223-4230, 2010.

Viegas, TX et al. "Polyoxazoline : chemistry, properties, and applications in drug delivery." *Bioconjugate Chemistry*. May 18, 2011 (May 18, 2011). vol. 22, pp. 976-986. ISSN : 1043-1802.

Wang D, Toyofuku WM, Chen AM, Scott MD. "Induction of immunotolerance via mPEG grafting to allogeneic leukocytes". *Biomaterials*. Dec. 2011; 32(35):9494-503.

Extended European Search Report issued in European Application No. 13816754.9, dated Mar. 4, 2016.

Wang et al., "Use of Flow Cytometry in the In Vitro and In Vivo Analysis of Tolerance/Anergy Induction by Immunocamouflage", In: "Flow Cytometry—Recent Perspectives", Jun. 13, 2012, InTech, XP055246158.

Getts et al., "Current landscape for T-cell targeting in autoimmunity and transplantation", *Immunotherapy*, 3(7): 853-870, 2011.

Dutheil D, Underhaug Gjerde A, Petit-Paris I, Mauco G, Holmsen H. "Polyethylene glycols interact with membrane glycerophospholipids: is this part of their mechanism for hypothermic graft protection?" *J Chem Biol*. Mar. 2009; 2(1):39-49.

Supplementary European Search Report issued in Application No. 13889025, dated Feb. 10, 2017.

Article 94(3) Communication issued in Application No. 13817560, dated Feb. 22, 2017.

Bradley et al. •"Separation and purification of methoxypoly(ethylene glycol) grafted red blood cells via two-phase partitioning" *J Chromatogr B Analyt Technol Biomed Ufe Sci.*, 807(1):163-8, 2004.

Burrell et al. "Regulatory T Cell Induction, Migration, and Function in Transplantation" *J Immunol*, 189:4705-4711,2012.

Dai et al., "MicroRNA, a new paradigm for understanding immunoregulation, inflammation, and autoimmune diseases," *Translational Research*, 157(4): 163-179, 2011.

Extended European Search Report issued in European Application No. 13817560.9, dated Mar. 11, 2016.

Extended European Search Report issued in European Application No. 13817292.9, dated Mar. 16, 2016.

Forman et al., *The Journal of Experimental Medicine* 138:672-685, 1973.

Hardy et al., *Nature* 223: 511-512, 1969.

Harris et al., "MicroRNAs as Immune Regulators: Implications for Transplantation," *American Journal of Transplantation*, 10(4): 713-719, 2010.

Miroux et al. "In Vitro Effects of Cyclosporine A and Tacrolimus on Regulatory T-Cell Proliferation and Function" *Transplantation*, 94(2): 123-31,2012.

Morita et al., *Proc. Natl. Acad. Sci.* USA 95:6947-6952, 1998.

Scott et al. "Beyond the red cell: pegylation of other blood cells and tissues" *Transfus Clin Biol.*, 11 (1):40-6, 2004.

Scott et al. "Stealth erythrocytes: effects of polymer grafting on biophysical, biological and immunological parameters" *Blood Transfusion*, 1: 244-65, 2003.

Spiegel et al., "Role of microRNAs in immunity and organ transplantation," *Expert Reviews in Molecular Medicine*, 13: e37, 2011.

Wang et al., "The potential utility of methoxypoly (ethylene glycol)-medicated prevention of rhesus blood group antigen RhD recognition in transfusion medicine" *Biomaterials*, 33(10): 3002-12,2012.

Yoshimura et al., *Transplantation* 49(1): 167-171, 1990.

Office Action issued in European Application No. 15818906.8, dated Nov. 7, 2017.

\* cited by examiner

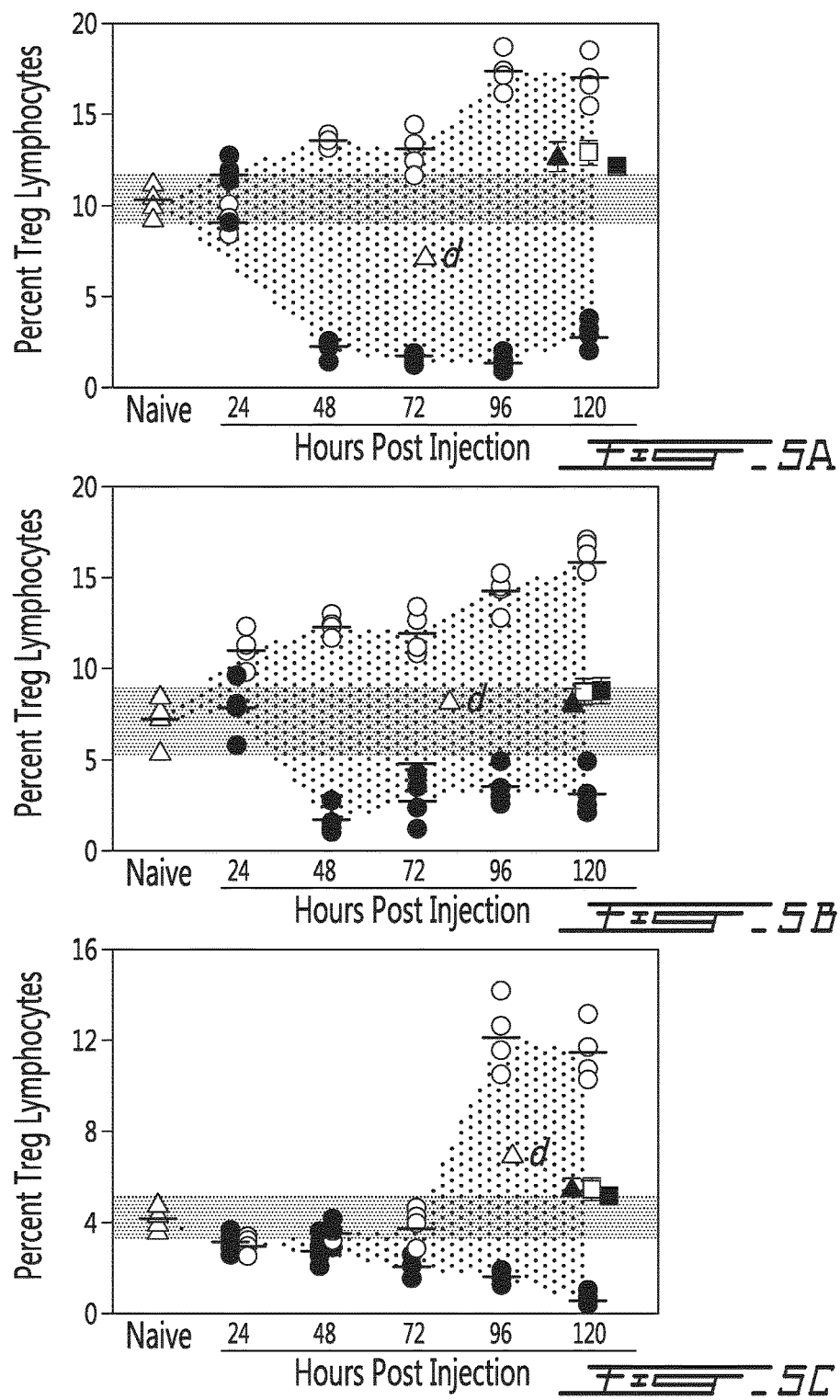

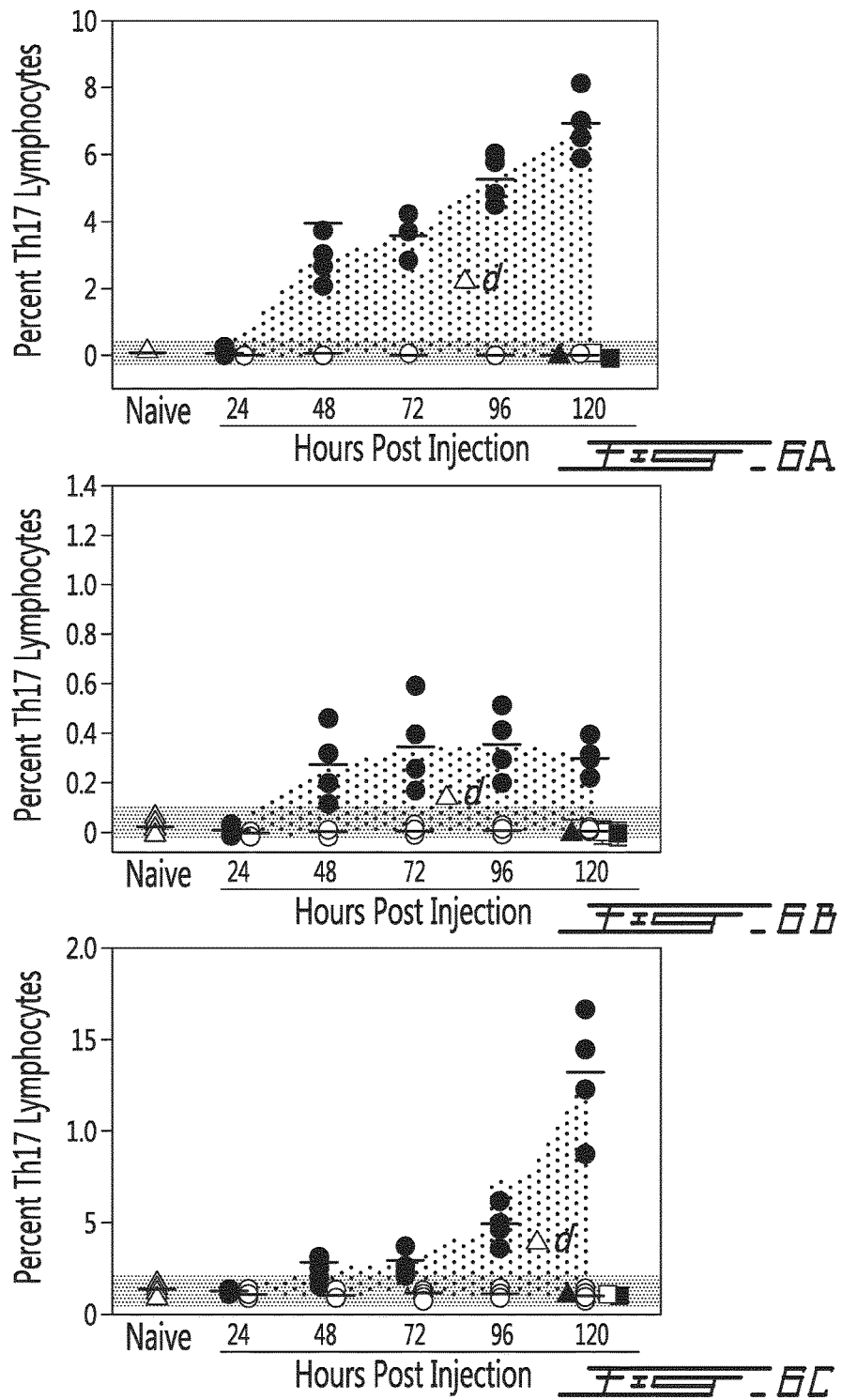

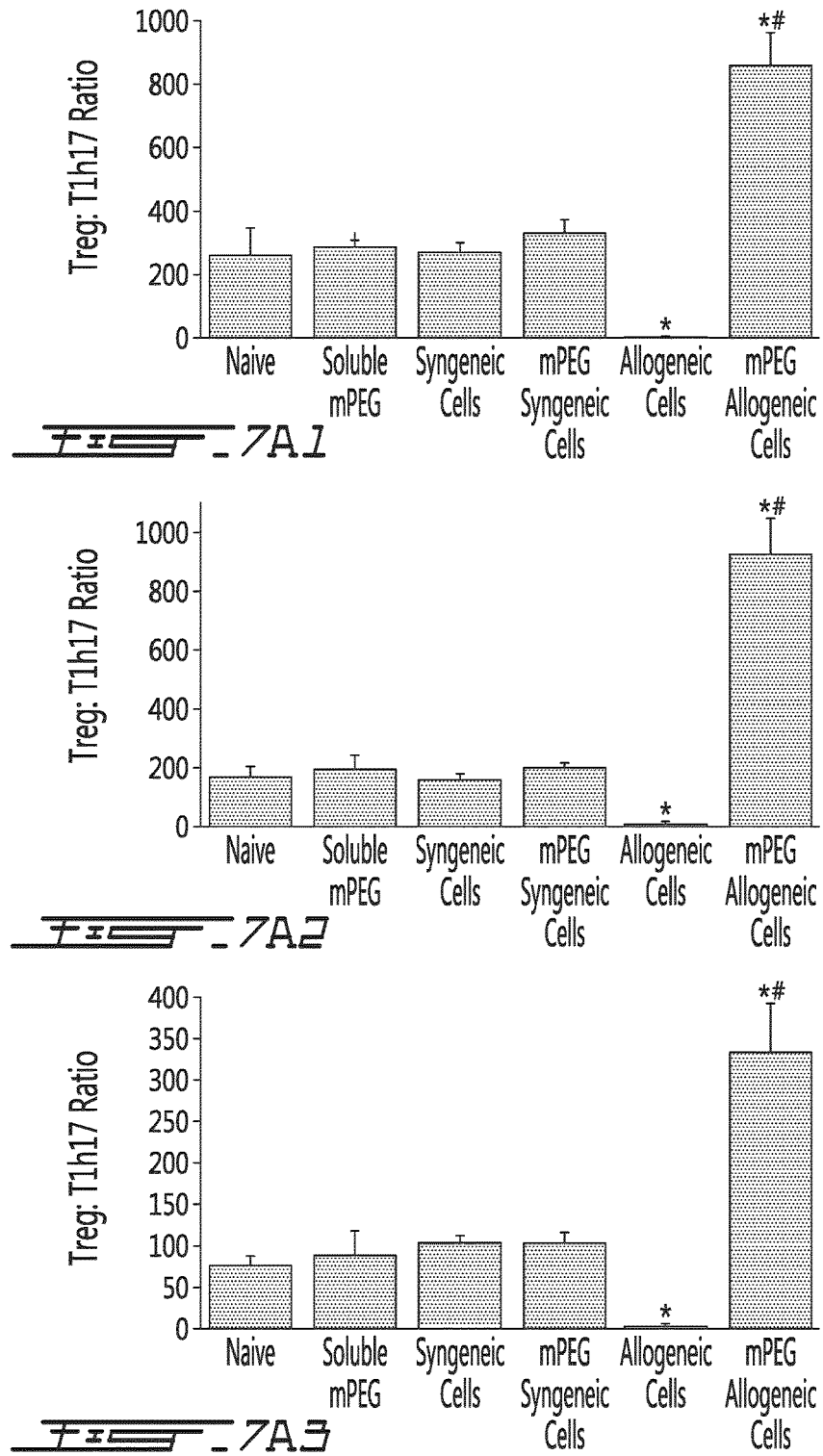

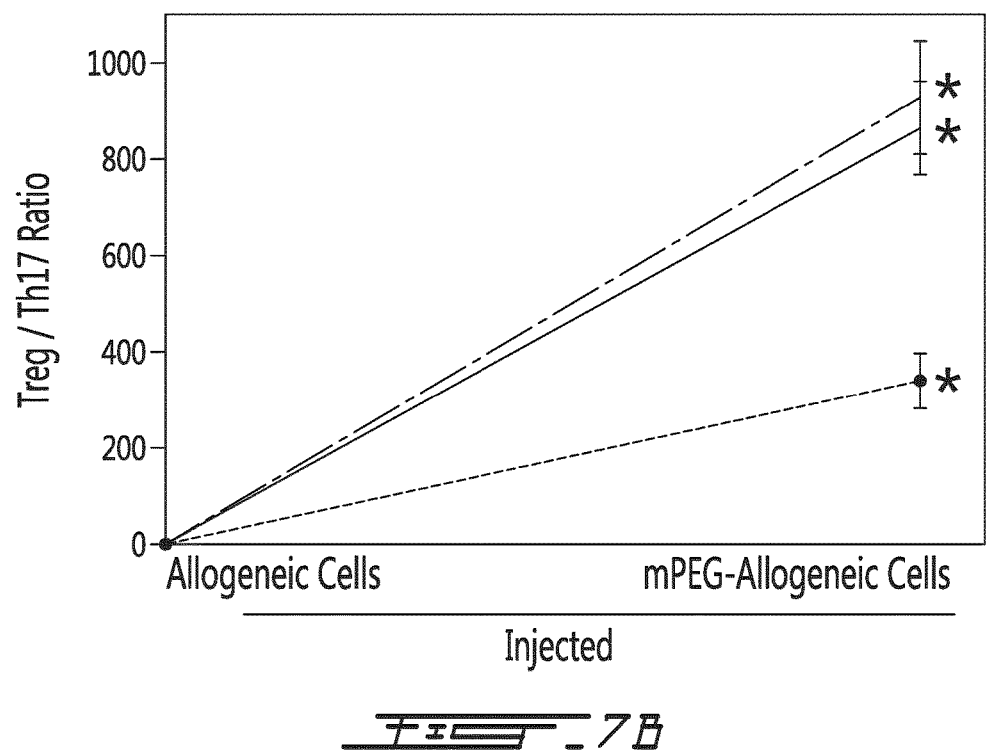

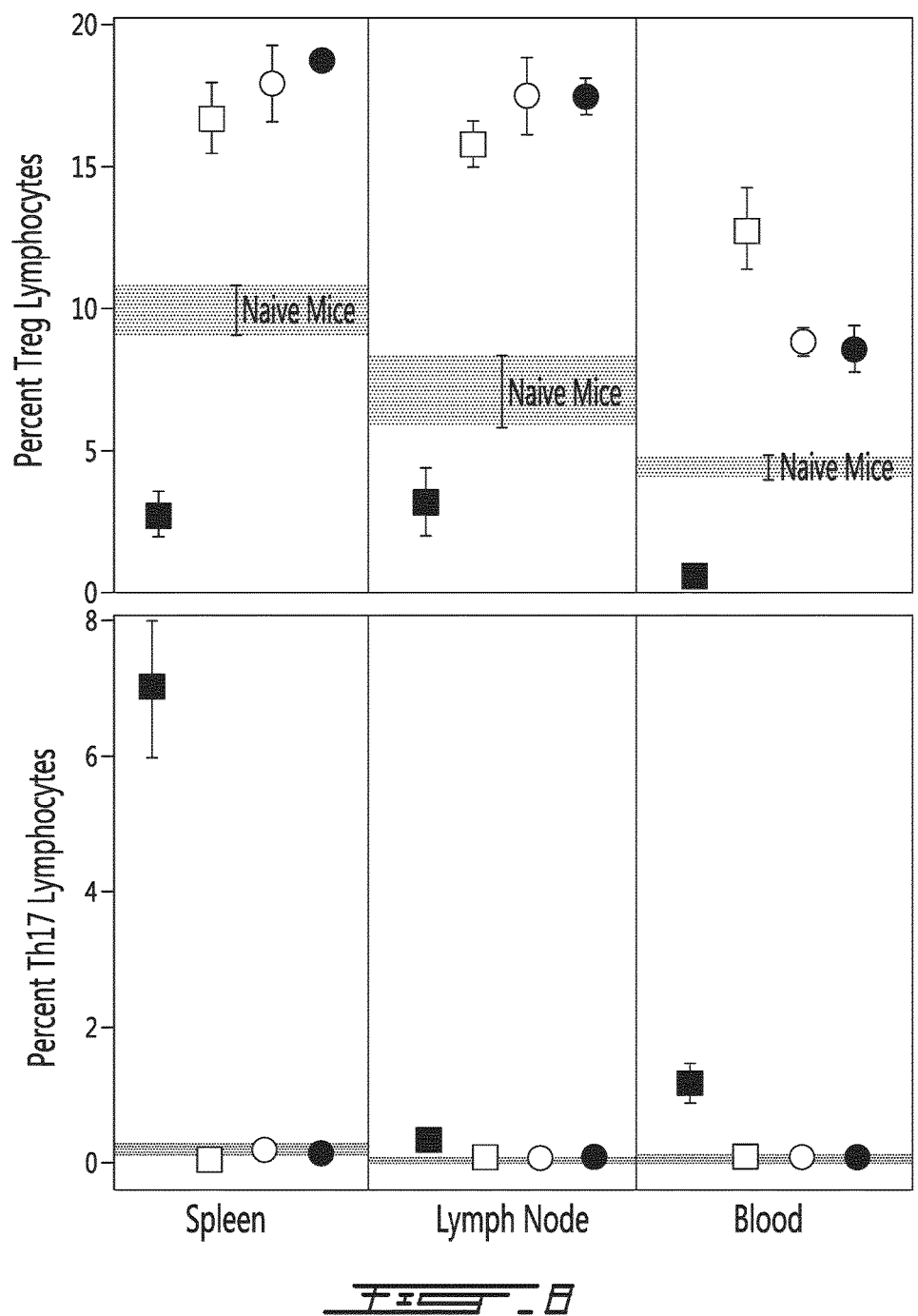

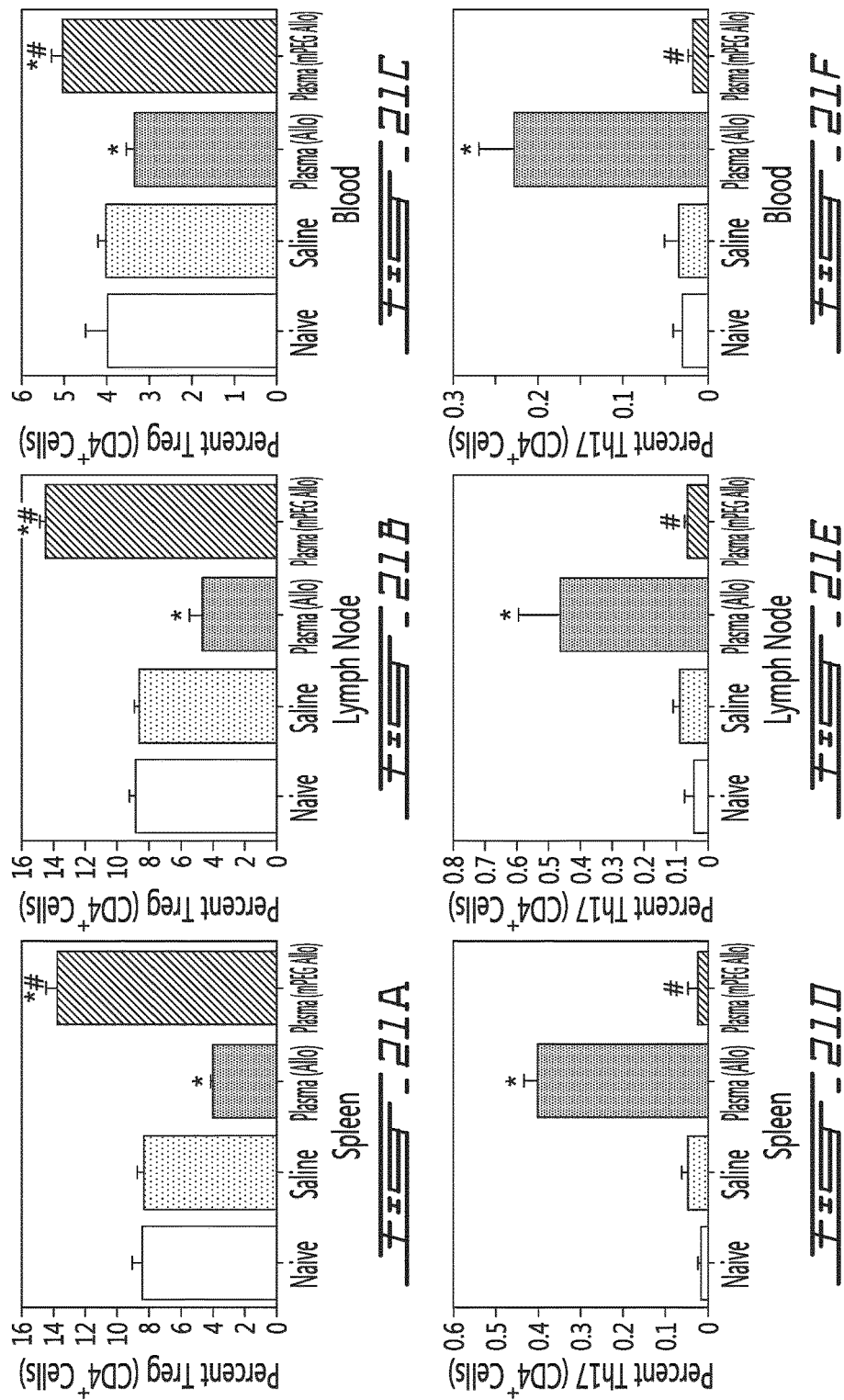

METHOD FOR INDUCING IMMUNE TOLERANCE USING NON-PROLIFERATIVE POLYMER-MODIFIED ALLOGENEIC LEUKOCYTES

CROSS-REFERENCE TO RELATED APPLICATIONS

This application is a national phase application under 35 U.S.C. § 371 of International Application No. PCT/CA2013/050547 filed Jul. 12, 2013, which claims priority from CA patent application 2782942, U.S. provisional patent application 61/670,636 and U.S. provisional patent application 61/670,694 all filed on Jul. 12, 2012. The entire contents of each of the above-referenced disclosures is specifically incorporated by reference herein without disclaimer.

TECHNOLOGICAL FIELD

This invention relates to the use of allogeneic non-proliferative leukocytes covalently modified with a biocompatible polymer to augment the level of regulatory T (Treg) cells and/or decrease the level of pro-inflammatory T cells for inducing of a state of immune tolerance or anergy in the treated subjects. These modified leukocytes are useful for the treatment of various conditions associated with excessive immune responses, auto-immunity and/or inflammation.

BACKGROUND

Acute and chronic rejection of donor tissues and organs remains a significant clinical problem in transplantation medicine. Moreover, autoimmune diseases in which one's own immune system recognizes "self" tissues as foreign can also be rejected by similar mechanisms. To minimize or prevent rejection, the administration of immunosuppressive agents is typically required. Acute and chronic rejection are primarily T lymphocyte-mediated events that require allogeneic recognition of the foreign tissue and the subsequent proliferation of allo-responsive T cells. Indeed, because of the central role of the T cell in rejection, it is the primary target of current immunosuppressive drugs (e.g., cyclosporine A, FK506). In general, these pharmacologic agents target either the T cell activation (e.g., cyclosporine A that inhibits IL-2 responsiveness) or the proliferation (e.g., methotrexate) of the allo-responsive T cells. However all of today's clinically approved anti-rejection drugs are beset by chronic toxicity; consequently, significant research is underway to identify alternative means of preventing acute and chronic rejection.

A biomaterials approach to the prevention of allo-recognition is the polymer modification of donor cells (e.g., erythrocytes, lymphocytes, and pancreatic islets) (Scott et al., 1997; Murad et al., 1999A; Murad et al., 1999B; Bradley et al., 2001; Chen et al., 2001; Chen et al., 2003; McCoy et al., 2005; Chen et al., 2006; Bradley et al., 2007; Sutton et al., 2010; Le et al., 2010). The modification of the surface of cells is made by the direct grafting of low immunogenicity polymers to the cell membrane. Previous studies have demonstrated that the polymer modification of erythrocytes and lymphocytes resulted in the loss of allo-recognition both in vitro and in vivo. Moreover, in contrast to pharmacologic agents, the grafted polymer exhibited both extremely low toxicity and immunogenicity.

It would be highly desirable to be provided with a cellular-based preparation capable of inducing a state of anergy or immunotolerance by increasing the ratio of the level of regulatory T cells (such as Treg) to pro-inflammatory T cells (such as Th1 and Th17). The cellular preparation could induce anergy or tolerance either by increasing Treg levels, decrease pro-inflammatory T cell levels or both. This preparation could be useful for treating, preventing and/or alleviating the symptoms associated to an abnormal/excessive immune condition, such as an auto-immune disease, a response to a vaccine or a tissue/cell transplantation.

BRIEF SUMMARY

One aim of the present invention is to provide cellular-based preparations capable of inducing a state of anergy or immunotolerance by increasing the ratio of the level of regulatory T cells (such as Treg) to the level of pro-inflammatory T cells (such as Th1 and Th17). The cellular-based preparations can induce anergy or tolerance either by increasing Treg levels, decrease pro-inflammatory T cell levels or both. These preparations are useful for treating, preventing and/or alleviating the symptoms associated to an abnormal/excessive immune condition, such as an auto-immune disease, a response to a vaccine or a tissue/cell transplantation. The cellular-based preparations and therapies presented herewith concern the use of at least two distinct leukocyte populations which are considered allogeneic with respect to one another, wherein at least one of the leukocyte population is non-proliferative and modified to bear on its surface a low-immunogenic biocompatible polymer so as to prevent pro-inflammatory allo-recognition between the two leukocyte populations. The two leukocyte populations can be contacted in vitro, ex vivo or in vivo to induce anergy or tolerance.

In accordance with the present invention, there is provided a method of increasing a ratio of the level of regulatory T (Treg) cells to the level of pro-inflammatory T cells in a subject in need thereof. Broadly, the method comprises administering: (i) a cellular preparation comprising a first leukocyte having a cytoplasmic membrane associated to a low-immunogenic biocompatible polymer (wherein the first leukocyte is allogeneic to the subject as well as being non-proliferative); (ii) a cultured cellular preparation comprising a leukocyte from the subject which has been obtained by culturing the leukocyte from the subject with the first leukocyte and/or (iii) a supernatant of a cell culture of a second leukocyte having a cytoplasmic membrane associated to the low-immunogenic biocompatible polymer and a third leukocyte (wherein the second leukocyte is allogeneic to the third leukocyte and at least one of the second or the third leukocyte is non-proliferative). The method is to provide an increase in the ratio of the level of Treg cells to the level of pro-inflammatory T cells in the treated subject. In an embodiment, the leukocyte is irradiated to prevent it from proliferating. In an embodiment, the cytoplasmic membrane of the first leukocyte and/or the second leukocyte has a membrane-associated protein covalently bound to the low-immunogenic biocompatible polymer. In an embodiment, the leukocyte from the subject and/or the third leukocyte has a cytoplasmic membrane associated to a low-immunogenic biocompatible polymer. In such embodiment, it is also contemplated that the cytoplasmic membrane of the leukocyte from the subject and/or of the third leukocyte has a membrane-associated protein covalently bound to the low-immunogenic biocompatible polymer. In yet another embodiment, the leukocyte described herein is a T cell (such as, for example, a CD4-positive or a CD8-positive T cell). In another embodiment, in the cultured cellular preparation, the leukocyte from the subject is expanded in vitro (or ex vivo) prior to administration to the subject. In yet another embodiment, in the cultured cellular preparation, the first leukocyte is removed prior to the administration to the subject. In an embodiment of the cell culture supernatant, the second leukocyte or the third leukocyte is from the subject. In yet another embodiment, the low-immunogenic biocompatible polymer is a polyethylene glycol (such as for example mPEG) and/or 2-alkyloxazoline (POZ). In still another embodiment, the increased ratio between the level of Treg cells and the level of pro-inflammatory T cells is for treating, preventing and/or alleviating the symptoms associated to an auto-immune disease afflicting the subject (such as, for example, type I diabetes, rheumatoid arthritis, multiple sclerosis, psoriasis, lupus, immune thrombocytopenia, experimental autoimmune encephalomyelitis, autoimmune uveitis, inflammatory bowel disease, scleroderma and/or Crohn's disease). In still another embodiment, the increased ratio between the level of Treg cells and the level of pro-inflammatory T cells is for preventing the onset of an excessive immune reaction in the subject (such as, for example, an excessive immune reaction in response to the administration of a vaccine). In a further embodiment, the increased ratio between the level of Treg cells and the level of pro-inflammatory T cells is for preventing or limiting the rejection of transplanted cells or tissue of the subject. In another embodiment, the transplanted cells and/or tissue are allogeneic or xenogeneic to the subject.

In accordance with the present invention, there is provided a cellular-based preparation for increasing a ratio of regulatory T (Treg) cells to pro-inflammatory T cells in a subject. The cellular-based preparation comprises (i) a cellular preparation comprising a first leukocyte having a cytoplasmic membrane associated to a low-immunogenic biocompatible polymer (wherein the first leukocyte is allogeneic to the subject and is considered non-proliferative); (ii) a cultured cellular preparation comprising a leukocyte from the subject which has been obtained by culturing it with the first leukocyte and/or (iii) a supernatant of a cell culture of a second leukocyte having a cytoplasmic membrane associated to the low-immunogenic biocompatible polymer and a third leukocyte (wherein the second leukocyte is allogeneic to the third leukocyte and at least one of the second or the third leukocyte is non-proliferative). The cellular-based preparation can be admixed with an appropriate excipient prior to administration to the subject. Embodiments with respect to the type of non-proliferative cells, the low-immunogenic biocompatible polymer, the first leukocyte, the leukocyte from the subject, the second leukocyte, the third leukocyte as well as the various uses of the preparations have been described above and do apply herein.

In accordance with the present invention, there is provided the use of the cellular-based preparations described herein for increasing a ratio of regulatory T (Treg) cells to pro-inflammatory T cells in a subject. There is also provided the use of the cellular-based preparations described herein for the preparation of a medicament for increasing a ratio of regulatory T (Treg) cells to pro-inflammatory T cells in a subject. The cellular-based preparation comprises (i) a cellular preparation comprising a first leukocyte having a cytoplasmic membrane associated to a low-immunogenic biocompatible polymer (wherein the first leukocyte is allogeneic to the subject and is modified so as to prevent its proliferation); (ii) a cultured cellular preparation comprising a leukocyte from the subject which has been obtained by culturing it with the first leukocyte and/or (iii) a supernatant of a cell culture of a second leukocyte having a cytoplasmic membrane associated to the low-immunogenic biocompatible polymer and a third leukocyte (wherein the second leukocyte is allogeneic to the third leukocyte and at least one of the second or the third leukocyte is non-proliferative). The cellular-based preparation can be admixed with an appropriate excipient prior to administration to the subject. Embodiments with respect to the type of non-proliferative cells, the low-immunogenic biocompatible polymer, the first leukocyte, the leukocyte from the subject, the second leukocyte, the third leukocyte as well as the various uses of the preparations have been described above and do apply herein.

In accordance with the present invention, there is provided a process for increasing and/or for providing the ability of a cellular-based preparation to increase a ratio of Regulatory T (Treg) cells to pro-inflammatory T cells in a subject. Broadly the process comprises (i) associating a low-immunogenic biocompatible polymer to a cytoplasmic membrane of a first leukocyte and refraining the first leukocyte from proliferating to obtain a first modified leukocyte (wherein the first leukocyte is allogeneic to the subject), (ii) culturing the first modified leukocyte with a leukocyte from the subject to obtain a cultured cellular preparation and/or (iii) associating the low-immunogenic biocompatible polymer to a cytoplasmic membrane of a second leukocyte to obtain a second modified leukocyte, culturing the second modified leukocyte with a third leukocyte (wherein the second leukocyte is allogeneic to the third leukocyte and at least one of the second or third leukocyte is non-proliferative), isolating the cell culture supernatant to obtain a cell culture supernatant; and (iv) formulating the first modified non-proliferative leukocyte, the cultured cellular preparation or the cell culture supernatant for administration to the subject (such as, for example, intravenous administration). The formulating step can also encompass formulating the first modified non-proliferative leukocyte, the cultured cellular preparation or the cell culture supernatant in a vaccine. Embodiments with respect to type of non-proliferative cells, the low-immunogenic biocompatible polymer, the first leukocyte, the leukocyte from the subject, the second leukocyte, the third leukocyte as well as the various uses of the preparations have been described above and do apply herein.

Throughout this text, various terms are used according to their plain definition in the art. However, for purposes of clarity, some specific terms are defined below.

Allogeneic cell. A cell is considered "allogeneic" with respect to another cell if both cells are derived from the same animal species but presents sequence variation in at least one genetic locus. A cell is considered "allogeneic" with respect to a subject if the cell is derived from the same animal species as the subject but presents sequence variation in at least one genetic locus when compared to the subject's respective genetic locus. Allogeneic cells induce an immune reaction (such as a rejection) when they are introduced into an immunocompetent host. In an embodiment, a first cell is considered allogeneic with respect to a second cell if the first cell is HLA-disparate (or HLA-mismatched) with the second cell.

Allo-recognition. As it is known in the art, the term "allo-recognition" (also spelled allorecognition) refers to an immune response to foreign antigens (also referred to as alloantigens) from members of the same species and is caused by the difference between products of highly polymorphic genes. Among the most highly polymorphic genes are those encoding the MHC complex which are most highly expressed on leukocytes though other polymorphic proteins may similarly result in immune recognition. These polymorphic products are typically recognized by T cells and other mononuclear leukocytes. In the context of the present invention, the term "pro-inflammatory allo-recognition" refers to an immune response associated with the expansion of pro-inflammatory T cells and/or the differentiation of naïve T cells into pro-inflammatory T cells. Pro-inflammatory allo-recognition in vivo mediates cell or tissue injury and/or death and loss of cell or tissue function. Still in the context of the present invention, the term "pro-tolerogenic allo-recognition" refers to an immune response associated with the expansion of Treg cells and/or the differentiation of naïve T cells into Treg cells. A pro-tolerogenic allo-recognition is usually considered weaker than a pro-inflammatory allo-recognition. Further, an in vivo pro-tolerogenic allo-recognition does not lead to significant cell or tissue injury and/or death nor loss of cell or tissue function.

Anergy and Tolerance. In the present context, the term "anergy" refers to a non-specific state of immune unresponsiveness to an antigen to which the host was previously sensitized to or unsensitized to. It can be characterized by a decrease or even an absence of lymphokine secretion by viable T cells when the T cell receptor is engaged by an antigen. In the present context, the term "tolerance" refers to an acquired specific failure of the immunological mechanism to respond to a given antigen, induced by exposure to the antigen. Tolerance refers to a specific non-reactivity of the immune system to a particular antigen, which is capable, under other conditions, of inducing an immune response. However, in the present context, the terms "anergy" and "tolerance" are used interchangeably since the compositions and methods presented herewith can be used to achieve both anergy and tolerance.

Autologous cell. A cell is considered "autologous" with respect to another cell if both cells are derived from the same individual or from genetically identical twins. A cell is considered "autologous" to a subject, if the cell is derived from the subject or a genetically identical twin. Autologous cells do not induce an immune reaction (such as a rejection) when they are introduced into an immuno-competent host.

Immunogenic cell. A first cell is considered immunogenic with respect to a second cell when it is able to induce an immune response in the latter cell. In some embodiment, the immune response is in vitro (e.g. a mixed lymphocyte reaction) or can be observed in vivo (e.g. in a subject having the second cell and having received the first cell). The second cell can be located in an immunocompetent subject. Preferably, the immune response is a cell-based immune response in which cellular mediator can be produced. In the context of this invention, the immunogenic cells are immune cells, such as white blood cells or leukocytes.

Immunogenic cell culture conditions. A cell culture is considered to be conducted in immunogenic conditions when it allows the establishment of a pro-inflammatory immune response between two distinct and unmodified leukocytes (and, in an embodiment, allo-recognition). Preferably, the pro-inflammatory immune response is a cell-based immune response in which cellular mediator can be produced. For example, the cell culture conditions can be those of a mixed lymphocyte reaction (primary or secondary). When a cell culture is conducted in immunogenic conditions but with leukocytes which have been modified to prevent or limit pro-inflammatory allo-recognition, no pro-inflammatory immune response is observed. However, when a cell culture is conducted in immunogenic conditions but with leukocytes which have been modified to prevent allo-recognition, a non-inflammatory immune response can be observed (for example a differentiation of naïve T cells to Treg cells and/or expansion of Treg cells).

Leukocyte. As used herein, a leukocyte (also spelled leucocyte) is defined as a blood cell lacking hemoglobin and having a nucleus. Leukocytes are produced and derived from hematopoietic stem cells. Leukocytes are also referred to as white blood cells. Leukocytes include granulocytes (also known as polymorphonuclear leukocytes), e.g. neutrophils, basophils and eosoniphils. Leukocytes also include agranulocytes (or mononuclear leucocytes), e.g. lymphocytes, monocytes and macrophages. Some of the lymphocytes, referred to as T cells (or T-cell), bear on their surface a T-cell receptor. T cell are broadly divided into cells expressing CD4 on their surface (also referred to as CD4-positive cells) and cells expressing CD8 on their surface (also referred to as CD8-positive cells). Some of the lymphocytes, referred to as B cells (or B-cells), bear on their surface a B-cell receptor.

Low-immunogenic biocompatible polymer. As used herein, a "low-immunogenic polymer" refers to a polymer which is not or is unlikely to elicit an immune response in an individual. This low-immunogenic polymer is also capable of masking an antigenic determinant of a cell and lowering or even preventing an immune response to the antigenic determinant when the antigenic determinant is introduced into a subject. A "biocompatible polymer" refers to a polymer which is non-toxic when introduced into a subject. Exemplary low-immunogenic biocompatible polymers includes, but are not limited to, polyethylene glycol (for example methoxypoly(ethylene glycol)), hyper-branched polyglycerol (HPG) and 2-alkyloxazoline (POZ).

Non-proliferative leukocyte. As used herein, the term "non-proliferative leukocyte" refers to a leukocyte which has been modified to no longer being capable of cellular proliferative (e.g. performing at least one complete division cycle). In some embodiments, this modification may be temporary and the non-proliferative properties of a leukocyte may be limited in time. For example, when a leukocyte is modified from a contact with a pharmacological agent capable of limiting its proliferation, the removal of the pharmacological agent from the cell culture can allow the leukocyte to regain its proliferative properties. In other embodiments, the modification is permanent and the modified leukocyte cannot regain its proliferative properties. For example, when a leukocyte is irradiated, it is not possible for it to regain its proliferative properties. In the context of the present application, the expressions "non-proliferative leukocyte" or "leukocyte limited from proliferating" are used interchangeably.

Peripheral blood mononuclear cells (PBMC). This term refers to the cell population recuperated/derived from the peripheral blood of a subject (usually a mammal such as a human). PBMC usually contains T cells, B cells and antigen presenting cells.

Pharmaceutically effective amount or therapeutically effective amount. These expressions refer to an amount (dose) of a cellular preparation effective in mediating a therapeutic benefit to a patient (for example prevention, treatment and/or alleviation of symptoms of an immune-associated disorder in which the ratio of Tregs to pro-inflammatory T cells is low when compared to a (sex- and aged-matched) healthy subject). It is also to be understood herein that a "pharmaceutically effective amount" may be interpreted as an amount giving a desired therapeutic effect, either taken in one dose or in any dosage or route, taken alone or in combination with other therapeutic agents.

Prevention, treatment and alleviation of symptoms. These expressions refer to the ability of a method or cellular preparation to limit the development, progression and/or symptomology of a immune-associated disorder associated to an abnormal/excessive immune response (in which the ratio of Tregs to pro-inflammatory T cells is low when compared to a (sex- and aged-matched) healthy subject). Broadly, the prevention, treatment and/or alleviation of symptoms encompasses increasing the levels of Treg cells and/or decreasing the levels of pro-inflammatory T cells. A method or cellular-based preparation is considered effective or successful for treating and/or alleviating the symptoms associated with the disorder when a reduction in the pro-inflammatory state (when compared to an untreated and afflicted individual) in the treated individual (previously known to be afflicted with the disorder) is observed. A method or cellular-based preparation is considered effective or successful for preventing the disorder when a reduction in the pro-inflammatory state (when compared to an untreated and afflicted individual) in the treated individual is observed upon an immunological challenge (such as, for example, an antigenic challenge).

Pro-inflammatory T cells. In the present context, pro-inflammatory T cells are a population of T cells capable of mediating an inflammatory reaction. Pro-inflammatory T cells generally include T helper 1 (Th1 or Type 1) and T helper 17 (Th17) subsets of T cells. Th1 cells partner mainly with macrophage and can produce interferon-γ, tumor necrosis factor-β, IL-2 and IL-10. Th1 cells promote the cellular immune response by maximizing the killing efficacy of the macrophages and the proliferation of cytotoxic CD8+ T cells. Th1 cells can also promote the production of opsonizing antibodies. T helper 17 cells (Th17) are a subset of T helper cells capable of producing interleukin 17 (IL-17) and are thought to play a key role in autoimmune diseases and in microbial infections. Th17 cells primarily produce two main members of the IL-17 family, IL-17A and IL-17F, which are involved in the recruitment, activation and migration of neutrophils. Th17 cells also secrete IL-21 and IL-22.

Regulatory T cells. Regulatory T cells are also referred to as Treg and were formerly known as suppressor T cell. Regulatory T cells are a component of the immune system that suppress immune responses of other cells. Regulatory T cells usually express CD3, CD4, CD8, CD25, and Foxp3. Additional regulatory T cell populations include Tr1, Th3, $CD8^+CD28^-$, $CD69^+$, and Qa-1 restricted T cells. Regulatory T cells actively suppress activation of the immune system and prevent pathological self-reactivity, i.e. autoimmune disease. The critical role regulatory T cells play within the immune system is evidenced by the severe autoimmune syndrome that results from a genetic deficiency in regulatory T cells. The immunosuppressive cytokines TGF-β and Interleukin 10 (IL-10) have also been implicated in regulatory T cell function. Similar to other T cells, a subset of regulatory T cells can develop in the *thymus* and this subset is usually referred to as natural Treg (or nTreg). Another type of regulatory T cell (induced Treg or iTreg) can develop in the periphery from naïve $CD4^+$ T cells. The large majority of Foxp3-expressing regulatory T cells are found within the major histocompatibility complex (MHC) class II restricted CD4-expressing ($CD4^+$) helper T cell population and express high levels of the interleukin-2 receptor alpha chain (CD25). In addition to the Foxp3-expressing $CD4^+CD25^+$, there also appears to be a minor population of MHC class I restricted $CD8^+$ Foxp3-expressing regulatory T cells. Unlike conventional T cells, regulatory T cells do not produce IL-2 and are therefore anergic at baseline. An alternative way of identifying regulatory T cells is to determine the DNA methylation pattern of a portion of the foxp3 gene (TSDR, Treg-specific-demthylated region) which is found demethylated in Tregs.

Splenocytes. This term refers to the cell population obtained from the spleen of a subject (usually a mammal such as a rodent). Splenocytes usually comprise T cell, B cell as well as antigen presenting cells.

Syngeneic cell. A cell is considered "syngeneic" with respect to a subject (or a cell derived therefrom) if it is sufficiently identical to the subject so as to prevent an immune rejection upon transplantation. Syngeneic cells are derived from the same animal species.

Viable. In the present context, the term "viable" refers to the ability of a cell to complete at least one cell cycle and, ultimately proliferate. A viable cell is thus capable of proliferating. By opposition, the term "non-viable" or "non-proliferative" both refer to a cell which is no longer capable of completing at least one cell cycle. By comparison, the term "cycle arrest" refers to a cell which has been treated to halt its cell cycle progression (usually with a pharmacological agent) but which is still capable of re-entering the cell cycle (usually when the pharmacological agent is removed).

Xenogeneic cell. A cell is considered "xenogeneic" with respect to a subject (or a cell derived from the subject) when it is derived from a different animal species than the subject. A xenogeneic cell is expected to be rejected when transplanted in an immunocompetent host.

BRIEF DESCRIPTION OF THE DRAWINGS

Having thus generally described the nature of the invention, reference will now be made to the accompanying drawings, showing by way of illustration, a preferred embodiment thereof.

FIG. 5 illustrates Treg levels in the spleen (A), in the brachial lymph nodes (B) or in the blood (C) in function of time (hours post injection) following administration of donor splenocytes or control (Δ naïve; ▲ soluble mPEG; ☐ syngeneic cells; ■ mPEG syngeneic cells; ● allogeneic cells; ○ mPEG allogeneic cells). PEGylation of allogeneic donor murine splenocytes resulted in a significant in vivo immunomodulatory effect giving rise to significantly elevated Treg lymphocytes. As noted, in all three tissues, a significant (p<0.001 at 120 h) increase in Treg lymphocytes over that observed in naïve mice was noted in mice receiving mPEG-modified allogeneic donor cells. In stark contrast, a significant decrease in Tregs (relative to naïve mice) is noted in mice transfused with unmodified allogeneic splenocytes. In comparing the absolute difference between the control PEGylated splenocytes (dotted area or Δd) the differential impact of donor cell PEGylation can be fully appreciated. Importantly, as noted at 120 h, transfusion of soluble mPEG, syngeneic cells or mPEG-syngeneic cells had no significant effect on the Treg lymphocyte population. The range observed in naïve mice is denoted by the grey bars. PEGylated murine splenocytes were modified with 1 mM SVAmPEG (20 kDa).

FIG. 6 illustrates Th17 levels in the spleen (A), in the brachial lymph nodes (B) or in the blood (C) in function of time (hours post injection) following administration of donor splenocytes or control (Δ naïve; ▲ soluble mPEG; ☐ syngeneic cells; ■ mPEG syngeneic cells; ● allogeneic cells; ○ mPEG allogeneic cells). PEGylation of allogeneic donor murine splenocytes resulted in a significant in vivo immunomodulatory effect as evidenced by baseline levels of Th17 lymphocytes. As shown, unmodified allogeneic splenocytes resulted in a dramatic increase (p<0.001 at all time points >24 h) in Th17 lymphocytes. However, PEGylation of the allogeneic donor cells completely abrogates this increase and the Th17 levels stay in the range seen in naïve mice (grey area). In comparing the absolute difference between the control and PEGylated splenocytes (dotted area or Δd) the differential impact of donor cell PEGylation can be fully appreciated. Importantly, as noted at 120 h, transfusion of soluble mPEG, syngeneic cells or mPEG-syngeneic cells had no significant effect on the Th17 lymphocyte population. The range observed in naïve mice is denoted by the grey bars. PEGylated murine splenocytes were modified with 1 mM SVAmPEG (20 kDa).

FIG. 7 shows the ratio of Treg/Th17 levels five days following administration of donor splenocytes. PEGylation of allogeneic donor murine splenocytes resulted in a significant in vivo immunomodulatory effect. The panels in (A) show the ratio of Treg/Th17 levels in spleen (A1), "brachial" lymph node (A2), and peripheral blood (A3). The graph in (B) compares the ratio when non-modified allogeneic cells (right side) or PEGylated allogeneic cells (left side) are administered. * denotes statistical significance (p<0.001).

FIG. 8 shows the long-term immunomodulatory effects of PEGylation of donor cells. The immunomodulatory effects of the PEGylated splenocytes is long lived and prevents changes in Treg and Th17 levels consequent to rechallenge with unmodified allogeneic cells. Results are shown for percentage of Tregs (upper panels) and Th17 cells (lower panels) in the spleen (right panels), brachial lymph nodes (middle panels) and peripheral blood (left panels) for mice transfused with allogeneic splenocytes (■) and mPEG allogeneic splenocytes (☐). Thirty days post-transfusion with mPEG allogeneic splenocytes (○), mice still demonstrated significantly elevated Treg levels demonstrating persistence of the immunomodulation. When mice previously challenged with mPEG-allogeneic splenocytes were rechallenged 30 days later with unmodified allogeneic splenocytes (●) no decrease in Treg or increase in Th17 cells were observed demonstrating tolerance/anergy. Shaded area on the graph indicate Treg and Th17 levels in naïve mice. PEGylated murine splenocytes were modified with 1 mM SVAmPEG (20 kDa).

FIG. 21 illustrates that conditioned murine plasma prepared from mice injected with saline, allogeneic or mPEG allogeneic cells similarly modulates Treg and Th17 differentiation levels in vivo. Conditioned murine plasma (obtained from donor mice 5 days post leukocyte transfer) was administered to mice and Treg/Th17 levels were measured in the spleen, the lymph nodes and the blood five days after treatment. Results are shown for naïve animals (white bars) and animals receiving conditioned plasma prepared from animals having received saline (Plasma (Saline); light grey bars), animals having received unmodified allogeneic splenocytes (Plasma (Allo); dark grey bars) or polymer-modified allogeneic splenocytes (Plasma (mPeg-All); hatched bars). Results are shown as the percentage of Treg cells (in function of $CD4^+$ cells) in the spleen (A), the lymph node (B) or the blood (C). Results are also shown as the percentage of Th17 cells (in function of $CD4^+$ cells) in the spleen (D), the lymph node (E) or the blood (F). *=p<0.01 relative to saline control animal; #=p<0.01 relative to animal administered with Plasma(Allo)-conditioned plasma.

DETAILED DESCRIPTION

Figure 1:
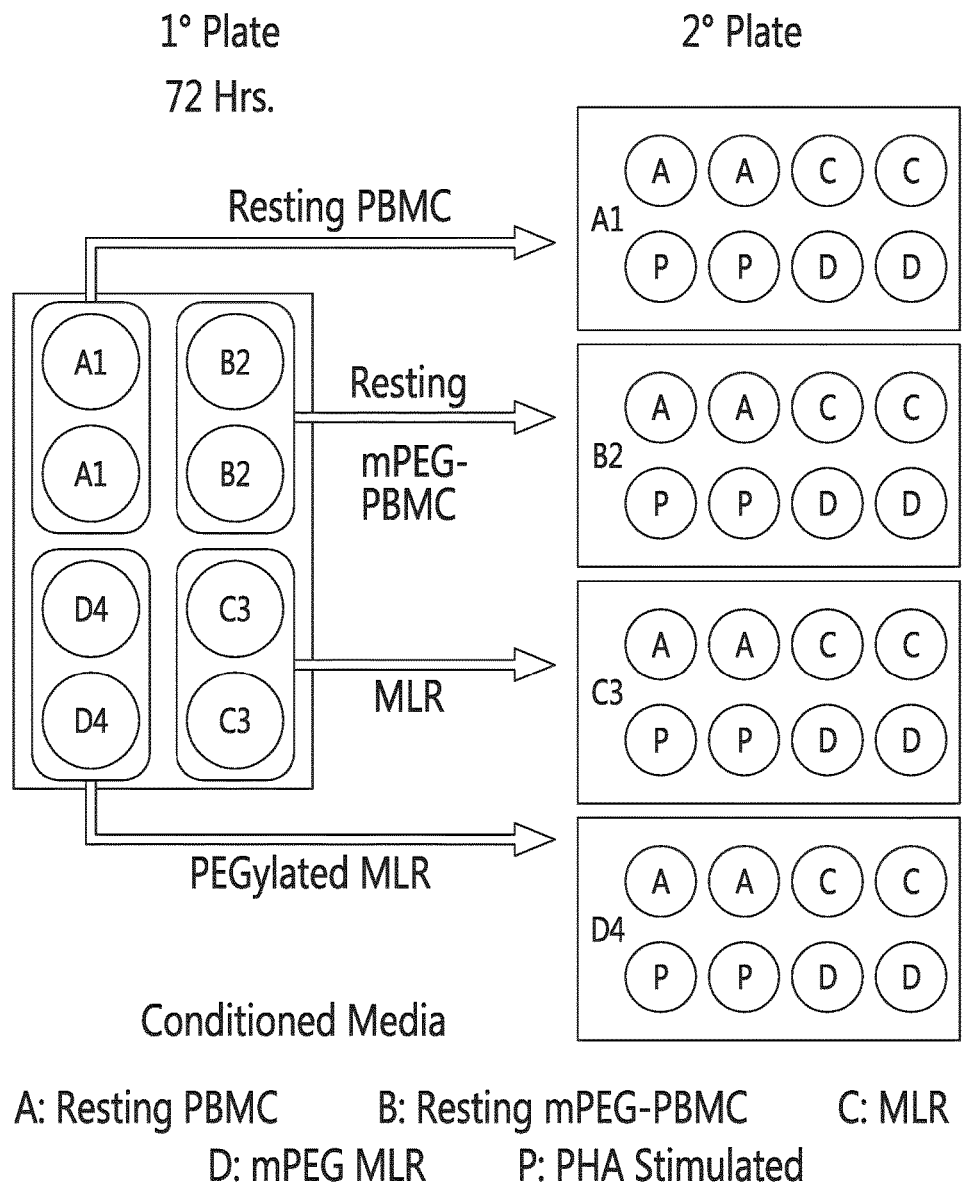
FIG. 1 shows diagrammatically the conditioned media protocol. A primary)(1°) two-way mixed lymphocyte reaction (MLR) was initiated using two HLA-disparate populations consisting of unmodified or polymer-grafted (1 mM SVAmPEG; 5 kDa) PBMC. Within the mPEG-MLR, only one donor population was PEGylated. At 72 h, the conditioned media from the wells were collected. Secondary)(2°) mixed lymphocyte reactions using control and PEGylated PBMC from the same donors were initiated. A mitogen (PHA) stimulation control was added to assure that the media collected would support proliferation. 1° MLR Conditioned media: 1=Resting unmodified PBMC; 2=Resting mPEG-PBMC; 3=Control MLR; and 4=mPEG-MLR. 1° MLR/2° MLR Cell Types or Stimulation: A=Resting PBMC; B=Resting mPEG PBMC; C=MLR; D=mPEG MLR; P=PHA stimulation.

In accordance with the present invention, there is provided cellular-based preparations for increasing the level of regulatory T cells and/or decreasing the level of pro-inflammatory T cells for inducing a state of anergy, tolerance, loss of pro-inflammatory, and/or immuno-quiescence in a subject in need thereof. The cellular-based preparations and therapies presented herewith concern the use of at least two distinct leukocyte populations which are considered allogeneic with respect to one another, wherein at least one of the leukocyte population is modified to bear on its surface a low-immunogenic biocompatible polymer so as to prevent pro-inflammatory allo-recognition (but allowpro-tolerogenic allo-recognition) between the two leukocyte populations. In the cellular-based preparations described herein, at least one of the leukocyte population is considered non-proliferative. The cellular-based preparations can be obtained by modifying a first leukocyte (which is considered immunogenic or allogeneic to the treated subject) to bear on its surface a low-immunogenic biocompatible polymer and to become non-proliferative. The cellular-based preparation can also be obtained by culturing the first leukocyte (bearing the low-immunogenic biocompatible polymer) with a leukocyte from the subject to obtain a cultured cellular preparation (wherein one of the two leukocyte population is refrained from proliferating). Alternatively, the cellular-based preparation can be obtained by isolating the cell culture supernatant of a culture a second and a third leukocytes (wherein the second leukocyte is allogeneic to the third leukocyte and at least one of the second or third leukocyte is considered non-proliferative) and the second leukocyte has been modified to bear on its surface a low-immunogenic biocompatible polymer.

As it will be shown below, polymer-based bioengineering of leukocytic cells provides a significant opportunity to modulate the responsiveness (i.e., immunoquiescent versus pro-inflammatory) of the recipient's immune system. Without wishing to be bound to theory, it is hypothesized that polymer-modified white blood cells (e.g. leukocytes), and preparations arising from such cells, can be used to induce Tregs and/or attenuate Th17/1 and NK (natural killer) cell upregulation, to prevent the pro-inflammatory immune response to allogeneic donor cells. Moreover, it is proposed that polymer-modified allogeneic white blood cells (e.g. leukocytes) can be used therapeutically in various diseases (such as auto-immunity or an excessive immune response) to increase the levels Treg cells and/or decrease proinflammatory effector cells, to ultimately increase the ratio of regulatory T cells to pro-inflammatory T cells thereby attenuating the incidence and/or severity of the disease pathology.

The present invention provides experimental evidence that the administration of polymer-modified (and in some embodiments, the PEGylated) of allogeneic human peripheral blood mononuclear cells (PBMC) or murine splenocytes can give rise to immunoquiescence (tolerance and/or anergy). This anergy was shown in vitro by conducting and analyzing mixed lymphocyte reactions (MLR) and conditioned media experiments for lymphocyte proliferation, differentiation and cytokine production. For lymphocyte differentiation, both in vitro and in vivo, the expansion/contraction of the regulatory T (Treg; favoring tolerance or anergy) and Th17 (pro-inflammatory and favoring allorejection) populations were quantitated. To more fully assess the systemic biologic effect of polymer-mediated immune tolerance, in vivo murine studies were also conducted to determine both the Treg and Th17 population modulations as well as whether differential effects were noted in the spleen, lymph nodes and blood of control and treated animals.

Methods for Modulating the Treg/Pro-Inflammatory T Cells Ratio

The present invention provides methods and cellular preparations for increasing the ratio of the level of regulatory T cells with respect to the level of pro-inflammatory T cells. In the present invention, the ratio can be increased either by augmenting the level of regulatory T cells in the subject or decreasing the level of pro-inflammatory T cells in the subject. Alternatively, the ratio can be increased by augmenting the level of regulatory T cells in the subject and decreasing the level of pro-inflammatory T cells in the subject. When the Treg/pro-inflammatory T cells ratio is increased in a subject, it is considered that a state of anergy and/or of increased tolerance is induced or present in the subject. The induction of a state of anergy or immunotolerance in individuals experiencing an abnormally elevated immune reaction can be therapeutically beneficial for limiting the symptoms or pathology associated with the abnormally elevated immune reaction. In some embodiments, it is not necessary to induce a state of complete anergy or tolerance, a partial induction of anergy or tolerance can be beneficial to prevent, treat and/or alleviate the symptoms of a disorder associated with a pro-inflammatory state (such as, for example, an auto-immune disease or an excessive immune response).

In order to increase the Treg/pro-inflammatory T cells ratio, an allogeneic cellular preparation can be administered to the subject in a therapeutically effective amount. In such instance, the cellular preparation comprises a first leukocyte that has been modified with a low-immunogenic biocompatible polymer and that is considered to be non-proliferative. Prior to its modification with a low-immunogenic biocompatible polymer, the first leukocyte is considered immunogenic (e.g. allogeneic) with respect to the subject because it is able to induce an immune response (e.g. a cell-mediated immune response) when administered to the subject. As indicated above, it is possible to determine if two cells are considered immunogenic with respect to one another by conducting conventional in vitro assays, such as a mixed lymphocyte reaction. It is also expected that MHC-disparate cells would be considered immunogenic with respect to one another. In an embodiment, the first leukocyte can be xenogeneic to the subject. However, the first leukocyte cannot be autologous or syngeneic to the subject. Prior to its modification, the first leukocyte is considered to be viable and capable of cellular proliferation. The first leukocyte can even be optionally expanded and or differentiated (e.g. from naïve to Treg) in vitro, however, in such embodiment, the first leukocyte is modified to become non-proliferative prior to its administration to the subject.

Alternatively, in order to increase the Treg/pro-inflammatory T cells ratio, a cultured cellular preparation can be administered to the subject in a therapeutically effective amount. In order to do so, a the first leukocyte (modified with the low-immunogenic biocompatible polymer) is placed in contact in vitro with a leukocyte from the subject or a leukocyte syngeneic to the subject. One of the two leukocyte population (preferably the first leukocyte population) is modified, prior to the co-culture, to refrain from proliferating. The two cell populations are cultured under immunogenic conditions to provide a cultured cellular preparation. However, since the first leukocytes has been modified with a low-immunogenic biocompatible polymer, no or little pro-inflammatory allo-recognition is observed in the cell culture. In an embodiment, one of the two population of leukocytes is not per se from the subject but is syngeneic to the subject. In an embodiment, the leukocytes from the subject (or syngeneic to the subject) are cultured under conditions favoring the expansion (e.g. proliferation) and/or differentiation (e.g. naïve to Treg) prior to the administration to the subject (either prior to, during or after the co-culture). In another embodiment, the first leukocytes are cultured under conditions favoring the expansion (e.g. proliferation) and/or differentiation (e.g. naïve to Treg) prior to the co-culture. In some embodiments, it is preferable to remove the first leukocyte from the cultured cellular preparation prior to its administration to the subject. Methods of separating the two cellular populations are known to those skilled in the art and include, without limitation, cell sorting and magnetic beads. In an embodiment, the leukocyte from the subject can also be modified to comprise, on its cell surface, the low-immunogenic biocompatible polymer either prior to the cell culture or after the cell culture (e.g. prior to the administration to the subject).

An alternative way of increasing the Treg/pro-inflammatory T cell ratio concerns the administration of the supernatant of a cell culture of a second leukocyte (that has been modified with a low-immunogenic biocompatible polymer prior to cell culture) and a third leukocyte (optionally modified with a low-immunogenic biocompatible polymer prior to or after cell culture). In such embodiment, at least one of the second or third leukocyte is limited from proliferating. In some embodiments, the cell culture supernatant can comprise leukocytes or leukocyte fractions (for example a part of the cytoplasmic membrane). The second leukocyte is considered immunogenic (e.g. allogeneic) with respect to the third leukocyte because if the second leukocyte was not modified and placed into contact with the third leukocyte, an immune response (e.g. a cell-mediated immune response such as a pro-inflammatory allo-recognition) would occur. It is possible to determine if two cells are considered immunogenic with respect to one another by conducting conventional in vitro assays, such as the mixed lymphocyte reaction. It is also expected that MHC-disparate cells would be considered immunogenic with respect to one another. In an embodiment, the second leukocyte cell can be xenogeneic to the third leukocyte However, the second leukocyte cannot be autologous or syngeneic to the third leukocyte. In the methods and cellular compositions described herein, it is possible that one of the second or third leukocyte be syngeneic or derived from the subject which will be treated. In addition, in other embodiments, both the second and/or third leukocytes can be considered allogeneic or xenogeneic to the subject which will be treated. The leukocytes are being cultured in conditions favoring in vitro expansion and/or differentiation of naïve T cells to immunomodulatory (e.g. Treg) cells of the leukocyte population. Prior to the cell culture, one or both leukocyte populations can optionally be expanded. Importantly, the cell culture supernatant, apart from being optionally filtered to remove cells and cellular debris, is not submitted to further extraction/size fractionation or specific enrichment of one of its components prior to its administration to the subject. The cell culture supernatant thus comprises the conditioned media from the cell culture (e.g. cellular by-products such as cytokines).

An alternative way of increasing the Treg/pro-inflammatory Tcell ratio in a subject to be treated, it is also possible to administer the conditioned blood (preferably the plasma or the serum) of a test subject (usually an animal such as a mammal) that has been administered or transfused with a first non-proliferative leukocyte modified to bear on its surface a low-immunogenic biocompatible polymer. Methods for recuperating the blood or the blood fractions are known to those skilled in the art and usually include cell lysis and/or centrifugation. In some embodiments, this conditioned blood can comprise the first leukocyte or a derivative therefrom (a part of the cytoplasmic membrane from the first leukocyte for example). The first leukocyte is considered immunogenic (e.g. allogeneic) with respect to the test subject because if the first leukocyte was not modified and transfused into the test subject, an immune response (e.g. a cell-mediated immune response) would occur. In another embodiment, the first leukocyte can be allogeneic or xenogeneic with respect to the test subject. However, the first leukocyte cannot be autologous or syngeneic to the animal. In some embodiments, the first leukocyte can be allogeneic to the subject which will be treated. In alternative embodiment, the first leukocyte can be syngeneic or derived from the subject which will be treated with the conditioned blood.

In the context of the present invention, some of the leukocytes used in the cellular preparations are both modified for bearing a low-immunogenic biocompatible polymer and being modified to no longer be capable of proliferation. The order in which the leukocytes are modified (modification with polymer and modification to prevent proliferation) is not important. Leukocytes can be first modified to bear the polymer and then modified to refrain from proliferating. Alternatively, the leukocytes can be first modified to refrain from proliferating and then modified to bear the polymer.

The leukocytes described herein can be derived from any animals, but are preferably derived from mammals (such as, for example, humans and mice).

In the methods and cellular preparations provided herewith, the surface of the leukocyte is or can be modified with a low-immunogenic biocompatible polymer. For some specific applications, it may be preferable to modify the surface of the leukocyte with a single type of low-immunogenic biocompatible polymer. However, for other applications, it is possible to modify the surface of the leukocyte with at least two different types of low-immunogenic biocompatible polymers.

In order to achieve these modifications, the low-immunogenic biocompatible polymer can be covalently bound to the cytoplasmic membrane of the leukocyte and, in a further embodiment, a membrane-associated protein of the surface of the leukocyte or inserted, via a lipophilic tail, in the cytoplasmic membrane of the leukocyte. When the polymer is bound to a membrane-boud protein, the membrane-associated protein must have at least a portion which is accessible on the external surface of the cytoplasmic membrane of the leukocyte for being covalently attached to the polymer. For example, the membrane-associated protein can be partially embedded in the cytoplasmic membrane or can be associated with the external surface of the membrane without being embedded in the cytoplasmic membrane. The low-immunogenic biocompatible polymer can be covalently bound to a plurality of membrane-associated proteins. In an alternative or complementary embodiment, the low-immunogenic biocompatible polymer can be inserted in the cytoplasmic membrane by using a lipid-modified polymer.

In some embodiment, the low-immunogenic biocompatible polymer can be polyethylene glycol (methoxy polyethylene glycol for example). The polyethylene glycol can be directly and covalently bound to a membrane-associated protein or, alternatively, a linker attaching the low-immunogenic biocompatiable polymer can be used for attaching the polymer to the protein. Exemplary linkers are provided in U.S. Pat. No. 8,007,784 (incorporated herewith in its entirety). In alternative embodiments, the low-immunogenic polymer can be POZ or HPG.

In the methods and cellular preparations provided herewith, the leukocytes can be mature leukocytes or be provided in the form of stem cells. For example, leukocytes can be obtained from isolating peripheral blood mononuclear cells (PBMC) from the subject. Optionally, the PBMCs can be differentiated in vitro into DC or DC-like cells. Alternatively, the leukocytes can be obtained from the spleen (e.g. splenocytes). Leukocytes usually include T cells, B cells and antigen presenting cells. In the methods and cellular preparations provided herewith, the leukocytes are not erythrocytes since the polymer-modified erythrocytes are not capable of increasing the ratio Treg/pro-inflammatory T cells when they were administered in a subject. However, traces of erythrocytes in the leukocytic preparations are tolerated (for example, less than about 10%, less than about 5% or less than about 1% of the total number of cells in the preparation).

Even though it is not necessary to further purify the leukocytes to conduct the method or obtain the cellular preparation, it is possible to use a pure cell population or a relatively homogenous population of cells as leukocytes. This pure cell population and relative homogenous population of cells can, for example, essentially consist essentially of a single cell type of T cells, B cells, antigen presenting cells (APC) or stem cells. Alternatively, the population of cells can consist essentially of more than one cell type. The population of cells can be obtained through conventional methods (for example cell sorting or magnetic beads). In an embodiment, when the population of cells consist of a single cell type (for example, T cells), the percentage of the cell type with respect to the total population of cells is at least 90%, at least 95% or at least 99%. The relatively homogenous population of cells are expected to contain some contaminating cells, for example less than 10%, less than 5% or less than 1% of the total population of cells.

The cell culture supernatant used in the method or in the cellular preparation can be obtained by co-culturing a second leukocyte cellular population with a third leukocyte cellular population. It is also possible to co-culture a second leukocyte homogenous cell population (such as, for example, a T pure cell population or a substantially pure T cell population) with a third leukocyte preparation. It is also contemplated to culture a second leukocyte population with a third leukocyte population (such as, for example, a pure T cell population or a substantially pure T cell population).

In addition, and as indicated above, when the subject's own cells are used in the cell culture (to provide the culture supernatant), they can be modified to be covalently bound to the low-immunogenic biocompatible polymer and cultured with the first leukocyte. Alternatively, they can remain unmodified (e.g. not covalently bound to the low-immunogenic biocompatible polymer) and cultured with the first leukocyte which has been modified to be covalently bound to the low-immunogenic biocompatible polymer.

In the methods and preparations presented herewith, it is required to inhibit/limit the proliferation of at least one of the leukocyte population being contacted. For example, a leukocyte can be treated/modified prior to cell culture or its administration into the subject in order to inhibit/limit the cell from proliferating in the subject. For example, the cell can be irradiated (e.g. γ-irradiation) prior to its introduction in the subject or its introduction into a culture system. Upon irradiation, the leukocyte is not considered viable (e.g. capable of proliferation). In an embodiment, polymer grafting can affect the leukocyte viability and can be used to refrain the leukocyte from proliferating. Alternatively, leukocyte can be treated with a pharmacological agent which halts cell cycle progression. Upon the administration of such pharmacological agent, the leukocyte is considered viable since it can resume cellular proliferation when the agent is removed from the cell-containing medium. When the cell culture supernatant is used in the method, it is important that only one of the two cell populations be inhibited/limited from proliferating and that the other cell population be able to proliferate.

The conditioned blood that can be used in the method can be obtained by administering (preferably transfusing or intravenously administering), to a test subject, a first leukocyte considered allogeneic to the test subject which has been modified with a low-immunogenic and biocompatible polymer. It is also possible to transfuse a first leukocytic homogenous cell population (such as, for example, a T pure cell population or a substantially pure T cell population) to the subject. The blood is recuperated from the subject after a time sufficient to induce in the subject a state of anergy or tolerance. As indicated above, the first leukocytic cellular preparation is inhibited/limited from proliferating prior to administration to the animal.

As shown herein, the administration of the cellular preparations induces a state of anergy or immune tolerance in the treated subject. In some embodiments, the state of anergy can persist long after the administration of the cellular preparation or the cell culture supernatant (as shown below, at least 270 days in mice). In an optional embodiment, the state of anergy does not revert back to a pro-inflammatory state upon a challenge with, for example, an immunogen (such as an immunogenic or allogeneic cell). Consequently, the methods and cellular preparations described herein are useful for the treatment, prevention and/or alleviation of symptoms associated with abnormal/excessive immune responses and conditions associated thereto.

Autoimmunity arises consequent to an animal/individual's immune system recognizing their own tissues as "non-self". Autoimmunity is largely a cell-mediated disease with T lymphocytes playing a central role in "self" recognition and are, in many cases, also the effector cells. The Non-Obese Diabetic (NOD) mouse is an inbred strain that exhibits the spontaneous development of a variety of autoimmune diseases including insulin dependent diabetes. The murine autoimmune diabetes develops around 16 to 20 weeks of age and has been extensively used to study the mechanisms underlying autoimmune-mediated diabetes, therapeutic interventions and the effect of viral enhancers on disease pathogenesis. Diabetes develops in NOD mice as a result of insulitis, a leukocytic infiltrate of the pancreatic islets. This can be exacerbated if mice are exposed to killed *mycobacterium* or other agents (Coxsackie virus for example). Multiple studies have established that the pathogenesis of diabetes in the NOD mouse is very similar to that observed in human type I diabetes (T1D) in that it is characterized by the breakdown of multiple tolerance pathways and development of severe insulitis of the islets prior to β-cell destruction. Moreover, T cells (including Th1, Th17 and Tregs) have been identified as key mediators of the autoimmune disease process though other cells (NK cells, B-cells, DC and macrophages) are also observed. Indeed, the NOD mouse model has translated into successful clinical human trials utilizing T-cell targeting therapies for treatment of many autoimmune diseases, including T1D.

The loss of function arising from pro-inflammatory allo-recognition is exemplified by the destruction of the islets of Langerhans (insulin secreting 11 cells) in the pancreas of the NOD mice leading to the onset of Type 1 diabetes. In this context context, pro-tolerogenic allo-recognition is characterized by the protection and survival of the islets of Langerhans and the inhibition of diabetes in the NOD mouse.

Treatment of most autoimmune diseases is problematic and normally focused on addressing disease symptoms, not causation. Typically, treatment for chronic autoimmune disease is via systemic steroid (e.g., dexamethasone) administration to induce a general immunosuppression and to act as an anti-inflammatory agent. It is believed that one mechanism of this immunosuppression may be the induction of Treg cells. In addition to steroids, the administration of IVIg (pooled, polyvalent, IgG purified from the plasma of >1 000 blood donors) can also effectively treat some autoimmune diseases including immune thrombocytopenia (ITP). Interestingly, the onset of diabetes in NOD mice can also be delayed, but not fully blocked by administration of IVIg and this may correlate with induction of Tregs (and/or IL-10). Hence, novel approaches to increase Treg cells (and/or IL-10) while decreasing inflammatory T cell responses (e.g., Th17, NK cells) could be beneficial in treating autoimmune diabetes.

A state of anergy or immune tolerance can be considered therapeutically beneficial in subjects experiencing (or at risk of experiencing) an abnormal immune response, such as for example an auto-immune disease. Some auto-immune diseases are associated with either low levels of Tregs and/or elevated levels of pro-inflammatory T cells (such as Th17 and/or Th1). Such auto-immune diseases include, but are not limited to, type I diabetes, rheumatoid arthritis, multiple sclerosis, lupus, immune thrombocytopenia, experimental autoimmune encephalomyelitis, auto-immune uveitis, psoriasis inflammatory bowel disease, scleroderma and Crohn's disease. Because it is shown herein that the cellular preparations are beneficial for increasing the ratio Tregs/pro-inflammatory T cells, it is expected that administration of the cellular preparations to afflicted subject will alleviate symptoms associated with the auto-immune disease.

A state of anergy or tolerance can also be considered therapeutically beneficial in subjects at risk of developing an abnormally elevated/excessive immune response. Such abnormally elevated immune response can be observed in subjects receiving a vaccine. For example, it has been shown that subjects receiving a respiratory syncytial virus (RSV) vaccine develop an excessive immune response. Such abnormally elevated immune response can also be observed in subjects receiving a transplant (cells or tissues). In these conditions, the methods and cellular preparations can be applied to prevent or limit the elevated/excessive immune response. The cellular preparation, cultured cellular preparation or the cell culture supernatant can be co-administered with the vaccine or the transplant. Alternatively, the cellular preparation, the cultured cellular preparation or the cell culture supernatant can be administered prior to the administration of the vaccine or the introduction of the transplant to induce a state of anergy or tolerance in the subject. In some embodiments, the first, second and/or third leukocyte can be syngeneic to the tissue/cell donor.

In the methods and cellular preparations described herein, it is contemplated that the cellular-based preparations be optionally administered with other therapeutic agents known to be useful for the treatment, prevention and/or alleviation of symptoms of conditions associated to an excessive/abnormal immune response, such as, for example, cortisone, IL-10, IL-11 and/or IL-12.

Processes for Obtaining Cellular Preparations

The cellular preparations presented described herein can be obtained by contacting two distinct and allogeneic leukocyte populations. One of the two leukocyte population is modified to bear on its surface (and, in some embodiment, to be covalently bound to) a low-immunogenic biocompatible polymer. One of the two leukocyte population is modified to be refrained from proliferating. The two leukocyte populations are contacted under conditions so as to limit (and in some embodiments prevent) pro-inflammatory allo-recognition and to allow pro-tolerogenic allo-recognition.

It is important that the polymer used exhibits both low-immunogenicity and biocompatibility once introduced into a cell culture system or administered to the test subject. It is shown below that polyethylene glycol (particularly methoxypoly(ethylene glycol)) and POZ have been successfully used to modify leukocytes and provide corresponding cellular preparations having the ability to increase a ratio of Treg cells to pro-inflammatory T cells in vitro and in vivo. These experimental results suggest that other low-immunogenic biocompatible polymers can also be used to modify leukocytes. These other low-immunogenic biocompatible polymers include, but are not limited to an hyperbranched polyglycerol (HPG). In some embodiments, it is preferable to use a single type of polymer to modify the surface of leukocytes. In other embodiments, it is possible to use at least two distinct types of polymers to modify the surface of the leukocyte.

In an embodiment, the low-immunogenic biocompatible polymer can be covalently associated with the membrane-associated protein(s) of the leukocyte by creating a reactive site on the polymer (for example by deprotecting a chemical group) and contacting the polymer with the leukocyte. For example, for covalently binding a methoxypoly(ethylene glycol) to the surface of a leukocyte, it is possible to incubate a methoxypoly(-ethylene glycol) succinimidyl valerate (reactive polymer) in the presence of the leukocyte. The contact between the reactive polymer and the leukocyte is performed under conditions sufficient for providing a grafting density which will prevent pro-inflammatory allo-recognition and allow pro-tolerogenic allo-recognition. In an embodiment, the polymer is grafted to a viable leukocyte and under conditions which will retain the viability of the leukocyte. A linker, positioned between the surface of the leukocyte and the polymer, can optionally be used. Examples of such polymers and linkers are described in U.S. Pat. Nos. 5,908,624; 8,007,784 and 8,067,151. In another embodiment, the low-immunogenic biocompatible polymer can be integrated within the lipid bilayer of the cytoplasmic membrane of the leukocyte by using a lipid-modified polymer.

As indicated above, it is important that the low-immunogenic biocompatible polymer be grafted at a density sufficient for preventing pro-inflammatory allo-recognition and allow pro-tolerogenic allo-recognition). In an embodiment, the polymer is polyethylene glycol (e.g. linear) and has an average molecular weight between 2 and 40 KDa as well as any combinations thereof. In a further embodiment, the average molecular weight of the PEG to be grafted is at least 2, 3, 4, 5, 10, 15, 20, 25, 30, 35 or 40 kDa. In another embodiment, the average molecular weight of the PEG to be granted is no more than 40, 35, 30, 25, 20, 15, 10, 5, 4, 3, or 2 kDa. In another embodiment, the grafting concentration of the polymer (per $20 \times 10^6$ cells) is at least 1, 1.5, 2, 2.5, 5, 6, 7, 8, 9 or 10 mM. In still another embodiment, the grafting concentration of the polymer (per $20 \times 10^6$ cells) is no more than 10, 9, 8, 7, 6, 5, 2.5, 2, 1.5 or 1 mM. In order to determine if pro-inflammatory allo-recognition occurs (or is prevented), various techniques are known to those skilled in the art and include, but are not limited to, a standard mixed lymphocyte reaction (MLR), high molecular weight mitogen stimulation (e.g. PHA stimulation) as well as flow cytometry (Chen and Scott, 2006). In order to determine if a weak pro-tolerogenic allo-recognition occurs (or is prevented), various techniques are known to those skilled in the art and include, but are not limited to, the assessment of the level of expansion and differentiation of Treg cells and or prevention of Th17 expansion/differentiation. In an embodiment, the polymer is selected and grafted to the modified leukocyte to provide to the modified leukocyte a pro-inflammatory/pro-tolerogenic allo-recognition substantially similar to the one observed in a mixed lymphocyte reaction between a first leukocyte modified to be grafted with 20 kDa mPEG at a density of at least 0.5 mM (and preferably 1 mM) per $20 \times 10^6$ cells and incubated with a second (unmodified) allogeneic leukocyte.

Before or after being modified with a low-immunogenic biocompatible polymer, the leukocyte can be modified to refrain them from being proliferative. For example, the cell can be irradiated (e.g. γ-irradiation) prior to its introduction in the subject or its introduction into a culture system. Upon irradiation, the leukocyte is not considered viable (e.g. capable of proliferation). In an embodiment, polymer grafting can affect the leukocyte viability and can be used to refrain the leukocyte from proliferating. Alternatively, leukocyte can be treated with a pharmacological agent which halts cell cycle progression. Upon the administration of such pharmacological agent, the leukocyte is considered viable since it can resume cellular proliferation when the agent is removed from the cell-containing medium.

As indicated above, the leukocytes can be inhibited/limited from proliferating prior to their introduction in a cell culture or administration to the test subject. For example, the first and/or second leukocyte can be irradiated to halt its proliferation prior to its administration to the subject, its contact with the leukocyte from the subject or its contact with the third leukocyte. In some embodiments, the first and/or second leukocyte can first be modified with the low-immunogenic biocompatible polymer and then inhibited/limited from proliferating. In other embodiments, the first and/or second leukocyte can first be inhibited/limited from proliferating and then modified with the low-immunogenic biocompatible polymer.

To provide the cellular preparations described herewith, the leukocytes used can be mature leukocytes or be provided in the form of stem cells. For example, leukocytes can be obtained from isolating peripheral blood mononuclear cells (PBMC) from the subject. Optionally, the PBMCs can be differentiated in vitro into dendritic (DC) or DC-like cells. Alternatively, the leukocytes can be obtained from the spleen (e.g. splenocytes). Leukocytes usually include T cells, B cells and antigen presenting cells. For providing the cellular preparations, the leukocytes are not erythrocytes since the polymer-modified erythrocytes are not capable of causing a pro-tolerogenic allo-recognition when administered in a test subject. However, traces of erythrocytes in the leukocyte population used are tolerated (for example, less than about 10%, less than about 5% or less than about 1% of the total number of cells in the preparation).

Even though it is not necessary to further purify the leukocytes to provide the cellular preparations, it is possible to use a pure cell population or a relatively homogenous population of cells as leukocytes. This "pure" cell population and "relative homogenous population" of cells can, for example, essentially consist essentially of a single cell type of T cells, B cells, antigen presenting cells (APC) or stem cells. Alternatively, the population of cells can consist essentially of more than one cell type. The population of cells can be obtained through conventional methods (for example cell sorting or magnetic beads). In an embodiment, when the population of cells consist of a single cell type (for example, T cells), the percentage of the cell type with respect to the total population of cells is at least 90%, at least 95% or at least 99%. The relatively homogenous population of cells are expected to contain some contaminating cells, for example less than 10%, less than 5% or less than 1% of the total population of cells.

The leukocytes can be obtained from any animals, but are preferably derived from mammals (such as, for example, humans and mice). In an embodiment, the leukocytes can be obtained from a subject intended to be treated with the cellular preparations.

In an optional embodiment, to obtain the cellular preparation, the first leukocyte (modified to bear the low-immunogenic biocompatible polymer) can be placed in cell culture (in immunogenic conditions) with a leukocyte from the subject (or a leukocyte syngeneic to the subject) and the resulting cultured cellular preparation can be administered to the subject in need thereof. The cultured cellular preparation comprises at least the cultured leukocyte from the subject (or the cultured leukocyte syngeneic to the subject). In some embodiment, the cultured leukocyte from the subject (or the leukocyte syngeneic to the subject) can be modified (either prior to or after the cell culture) to bear the low-immunogenic biocompatible polymer. In the co-culture, at least one of the two leukocyte preparation is also modified to refrain from proliferating. In additional embodiments, the cultured leukocytes can be expanded and/or differentiated (from naïve to Treg) in vitro prior to their administration to the subject (prior to, during or after the co-culture). The cultured cellular preparation can be formulated to include or exclude the first leukocyte.

When a co-culture system is used, it is possible to culture a first leukocytic population (such as, for example a PBMC or splenocyte) with a leukocytic population from a subject (such as, for example a PBMC or splenocyte). It is also possible to culture a first leukocytic relatively homogenous cell population (such as, for example, a T cell population) with a leukocytic population from a subject (such as, for example a PBMC or splenocyte). It is also contemplated to culture a first leukocytic population (such as, for example a PBMC or splenocyte) with a leukocytic relatively homogenous population of cells from the subject (such as, for example, a T cell population). It is further contemplated to culture a first leukocytic relatively homogenous cell population (such as, for example, a T cell population) with a leukocytic relatively homogenous population of cells from the subject (such as, for example, a T cell population). In some embodiments, the first leukocyte is cultured in a vessel which does allow physical contact with the leukocyte from the subject.

Usually, the cultured cellular preparation is obtained at least 24 hours after the initial contact between the first leukocyte and the leukocyte from the subject. In some embodiment, the cultured cellular preparation is obtained at least 48 hours or at least 72 hours after the initial contact between the first leukocyte and the leukocyte from the subject. In an embodiment, the cultured cellular preparation can be obtained after at least 24 hours of incubating a first leukocyte (for example grafted with a 20 kDa PEG at a density of at 1.0 mM) with the leukocyte from the subject. When the incubation takes place in a 24-well plate, the concentration of each leukocyte population can be at least $1 \times 10^6$ cells.

In yet a further optional embodiment, to obtain the cellular preparation, a polymer-modified second leukocyte can be placed in a cell culture with the a third leukocyte. After the second and third leukocytes have been cultured for a time sufficient to allow pro-tolerogenic allo-recognition, the supernatant of this cell culture can be administered to the subject in need thereof. The supernatant can be modified (e.g. filtered) to remove the second and/or third leukocyte. However, no specific size fractionation or enrichment of specific fractions is applied to the cell culture supernatant prior to administering it to the subject. When the second and third leukocytes are cultured in the same medium (or in the same culture system), one of the two cell populations is inhibited/limited from proliferating (as long as the other cell populations remains capable of proliferating). For example, the modified second leukocyte can be inhibited/limited from proliferating prior to its co-culture with the third leukocyte. Alternatively, the third leukocyte can be inhibited/limited from proliferating prior to its co-culture with the modified second leukocyte. In the co-culture systems, it is important that at least one of the two cell populations be able to proliferate and be considered viable. In an optional embodiment, the second and/or third leukocyte can be expanded and/or differentiated in vitro (from naïve to Treg) prior to or during co-culture.

As indicated above, in the cell culture system, the second leukocyte is allogeneic to the third leukocyte. In some embodiments, the second leukocyte can be allogeneic to the subject and to third leukocyte. Alternatively, the second leukocyte can be xenogeneic to the subject and/or to the third leukocyte. Optionally, one of the second or third leukocyte can be syngeneic or derived from the subject.

Usually, the cultured cellular preparation is obtained at least 24 hours after the initial contact between the second leukocyte and the third leukocyte. In some embodiment, the cultured cellular preparation is obtained at least 48 hours or at least 72 hours after the initial contact between the second leukocyte and the third leukocyte. In an embodiment, the cultured cellular preparation can be obtained after at least 24 hours of incubating a second leukocyte (for example grafted with a 20 kDa PEG at a density of at 1.0 mM) with the third leukocyte. When the incubation takes place in a 24-well plate, the concentration of each leukocyte population can be at least $1 \times 10^6$ cells.

In other embodiments, to provide the cellular preparations, a conditioned blood can be used. The conditioned blood can be obtained by administering a first leukocyte, a first leukocyte population or a first leukocytic relatively homogeneous population (e.g. all modified with the low-immunogenic polymer and all refrained from proliferating) to the test subject (usually an animal, such as a mouse). The blood is recuperated from the test subject after a time sufficient to induce in the transfused test subject a state of anergy or tolerance. It is important that the first leukocyte be administered to an immune competent test subject and that the blood or blood fraction be obtained at a later a time sufficient to provide a conditioned blood. The test subject is a subject being immune competent and having a Treg/pro-inflammatory T cell ratio which is substantially similar to age- and sex-matched healthy subjects. As used herein, the conditioned blood refers to physical components present in the blood and obtained by administering the first leukocyte to the immune competent test subject and having the pro-tolerogenic properties described herein. It is recognized by those skilled in the art that the conditioned blood may be obtained more rapidly by increasing the amount of leukocytes being administered or administering more than once (for example one, twice or thrice) the modified leukocyte. Usually, the conditioned blood is obtained at least one day after the administration of the first leukocyte. In some embodiment, the conditioned blood is obtained at least 2, 3, 4, 5, 6, 7 or 8 days after the administration of the first leukocyte. In an embodiment, the conditioned blood can be obtained by administering at least $5 \times 10^6$ polymer-modified leukocytes (for example grafted with at least 1.0 mM of 20 kDa PEG) to the test subject (e.g. a mice) and recuperating the plasma five days later. In some embodiment, the conditioned blood can be obtained by administering at least $20 \times 10^6$ polymer-modified leukocytes. Methods for obtaining the blood or its fractions (such as serum or plasma) are known to those in the art and usually involve centrifugation and cell lysis.

Once the cellular preparations have been obtained, they can be formulated for administration to the subject. The formulation step can comprise admixing the cellular preparation, conditioned supernatant/serum obtained (at a therapeutically effective dose) with pharmaceutically acceptable diluents, preservatives, solubilizers, emulsifiers, and/or carriers. The formulations are preferably in a liquid injectable form and can include diluents of various buffer content (e.g., Tris-HCl, acetate, phosphate), pH and ionic strength, additives such as albumin or gelatin to prevent absorption to surfaces. The formulations can comprise pharmaceutically acceptable solubilizing agents (e.g., glycerol, polyethylene glycerol), anti-oxidants (e.g., ascorbic acid, sodium metabisulfite), preservatives (e.g., thimerosal, benzyl alcohol, parabens), bulking substances or tonicity modifiers (e.g., lactose, mannitol).

In addition, if the cellular preparations are destined to be used to prevent or limit an excessive immune reaction triggered by a vaccine, they can be formulated for administration with the vaccine. The cellular preparation or the conditioned serum/supernatant can be formulated for simultaneous administration with the vaccine by admixing the vaccine with the cellular preparation or the conditioned serum/supernatant. Alternatively, the cellular preparation or the conditioned serum/supernatant can be formulated for administration prior to or after the vaccine, for example in a formulation that is physically distinct from the vaccine.

Further, if the cellular preparations are destined to be used to prevent or limit an excessive immune reaction triggered by a transplant, they can be formulated for administration prior to the transplantation. The cellular preparations can be formulated for simultaneous administration with the transplant. Alternatively, the cellular preparations can be formulated for administration prior to or after the transplant.

The present invention will be more readily understood by referring to the following examples which are given to illustrate the invention rather than to limit its scope.

Example I—Material and Methods

Human PBMC and Dendritic Cell Preparation.

Human whole blood was collected in heparinized vacutainer blood collection tubes (BD, Franklin Lakes, N.J.) from healthy volunteer donors following informed consent. PBMC were isolated from diluted whole blood using FicollePaque PREMIUM™ (GE Healthcare Bio-Sciences Corp, Piscataway, N.J.) as per the product instructions. The PBMC layer was washed twice with 1× Hank's Balanced Salt Solution (HBSS; without $CaCl_2$ and $MgSO_4$; Invitrogen by Life Technologies, Carlsbad, Calif.) and resuspended in the appropriate media as needed for mixed lymphocyte reactions and flow cytometric analysis of Treg and Th17 phenotypes. Dendritic cells (DC) were prepared from isolated PBMC as described by O'Neill and Bhardwaj (O'Neill et al., 2005). Briefly, freshly isolated PBMC were overlaid on Petri dishes for 3 h in AIM V serum free culture medium (Invitrogen, Carlsbad, Calif.). Non-adherent cells were gently washed off the plate. The adherent cells (monocyte rich cells) were treated with IL-4 and GM-CSF (50 and 100 ng/mL respectively; R&D Systems, Minneapolis, Minn.) in AIM V medium. Cells were again treated with IL-4 and GM-CSF on days 2 and 5. On day 6, cells were centrifuged and resuspended in fresh media supplemented with DC maturation factors (TNF-α, IL-1β, IL-6; R&D Systems, Minneapolis, Minn.) and prostaglandin E2 (Sigma Aldrich, St. Louis, Mo.). The mature DC-like cells were harvested on day 7 and CD80, CD83, CD86 and HLA-DR expressions were determined to confirm DC maturation via flow cytometry (FACSCalibur™ Flow Cytometer, BD Biosciences, San Jose, Calif.).

Murine Splenocyte and Tissue Harvesting.

All murine studies were done in accordance with the Canadian Council of Animal Care and the University of British Columbia Animal Care Committee guidelines and were conducted within the Centre for Disease Modeling at the University of British Columbia. Murine donor cells used for the in vivo donation and in vitro studies were euthanized by $CO_2$. Three allogeneic strains of mice were utilized for syngeneic and allogeneic in vitro and in vivo challenge: Balb/c, $H-2^d$; C57Bl/6, $H-2^b$; and C3H, $H-2^k$. Murine spleens, brachial lymph nodes, and peripheral blood were collected at the indicated days. Mouse spleens and brachial lymph nodes were dissected and placed into cold phosphate buffered saline (PBS; 1.9 mM $NaH_2PO_4$, 8.1 mM $Na_2HPO_4$, and 154 mM NaCl, pH 7.3) containing 0.2% bovine serum albumin (BSA; Sigma Aldrich, St. Louis, Mo.) and kept on ice until ready to process. Whole blood was collected in heparinized tubes via cardiac puncture. Murine donor splenocytes were prepared from freshly harvested syngeneic or allogeneic spleens via homogenization into a cell suspension in PBS (0.2% BSA) using the frosted end of two microscope slides. The resultant cell suspension was spun down at 500×g. The splenocyte pellet was resuspended in 1 mL of 1× BD Pharm LYSE™ lysing buffer (BD Biosciences, San Diego, Calif.) and incubated for 1 min at room temperature. Lymph node cells were harvested via tissue homogenization as described above, washed twice and resuspended in PBS (0.2% BSA) for flow cytometric analysis of Th17, Treg and murine haplotype. Recipient peripheral blood lymphocytes were prepared via lysis of the red cells (BD Pharm Lyse lysing buffer; BD Biosciences, San Diego, Calif.) at 1× concentration, followed by washing (1×) and resuspension in PBS (0.2% BSA) for flow analysis of Th17, Treg and murine haplotype.

mPEG Modification (PEGylation) of PBMCs and Splenocytes.

Human PBMC and murine splenocytes were derivatized using methoxypoly(-ethylene glycol) succinimidyl valerate (mPEG-SVA; Laysan Bio Inc. Arab, Ala.) with a molecular weight of 5 or 20 kDa as previously described (Scott et al., 1997; Murad et al, 1999A; Chen et al., 2003; Chen et al., 2006; Wang et al. 2011). Grafting concentrations ranged from 0 to 5.0 mM per $4×10^6$ cells/mL. Cells were incubated with the activated mPEG for 60 min at room temperature in isotonic alkaline phosphate buffer (50 mM $K_2HPO_4$ and 105 mM NaCl; pH 8.0), then washed twice with 25 mM HEPES/RPMI 1640 containing 0.01% human albumin. Human PBMC were resuspended in AIM V media at a final cell density of $2.0×10^6$ cells/mL for use in the MLR. Murine splenocytes used for in vivo studies were resuspended in sterile saline at a final cell density of $2.0×10^8$ cells/ml for i.v. injection. To determine if the simple presence of the mPEG polymer itself altered the immune response either in vitro and in vivo, additional studies were done with unactivated polymer incapable of covalent grafting to the cell surface. For these studies, allogeneic human (in vitro studies) or syngeneic and allogeneic murine splenocytes (in vivo studies) were treated with non-covalently bound mPEG (soluble mPEG) under the same reaction conditions described for the covalent grafting studies. For clarity, "soluble mPEG" refers to cells treated with non-covalently grafted polymer while "mPEG-modified" refers to treatment with activated polymer resulting in the covalent grafting of the mPEG to the cell membrane.

In Vitro and In Vivo Cell Proliferation.

Cell proliferation (both in vitro and in vivo) was assessed via flow cytometry using the CELLTRACE™ CFSE (Carboxyfluorescein diacetate, succinimidyl ester) Cell Proliferation Kit (Invitrogen by Life Technologies e Molecular probes, Carlsbad, Calif.). Human and murine cells labeling was done according to the product insert at a final concentration of 2.5 mM CFSE per $2×10^6$ cells total. Donor and recipient cell proliferation was differentially determined by haplotype analysis. In some experiments, cell proliferation was measured by $^3$H-thymidine incorporation. In these experiments, donor splenocytes ($5.12×10^6$ cells per well) were co-incubated in triplicate in 96-well plates at 37° C., 5% $CO_2$ for 3 days. On day 3, all wells were pulsed with $^3$H-thymidine and incubated for 24 h at 37° C., 5% $CO_2$. Cellular DNA was collected on filter mats using a Skatron cell harvester (Suffolk, U.K.) and cellular proliferation was measured by $^3$H-thymidine incorporation.

Mixed Lymphocyte Reaction (MLR)—Control and Conditioned Media.

The effects of polymer grafting (5 kDa SVAmPEG) on allorecognition in vitro were assessed using two-way MLR (Murad et al, 1999A; Chen et al., 2003; Chen et al., 2006). PBMC from two MHC-disparate human donors were label with CFSE as described. Each MLR reaction well contained a total of $1×10^6$ cells (single donor for resting or mitogen stimulation or equal numbers for disparate donors for MLR). Cells were plated in multiwell flat-bottom 24-well tissue culture plates (BD Biosciences, Discovery Labware, Bedford, Mass.). PBMC proliferation, cytokine secretion, as well as Treg and Th17 phenotyping was done at days 10 and 14. For flow cytometric analysis, the harvested cells were resuspended in PBS (0.1% BSA). While time course studies (Days 4, 7, 10 and 14) were done, the presented studies show days 10 and 14. These extended studies are, in fact, the most stringent test of the immunomodulatory effects of the grafted polymer as membrane remodeling over this time could have resulted in a latter onset of proliferation. To investigate in vitro whether polymer grafting to allogeneic PBMC gave rise to tolerance or anergy, secondary)(2°) MLR studies were conducted using conditioned media. Conditioned media from a primary)(1°) 2 way-MLR was collected at 72 h for conducting a secondary)(2°) MLR as schematically shown in FIG. 1. Conditioned media from the 1° MLR included: A1) resting unmodified PBMC; B2) resting PEGylated PBMC; C3) two-way MLR; and D4) two-way mPEG-MLR. The 2° MLR utilized freshly prepared MHC-disparate donors (either the same as or different from) the initial plate and plated as described above. As shown in FIG. 1, the 2° MLR samples included: A) resting PBMC; B) two-way MLR; P) mitogen stimulation; D) two-way mPEG-MLR. For these studies, PBMC were derivatized using 1 mM 5 kDa SVAmPEG. Mitogen stimulation (PHA-P; Sigma-Aldrich, St. Louis, Mo.) of donor PBMC in the secondary plates was done to assess the proliferation potential and viability of cells incubated in the conditioned media. Human PBMC were challenged with 2 mg/ml per $1×10^6$ cells of PHA-P. All plates were incubated at 37° C. (5% $CO_2$). Following 13 days of incubation (37° C., 5% $CO_2$), the cell culture supernatants were collected and cells were harvested from the 2° MLR plates. Cell proliferation was measured via CSFE-dilution of $CD3^+CD4^+$ lymphocytes by flow cytometry.

Immunophenotyping by Flow Cytometry.

The T lymphocytes populations (double positive for $CD3^+$ and $CD4^+$) in both the in vitro and in vivo studies were measured by flow cytometry using fluorescently labeled CD3 and CD4 monoclonal antibodies (BD Pharmingen, San Diego, Calif.). Human and mouse Regulatory T lymphocytes (Treg) were $CD3^+/CD4^+$ and $FoxP3^+$ (transcription factor) while inflammatory Th17 lymphocytes cells were $CD3^+/CD4^+$ and $IL-17^+$ (cytokine) as measured per the BD Treg/Th17 Phenotyping Kit (BD Pharmingen, San Diego, Calif.). After the staining, the cells ($1\times10^6$ cells total) were washed and resuspended in PBS (0.1% BSA) prior to flow acquisition. Isotype controls were also used to determine background fluorescence. All samples were acquired using the FACSCalibur™ flow cytometer (BD Biosciences, San Jose, Calif.) and CellQuest Pro™ software for both acquisition and analysis.

Cytokine Quantitation.

Cell culture supernatants were collected from the 1° two-way MLR plate and stored at −80° C. prior to analysis. Conditioned media aliquots from a minimum of four independent experiments were used for quantification of supernatant cytokine levels using the BD Cytometric Bead Array (CBA) system (BD Biosciences, San Diego, Calif.) for flow cytometry. The CBA system is a multiplexed bead based immunoassay used to quantitate multiple cytokine levels in a single sample simultaneously by fluorescence-based emission and flow cytometry. Cytokine measured included: IFNγ, TNF-α, IL-10, IL-5, IL-4, and IL-2 using the BD Human Th1/Th2 Cytokine Kit I™. The IL-6 and IL-17A levels were measured using the BD CBA Human Soluble Protein Flex Set™. Both assays were performed following the manufacturer's product instruction manual. Briefly, cell culture supernatants of resting unmodified PBMC, unmodified MLR, PEGylated (5 kDa SVAmPEG; one donor) resting PBMC, PEGylated MLR, and mitogen (PHA) stimulated PBMC were incubated at room temperature in the dark with a mixture of each cytokine antibody-conjugated capture bead and the PE-conjugated detection antibody. Following the incubation, the samples were washed and acquired using a FACSCalibur™ flow cytometer and analyzed using CellQuest Pro™ software. Cytokine protein levels were determined using the BD Cytometric Bead Array™ and FCAP Array™ analysis software (BD Biosicences, San Diego, Calif. and Soft Flow Inc, St. Louis Park, Minn.).

In Vivo Murine Studies.

To investigate whether mPEG grafting to leukocytes would have systemic in vivo effects, a murine adoptive transfer system was employed using three genetically different strains: Balb/c, $H-2^d$; C57Bl/6, $H-2^b$; and C3H, $H-2^k$ (Chen et al., 2003; Chen et al., 2006). All mice (donors and recipients) were 9-11 weeks old. Donor splenocytes were prepared and CSFE labeled as described. control and mPEG-grafted (1 mM, 20 kDa SVAmPEG) syngeneic or allogeneic cells ($20\times10^6$ splenocytes) were transfused intravenously (i.v.) via the tail vein into recipient animals. BALB/c and C57BL/6 mice injected with sterile saline served as control animals. Animals were euthanized by $CO_2$ at predetermined intervals at which time blood, brachial lymph nodes and spleen were collected and processed for Th17/Treg phenotyping analysis and splenocyte proliferation studies by flow cytometry. Donor cell engraftment and proliferation were assessed via flow cytometry using murine haplotype ($H-2K^b$ vs. $H-2K^d$) analysis. To determine the persistence of the immunomodulation, mice were rechallenged (2° challenge) 30 days after the initial transfer of allogeneic or mPEGallogeneic splenocytes with unmodified allogeneic cells. At 5 days post 2° challenge, Treg and Th17 phenotyping of murine splenocytes isolated from the spleen, lymph node and peripheral blood was again assessed via flow cytometry.

Statistical Analysis.

Data analysis was conducted using SPSS™ (v12) statistical software (Statistical Products and Services Solutions, Chicago, Ill., USA). For significance, a minimum p value of <0.05 was used. For comparison of three or more means, a one-way analysis of variance (ANOVA) was performed. When significant differences were found, a post-hoc Tukey test was used for pair-wise comparison of means. When only two means were compared, student-t tests were performed.

Example II—In Vitro and In Vivo Immunomodulation

The material and methods used in this example are provided in Example I.

Figure 2:
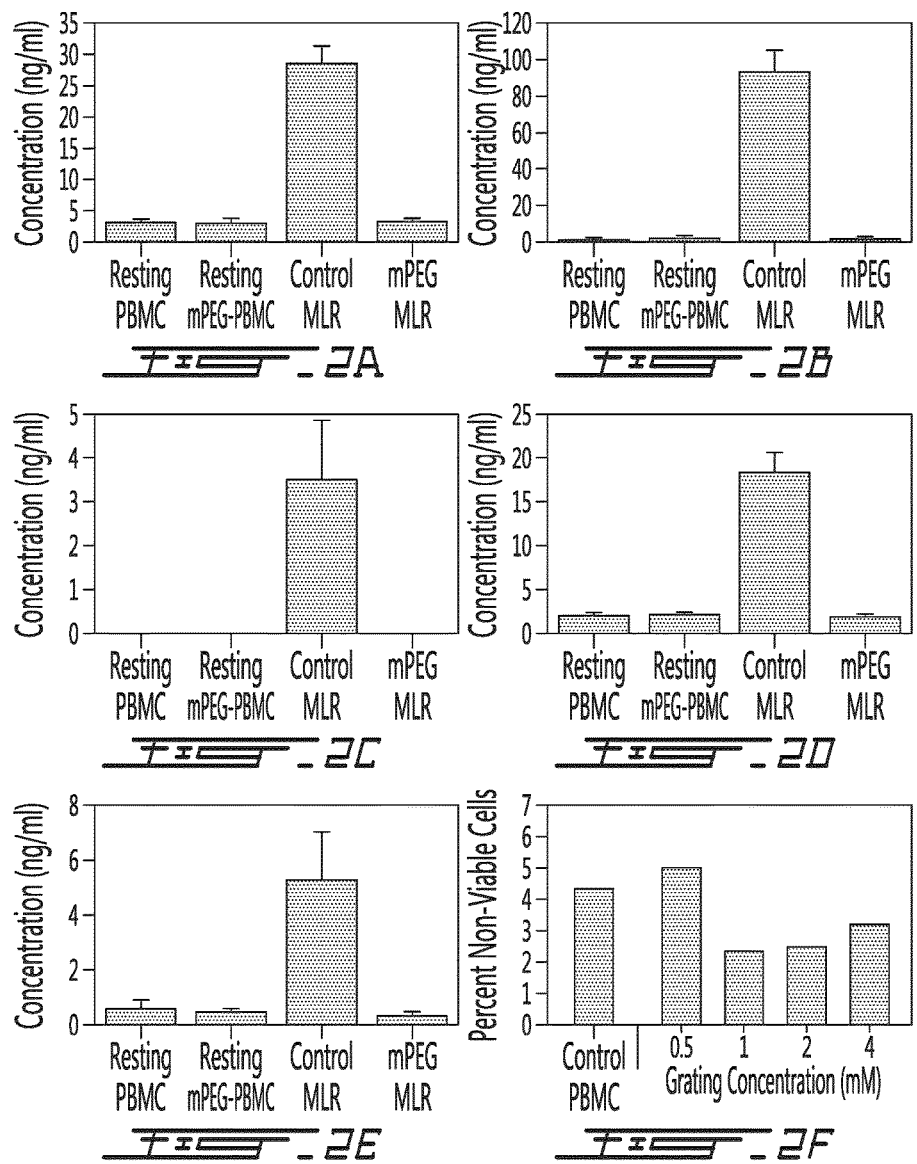
FIG. 2 shows 1° mixed lymphocyte reaction (MLR) results. Primary)(1° media cytokine levels at 72 h. IL-2 (A), IFN-γ (B) IL-17A (C), TNF-α (D) and IL-6 (E), levels are significantly reduced in the PEGylated two-way MLR utilizing modified and unmodified PBMC populations from HLA disparate individuals. The cytokine profile (ng/mL) was analyzed using the BD cytometric bead array. Values shown are the mean±SD of a minimum of four independent experiments. Percent non-viable cells within the control and PEGylated (SVAmPEG; 5 kDa) resting PBMC was assessed by propidium iodine exclusion (F).

To determine the effects of polymer modification on the immune response, initial in vitro experiments examined the cytokine burst characterizing control and polymer modified MLR. The polymer-mediated immune modulation of human PBMC resulted in significant changes in the cytokine profile of the conditioned media obtained from the 1° MLR plate (FIGS. 1 and 2). As shown in FIG. 2, control MLRs yielded elevated concentrations of IL-2, IFN-γ, IL-17A, TNF-α and IL-6 relative to resting unmodified or PEGylated PBMC. In contrast to the control MLR, the mPEG-MLR (one donor population PEGylated with 1 mM 5 kDa SVA-mPEG) resulted in the virtually complete inhibition (p<0.001) of secretion for the proinflammatory cytokines examined. However, IL-10 was preferentially elevated in the mPEG-MLR. In the conditioned media, IL-10 levels were 2.01±1.26, 8.90±2.10, 1.69±0.64 and 1.33±0.73 ng/ml for the resting PBMC, mPEG-MLR, resting mPEG-PBMC and Control MLR, respectively. As noted, in the mPEG-MLR, IL-10 levels were significantly (p<0.01) increased suggesting the induction of an immunosuppressive state. Importantly, this cytokine quiescent state was not due to loss of cell viability as evidenced by the very low levels of non-viable cells detected following 72 h incubation (FIG. 2).

Figure 3:
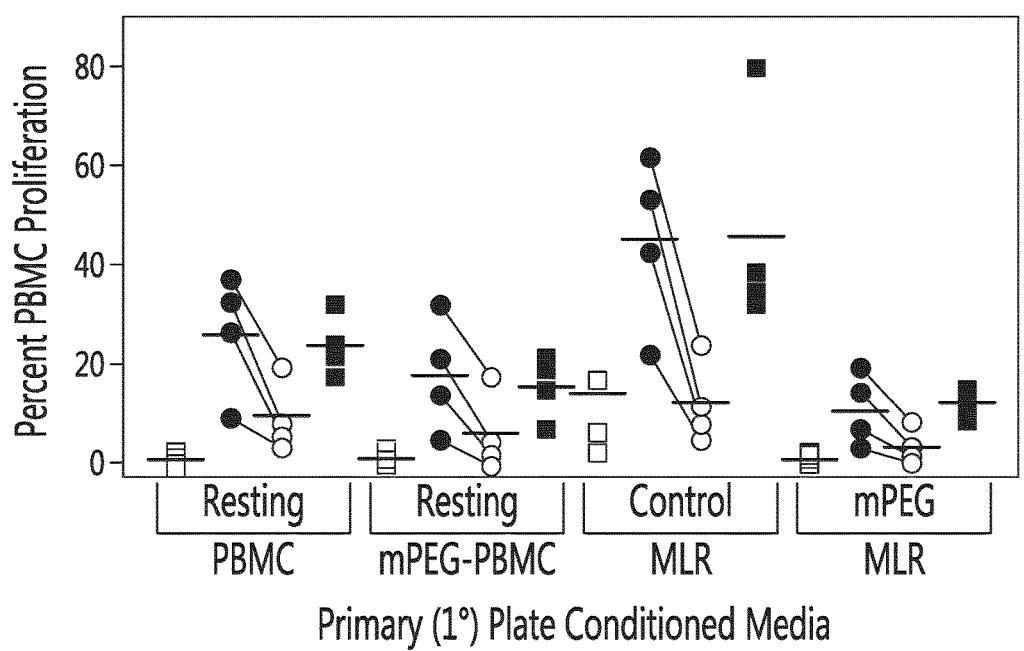
FIG. 3 shows 2° mixed lymphocyte reaction (MLR) results. Shown is the proliferation index (percent PBMC proliferation) of the secondary MLR (□ resting PBMC, ● control MLR, ○ mPEG MLR, ■ PHA stimulation) that were conducted in the indicated (x-axis) conditioned media. As shown, relative to all other conditioned media, the media from the 1° plate control MLR demonstrated a significant (p<0.01) pro-proliferative effect in the 2° MLR. This effect was noted on even resting PBMC and PHA-stimulated cells. In contrast, the 1° conditioned media from the mPEG-MLR demonstrated a significant anti-proliferative effect in the 2° MLR. As noted by the lines connecting paired experiments, PEGylation of one donor population resulted in reduced proliferation in all conditioned media experiments. No significant differences were noted between fresh media in a parallel secondary plate and the resting PBMC conditioned media. Shown are the individual results of four independent experiments and the mean (line). PEGylated cells were modified with 1 mM SVAmPEG (5 kDa).

The conditioned media produced from the initial 72 h MLR exerted a significant effect on the 2° MLR as demonstrated in FIG. 3. While the 1° media from resting PBMC showed no significant effect on the 2° MLR, the media from the 1° Control MLR demonstrated a significant (p<0.01) pro-proliferative effect in the 2° MLR. As shown, the mean proliferation index of the 2° MLR increased from 26.05±12.47 to 44.72±17.13 in the presence of conditioned media from the 1° Control MLR. The pro-inflammatory effect of the 1° MLR media was noted on even the resting PBMC and PHA-stimulated cells. In contrast, the 1° conditioned media from the mPEG-MLR demonstrated a significant (p<0.001) anti-proliferative effect in not only the 2° MLR but also the PHA-stimulated cells. The differential proliferation response between the control and mPEG-MLR conditions for matching experiments is noted by the lines connecting paired experiments. While not shown, soluble mPEG (5 kDa) had no effect on cytokine levels in the 1° conditioned media nor on the proliferation of PBMC mediated by allorecognition (control MLR) or by mitogen (PHA) stimulation.

Figure 4A:
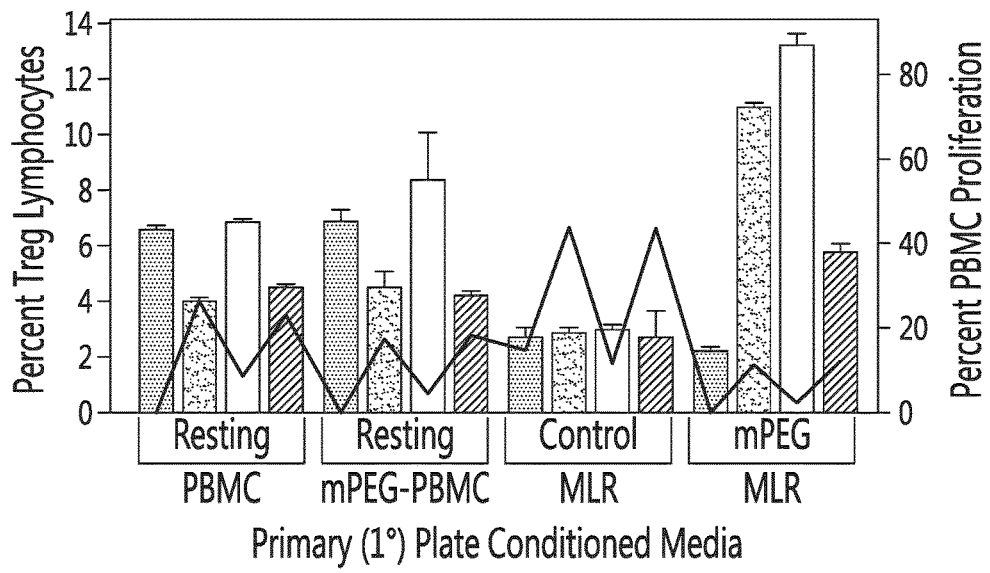
FIG. 4 illustrates the effects of the various conditioned media on the levels of Treg and Th17. PEGylation of human lymphocytes resulted in a significant in vitro immunomodulatory effects as noted by changes in the percentage of Treg (A) and Th17 (B) T cell populations (dark gray column→resting PBMC; light grey column→control MLR; white column→mPEG MLR; hatched column→PHA stimulation). Results are also provided for percent PBMC proliferation (line) for 2° plates having received 1° conditioned media (defined in x-axis). As shown, the 1° media from the mPEG-MLR favored production of Treg cells and a decreased population of Th17 lymphocytes. In contrast, the 1° media from the control MLR enhanced Th17 cell production and greatly inhibited Treg levels. The relative ratio of Th17:Treg was highly correlated with lymphocyte proliferation as denoted by the right y-axis and the embedded line graph. The high levels of Tregs in both the resting mPEG-PBMC and in mPEG-MLR correlated with low levels of proliferation. In contrast, an increased level of Th17 cells was associated with the 1° media from the control MLR and PHA stimulation. PEGylated cells were modified with 1 mM SVAmPEG (5 kDa). Percent PBMC proliferation is provided in the right y-axis and by line on both panels.
Figure 4B:
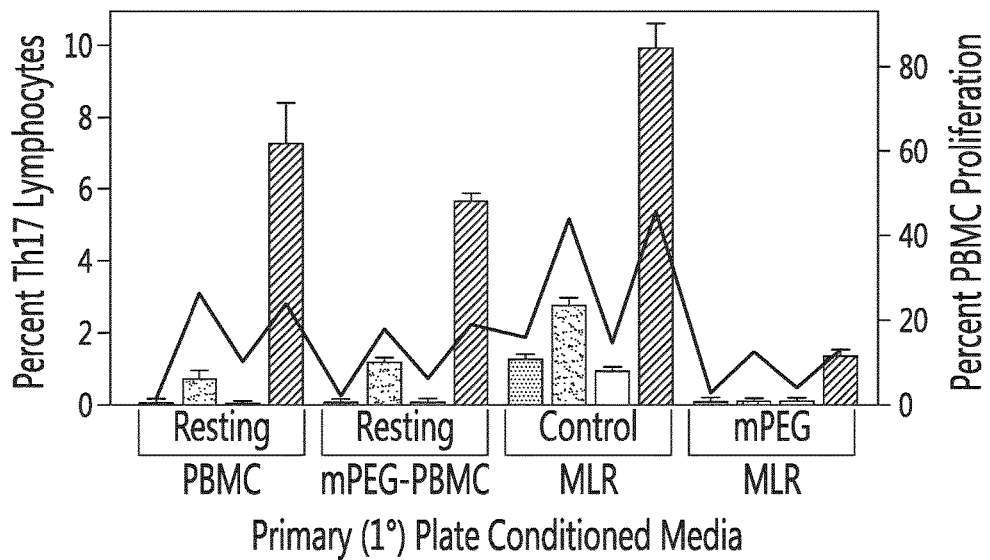

Furthermore, as shown in FIG. 4, the proliferation index was positively correlated with an increased population of Th17 T cells and inversely correlated with Treg lymphocytes numbers. As demonstrated, the 1° conditioned media from the control MLR yielded elevated levels of Th17 cells and decreased levels of Treg lymphocytes. In comparison, the 1° media from the mPEG-MLR resulted in significantly elevated (p<0.001) levels of Treg cells and a virtually non-existent population of Th17 lymphocytes. The source of the conditioned media also impacted the efficacy of PHA stimulation. As shown, conditioned media from the mPEG-MLR significantly inhibited mitogen proliferation while the control MLR conditioned media significantly enhanced proliferation relative to both media from resting PBMC (p<0.01) and resting mPEG-PBMC (p<0.001).

Hence, the in vitro experiments demonstrated that covalent grafting mPEG to human PBMC resulted in an immunomodulatory effect governed in part by changes in the Th17 and Treg populations. Moreover, these conditioned media experiments demonstrated that this immunomodulatory effect arises from soluble factors that might be able to induce a systemic effect in vivo. To determine if similar effects would be observed in vivo, a murine splenocyte adoptive transfer model was utilized. As demonstrated in FIG. 5, PEGylated donor splenocytes resulted in a significant in vivo immunomodulatory effect giving rise to elevated levels of Treg lymphocytes within the spleen, brachial lymph node, and peripheral blood. As noted, in all three tissues, a significant (p<0.001 at 120 h) time-dependent increase in Treg lymphocytes over that observed in naïve mice was noted in mice receiving mPEG-modified allogeneic donor cells. In stark contrast, a significant (p<0.001) decrease in Tregs 48 h post-injection relative to naïve mice) is noted in mice transfused with unmodified allogeneic splenocytes. The absolute difference between the unmodified (control) and PEGylated splenocytes, shown by the stippled area, demonstrates the true magnitude of the differential impact of donor cell PEGylation. Importantly, as noted at 120 h, transfusion of soluble mPEG, syngeneic cells or mPEG-syngeneic cells had no significant effect on the Treg lymphocyte population.

As foreshadowed by our in vitro human PBMC findings (Example II), murine Th17 lymphocyte levels were influenced by the PEGylation state of the allogeneic donor cells (FIG. 6). While unmodified allogeneic murine donor cells resulted in a significant (p<0.001), time-dependent, increase in the Th17 cell population in the spleen, brachial lymph node and peripheral blood, the covalent grafting of mPEG to the membrane of the donor splenocytes resulted in the complete abrogation of the increase. Indeed, the Th17 population remained at resting levels. The absolute difference between the unmodified and mPEG-modified donor cells is denoted by the stippled area. As with the Treg population, transfusion of soluble mPEG, syngeneic cells or mPEG-syngeneic cells had no significant effect on the Th17 lymphocyte population at 120 h.

As also shown on FIG. 7, normal mice have significantly higher levels of Tregs (Spleen ~10% total CD4+ T cells) relative to Th17 T Cells (Spleen ~0.05% total CD4+ T cells). Further, treatment with unmodified allogeneic cells results in production of Th17 cells and loss of Tregs. In contrast, polymer modified allogeneic cells maintain (even increase) Tregs and prevents Th17 production.

As might be anticipated, the mPEG-allogeneic splenocyte mediated increase in Treg cells in the peripheral blood samples occurred later in the studied time course (96 h) compared to either of the lymphatic tissues (spleen and lymph nodes; 48 h). This clearly suggests that T cell proliferation initially occurred within the lymphatic tissues and secondarily migrated into the peripheral blood. A similar time dependency was noted with the Th17 proliferation induced by the unmodified splenocyte populations. Proliferation initially occurred within lymphatic tissue within ~48 h and only appeared within the peripheral blood after ~96 h.

Of importance was the observation that the immunomodulatory effects of the PEGylated splenocytes were long lived and prevented subsequent changes in Treg and Th17 levels consequent to rechallenge with unmodified allogeneic cells. As shown in FIG. 8, 30 days post transfusion with polymer modified splenocytes, Treg levels remain significantly elevated and are similar to levels recorded at 120 h post challenge. In contrast, Th17 levels remained similar to or decreased from that observed in naïve mice at day 30. Of even more interest, a secondary adoptive transfer of unmodified allogeneic splenocytes (30 days post 1° challenge; measured at 120 h) to mice previously treated with PEGylated allogeneic showed no significant decrease in Treg cells, or increase in Th17 cells, relative to the day 30 levels. This was in direct contrast to that observed in naïve mice (FIG. 5) injected with unmodified allogeneic cells that demonstrated a dramatic decrease in Treg lymphocytes. Indeed, Treg levels remain significantly elevated above that seen in naïve mice and very similar to those levels observed at 5 days post PEGylated splenocytes transfusion.

Figure 9:
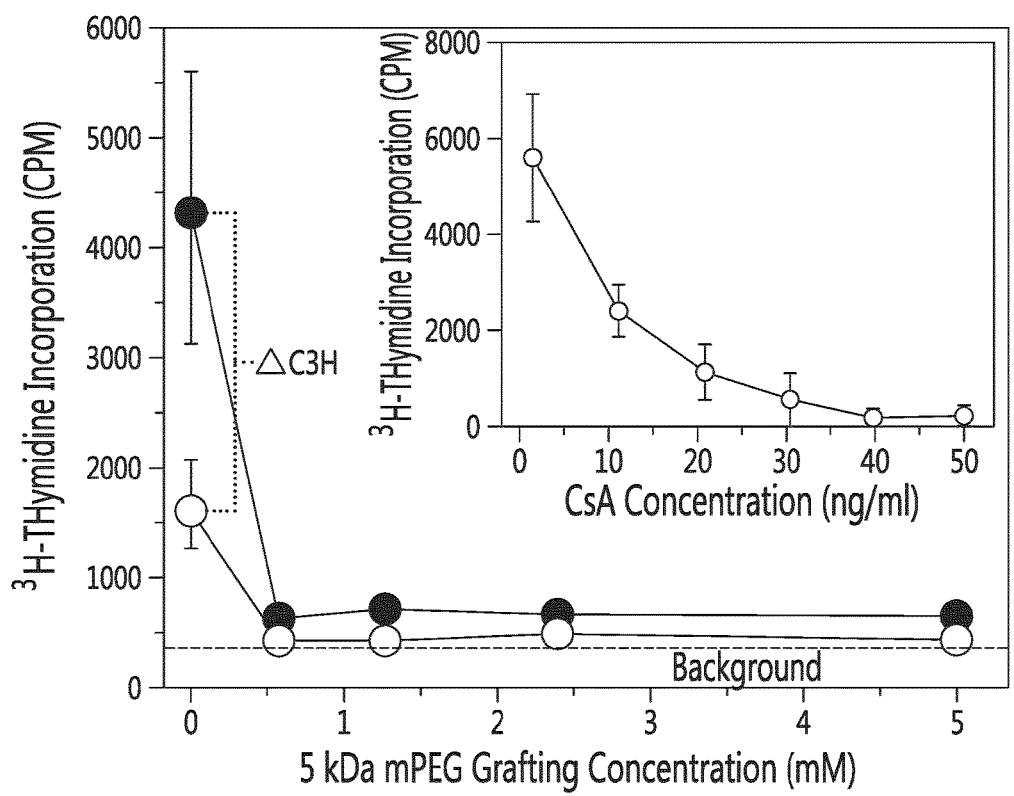
FIG. 9 shows that immunomodulation is not haplotype-specific. Initial one-way MLR (○) was conducted and consisted of C57Bl/6 (H-2b) splenocytes challenged with unmodified or PEGylated irradiated Balb/c (H2-d) splenocytes. Following 48 h of challenge, duplicate samples were challenged with unmodified-non-irradiated C3H (H-2k) splenocytes (two-way MLR or ●). Results are shown as $^3$H-thymidine incorporation in function of polymer (mPEG 5 kDa) grafting concentration (in mM). The addition of the fresh responder cells from a third, H2-disparate mouse strain (C3H), at 48 h did not reverse the attenuation of proliferation in responder cells co-incubated with irradiated, cmPEG-modified Babl/c splenocytes. In contrast, the proliferation in the control (0 mM) MLR was significantly (p<0.001) enhanced by the addition of the C3H splenocytes (ΔC3H). The data shown represented the co-culturing of $5.12 \times 10^6$ C57Bl/6 splenocytes with $5.12 \times 10^6$ irradiated, mPEG-derivitized Balb/c splenocytes. After 48 h of incubation, fresh C3H responder cells were added to duplicate wells. The results were expressed as the average mean±standard deviation of triplicate samples from a representative experiment. PEGylated murine splenocytes were modified with the indicated concentrations (mM) of activated mPEG (5 kDa). For comparative purposes, the anti-proliferative dose-response effect of cyclosporine A (CSA; which induces a pharmacologically-induced anergy) in a one-way murine MLR under the same experimental condition is shown in the insert.

To determine if the observed in vivo murine findings gave rise to a tolerance to a specific H-2 haplotype or a more generalized anergy to allogeneic tissues, in vitro two-way murine MLR studies of three allogeneic splenocyte populations (Balb/c, $H-2^d$; C57Bl/6, $H-2^b$; and C3H, H-2) were done. As demonstrated in FIG. 9, the immunomodulation arising following exposure to polymer-grafted H-2 disparate splenocytes is not specific to the haplotype of the mPEG-modified splenocytes thereby suggestive of an anergic state. As shown, PEGylation of stimulator (i.e., irradiated and incapable of proliferation) splenocytes very effectively attenuated allorecognition and proliferation of the responder cell population within a one-way MLR. Moreover, for comparative purposes, the anti-proliferative dose-response effect of cyclosporine A (CSA; which induces a pharmacologically-induced anergy) in a one-way murine MLR under the same experimental condition is shown. Interestingly, the type of polymer-modified cell is important. Human lymphocytes and murine splenocytes express high levels of "self-antigens" (Human Leukocyte Antigens (HLA) and mouse H-2 proteins). If cells devoid of these highly immunogenic antigens are used in the murine model, no changes in either Tregs or Th17 cells are observed. In mice injected with unmodified allogeneic erythrocytes, Treg levels within the spleen, lymph node and peripheral blood were (respectively): 91.7%, 95.0% and 107.0% of control mouse values. Similarly unchanged, Th17 levels were (respectively): 71.2%, 112.1% and 79.2% of control mouse values. Thus, allogeneic murine RBC do not elicit any significant changes in the systemic levels of either Treg or Th17 lymphocytes. This finding was observed despite some antigenic differences between the RBC in H-2 disparate mice. In support of the low immunogenicity of these genetically different RBC, allogeneic RBC exhibit normal in vivo circulation nor do they elicit a significant immune response. Hence, polymer coupled to a low-immunogenicity allogeneic cell can not induce the immunomodulation noted with the highly immunogenic splenocytes.

Bioengineering of donor cells and/or tissues may provide significant opportunities to attenuate both the recognition and rejection of allogeneic tissues. One polymer-mediated approach to this end is the polymer modification of donor cells via the covalent grafting of mPEG (or other low immunogenicity polymers) to the exterior face of cell membranes. Consequent to membrane derivatization, mPEG-modified allogeneic and xenogeneic cells demonstrated a global, multivalent, attenuation of antigenicity and immunogenicity. This effect arouse in part from charge camouflage and significantly diminished cell:cell (e.g., T cell:APC or T cell:islet cell) and ligand:receptor (e.g., antibody:antigen or CD28:CD80) interactions. The efficacy was dependent on polymer molecular weight (i.e., size) and grafting density.

However, the inhibition of cell:cell and ligand:receptor interactions are a 'local' immunomodulatory event arising from the steric and charge camouflaging effects of the grafted polymer. For the induction of tolerance, a systemic and persistent immunomodulatory effect would be necessary. As demonstrated herein, covalent grafting of mPEG to allogeneic lymphocytes (human PBMC or murine splenocytes) dramatically reduced allorecognition at both the local (cell:cell; MLR) and systemic (in vivo murine models) levels. Importantly, as demonstrated in our in vivo studies, it is not the donor cells that differentiate into Treg or Th17 cells, rather it is the recipients immune system that responds to the control or PEGylated splenocytes and upregulates production of either Th17 (upon challenge with unmodified splenocytes) or Treg (upon challenge with mPEG-splenocytes) populations. This was noted by both the absence of CFSE-staining (only donor cells were stained) and H-2 phenotyping of the Th17 and Treg cell populations.

The observed immunosuppressive state induced by PEGylated lymphocytes is surprisingly long lasting in vivo. As noted in FIG. 8, the elevated levels of Treg lymphocytes noted at day 5 persist to day 30. Moreover, the presence of these Treg (as well as other probable immunological events) prevents a pro-inflammatory response to unmodified allogeneic splenocytes administered at day 25. Indeed, no increase in Th17 lymphocytes is noted in the immunomodulated mice. Moreover, for the systemic tolerance/anergy to occur, the polymer must be grafted to a highly immunogenic cell type (e.g., lymphocyte and/or antigen presenting cells) as less immunogenic cells, such as H-2 disparate erythrocytes, do not alter the immune (Treg/Th17) response. While allogeneic murine erythrocytes do express antigenic differences at the membrane, these cells are only weakly immunogenic eliciting weak IgG responses and typically remaining in the vascular circulation with a near normal half-life. Also of critical importance, induction of both local and systemic immunomodulation requires the covalent grafting of the polymer to the cell, as soluble mPEG±allogeneic cells has no effect on the population dynamics of either Treg or Th17 lymphocytes in vitro or in vivo.

The balance between Treg and Th17 cells has been identified as a key factor that orchestrates the tolerance/inflammation level of human immune system. Regulatory T cells provide suppressor effect and maintain tolerance, while Th17 cells mediate and are indicative of a pro-inflammatory state. Hence, the polymer-mediated modulation of this balance may be clinically useful. Recent findings have shown that cyclosporine, a clinically used immunosuppressive agent, has substantial effects on the Treg/Th17 cell response; though this may be mediated by Th17 cytotoxicity as Treg cells cultured in the presence of rapamycin, but not cyclosporine A, are found to suppress ongoing alloimmune responses. Additionally, mycophenolic acid, another immunosuppressive agent, was found to shift the lymphocyte polarization by inhibiting IL-17 expression in activated PBMC in vitro. Of clinical importance, all of these pharmacologic agents exert significant systemic toxicity and their ongoing use requires substantial monitoring.

Figure 10:
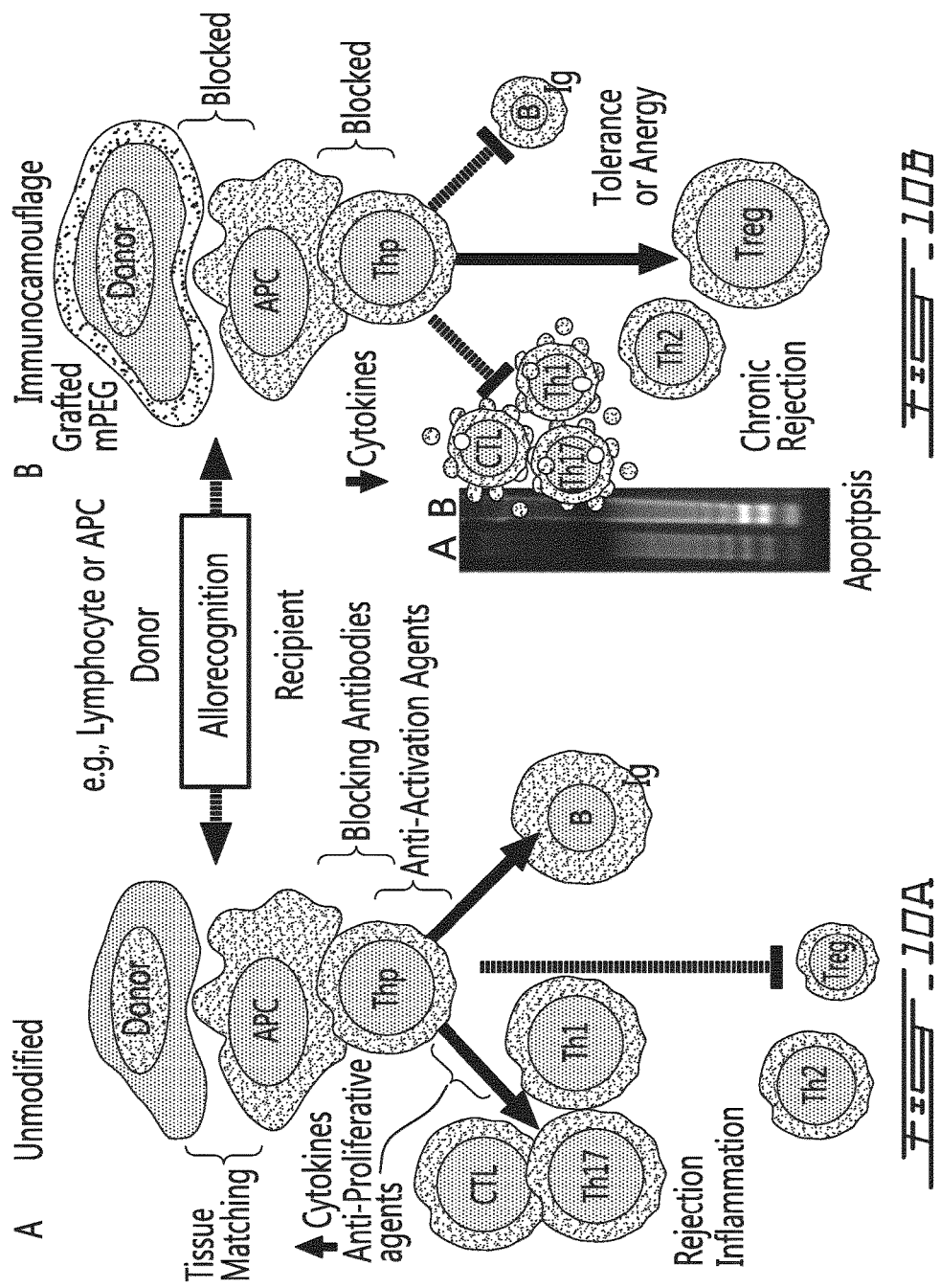
FIG. 10 provides an hypothetical representation of cellular-mediated immune modulation. (A) Current immunomodulation therapy almost exclusively targets the recipient's immune system and does not address the inherent antigenicity and immunogenicity of allogeneic tissues. Response to non-self is in large part mediated by cell-cell interactions between Antigen Presenting Cells (APC; e.g., dendritic cells) and naïve T lymphocytes (Thp). This cell-cell interaction is characterized by adhesion, allorecognition and co-stimulation events. Consequent to allorecognition, cytokine/chemokine burst occurs followed by proliferation of pro-inflammatory T cells (e.g., CTL, Th17, Th1 populations), immunoglobulin production and decreased evidence of regulatory T cells (Treg). Current therapeutic agents are primarily cytotoxic agents preventing T cell activation (e.g., cyclosporine and rapamycin) or T cell proliferation (e.g., methotrexate, corticosteroids, azathiaprine). Additionally some blocking antibodies have been investigated. (B) In contrast, polymer modification of donor PBMC results in loss of appropriate cell-cell interaction leading to loss of the cytokine burst, decreased/absent proliferation, evidence of apoptosis of alloresponsive T cells and increased levels of Regulatory T (Treg) cells that, in aggregate, provides a tolerogenic/anergic state both in vitro and in vivo. Shown with the schematic is a DNA laddering gel of an unmodified MLR (A) and a PEGylated MLR (B) showing enhanced apoptosis consequent to PEGylation. Size of T cell population denotes increase or decrease in number. Size of B cell indicates antibody response.

As evidenced by these results, induction of tolerance or anergy in transfusion and transplantation medicine by the polymer modification of allogeneic leukocytes may provide a less toxic approach than current conventional pharmacologic agents. Current efforts to prevent and/or regulate the consequences of allorecognition involve phenotype matching (ranging from blood group to HLA matching) and the use of immunosuppressive agents (FIG. 10A). While extensive tissue matching (e.g., blood groups, HLA) can dramatically enhance transfusion or transplantation success, the necessity of tissue matching dramatically reduces the potential pool of donor tissues. Even in a tissue as plentiful as blood, extensive non-ABO matching for chronically transfused patients (e.g., sickle cell disease), while considered desirable, is costly and often difficult to achieve due to the scarcity of appropriately matched donor cells. This difficulty is greatly exaggerated with less common tissues and organs (e.g., islets and kidneys).

Thus, pharmacological interventions have been employed to enhance the probability of successful donor tissue engraftment (FIG. 10B). The data presented here suggests that polymer encapsulation "of", or grafting "to", donor tissue may be further enhanced or replaced by a tolerogeneic or anergic approach. Rather, the prechallenge of a potential tissue recipient with PEGylated donor specific (or simply allogeneic; see FIG. 9) PBMC several (~5) days prior to tissue transplantation could be used to induce a tolerogenic state within the recipient as shown in FIG. 10B. Elevated levels of Tregs and the down-regulation of Th17 cells would diminish the risks of both hyper-acute and acute rejection of the donor tissue. There are several substantial advantages for this approach. Primary amongst these are the easy collection of donor specific (or simply allogeneic) PBMC, the ease of PEGylation of the PBMC as well as the ease of administration to the transplant recipient. While a potential risk of lymphocyte transfusions is transfusion associated graft versus host disease (TA-GVHD) in immunosuppressed patients, it was previously demonstrated that PEGylation effectively blocks TA-GVHD in a murine model (Chen et al., 2003; Chen et al., 2006). Moreover, this process could be used in conjunction with irradiated PBMC thus obviating any risk of TAGVHD. Irradiated cells retain their allostimulatory effects and PEGylation similarly inhibits this allorecognition and proliferation.

In summary, polymer modification of allogeneic donor lymphocytes prevents allorecognition at the cell:cell level and also gives rise to systemic immunomodulation. The systemic immunomodulation is evidenced by a significant up-regulation of Treg cells and a significant down-regulation of pro-inflammatory Th17 cells. This immunomodulation is persistent (~30 days) and prevents subsequent pro-inflammatory responses to unmodified allogeneic cells. The polymer effect is dependent upon its covalent grafting to allogeneic cells as soluble PEG itself has no immunomodulatory effects. The clinical use of PEGylated (or other covalently grafted polymers) allogeneic lymphocytes to pre-challenge tissue recipients 5 days or more to transplantation may be useful in inducing a tolerogenic state and preventing acute rejection and/or enhancing tissue engraftment.

Example III—In Vivo Immunomodulation in Nod Mice

Some of the material and methods referred to in this example are provided in Example I.

Figure 11:
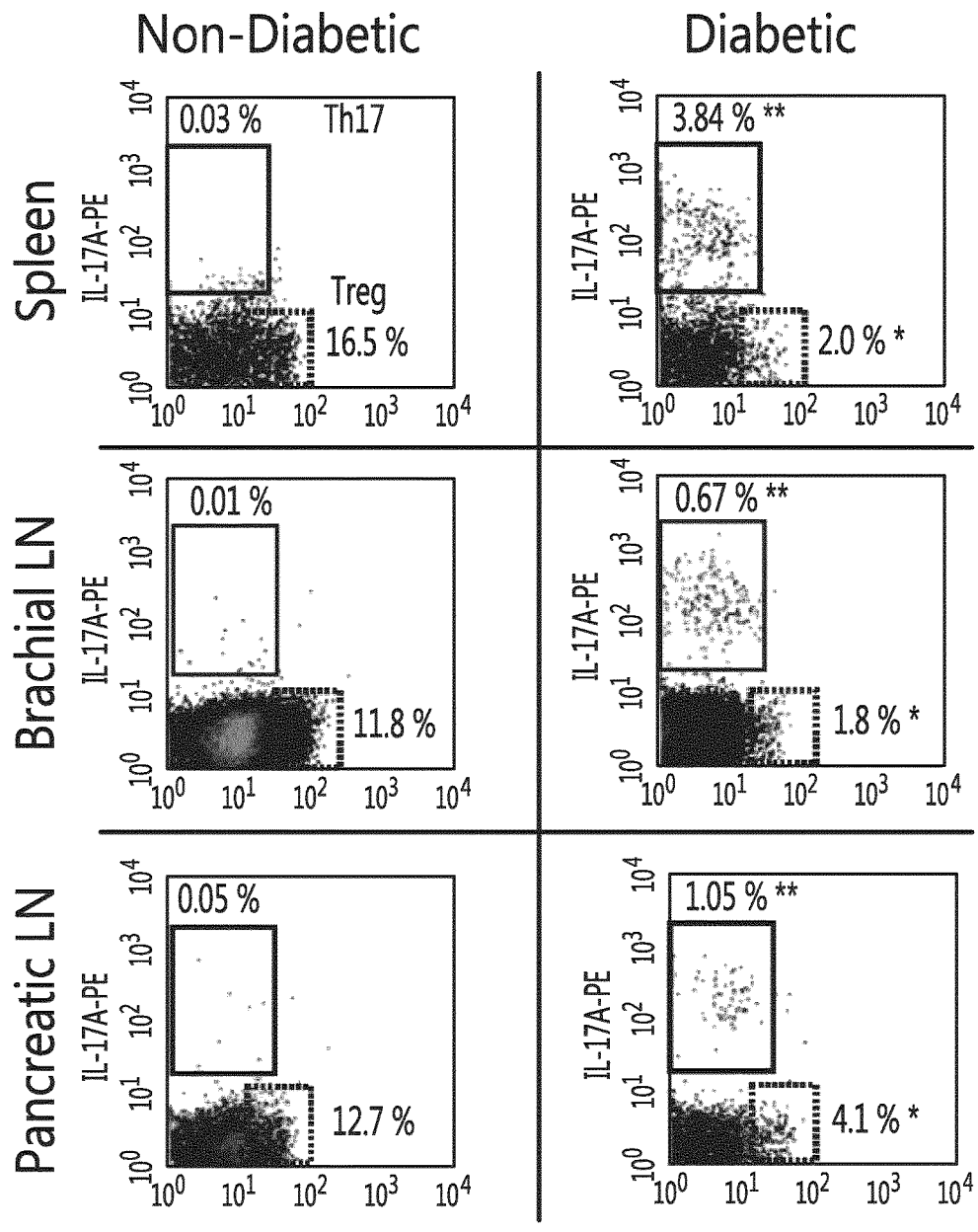
FIG. 11 illustrates significant changes in the levels of Th17 and Treg lymphocytes are noted in the spleen (upper panels), brachial lymph node (middle panels) and pancreatic lymph nodes (lower panels) upon conversion of NOD mice from non-diabetic (left panels) to diabetic (right panels). These changes are characterized by dramatically increased Th17 (in the spleen, from 0.03 to 3.84%; in the brachial lymph node from 0.01% to 0.67%; in the pancreatic lymph node from 0.05% to 1.05%) and significantly decreased Treg (in the spleen, from 16.5% to 2.0%; in the brachial lymph node from 11.8% to 1.8% and in the pancreatic lymph node, from 12.7% to 4.1%) lymphocytes. Tregs: *, $p<0.001$ from non-diabetic NOD mice. Th17: ** $p<0.001$ from non-diabetic NOD mice.

In the NOD mice, autoimmune destruction of the pancreatic islets occurs within approximately 16 weeks and was confirmed with elevated blood glucose measures. The lymphocytes from pre-diabetic and diabetic animals has been obtained from the spleen, the brachial lymph node and the pancreatic lymph node. These lymphocytes have been submitted to flow cytometry using anti-IL-17A (PE) and anti-FoxP3 (Alexa 697) antibodies. As shown in FIG. 11, significant changes in the levels of Th17 and Treg lymphocytes are noted in the spleen, brachial lymph node and pancreatic lymph nodes upon conversion of NOD mice from non-diabetic to diabetic state. These changes are characterized by dramatically increased Th17 (top numbers in each panels) and significantly decreased Treg (lower numbers in each panels) lymphocytes. Tregs: *, p<0.001 from non-diabetic NOD mice. Th17: ** p<0.001 from non-diabetic NOD mice.

The NOD mice (8 to 10 week-old) have been treated with allogeneic leukocytes (as described in Example I) and mPEG-allogeneic leukocyte (as described in Example I) and were compared to untreated control mice (naïve or NOD in Table 1). Th17 levels have been measured in various tissues (as described in Example I). Peripheral blood samples of the groups were pooled for analysis, all other samples were measured individually. Five male NOD mice per group were used. The results are shown in Table 1 provided below.

TABLE 1

Treatment of NOD mice with unmodified or mPEG-modified allogeneic cells. Unmodified cells results in a potent inflammatory state as showby increased Th17 cells. In contrast, administration of mPEG-allogeneic cells does not induce inflammation.

| Tissue | Th17 | | |
|---|---|---|---|
| | NOD | Allogeneic | mPEG Allogeneic |
| Blood | 0.38 | 0.67 | 0.17* |
| Spleen | 0.10 ± 0.01 | 2.32 ± 0.38 | 0.11 ± 0.01* |
| Brachial L. Node | 0.08 ± 0.01 | 1.25 ± 0.35 | 0.06 ± 0.01* |
| Pancreatic L. Node | 0.05 ± 0.01 | 0.27 ± 0.08 | 0.07 ± 0.01* |

*p < 0.001 relative to unmodified allogeneic cell treated.

Example IV—POZ Polymer for Inducing Tolerance or Anergy

Some of the material and methods referred to in this example are provided in Example I.

Human PBMC and Dendritic Cell Preparation.

Human whole blood was collected in heparinized vacutainer blood collection tubes (BD, Franklin Lakes, N.J.) from healthy volunteer donors following informed consent. PBMC were isolated from diluted whole blood using FicollePaque PREMIUM™ (GE Healthcare Bio-Sciences Corp, Piscataway, N.J.) as per the product instructions. The PBMC layer was washed twice with 1× Hank's Balanced Salt Solution (HBSS; without $CaCl_2$ and $MgSO_4$; Invitrogen by Life Technologies, Carlsbad, Calif.) and resuspended in the appropriate media as needed for mixed lymphocyte reactions and flow cytometric analysis of Treg and Th17 phenotypes. Dendritic cells (DC) were prepared from isolated PBMC as described by O'Neill and Bhardwaj (O'Neill et al., 2005). Briefly, freshly isolated PBMC were overlaid on Petri dishes for 3 h of in AIM V serum free culture medium (Invitrogen, Carlsbad, Calif.). Non-adherent cells were gently washed off the plate. The adherent cells (monocyte rich cells) were treated with IL-4 and GM-CSF (50 and 100 ng/mL respectively; R&D Systems, Minneapolis, Minn.) in AIM V medium. Cells were again treated with IL-4 and GM-CSF on days 2 and 5. On day 6, cells were centrifuged and resuspended in fresh media supplemented with DC maturation factors (TNF-α, IL-1b, IL-6; R&D Systems, Minneapolis, Minn.) and prostaglandin E2 (Sigma-Aldrich, St. Louis, Mo.). The mature DC-like cells were harvested on day 7 and CD80, CD83, CD86 and HLA-DR expressions were determined to confirm DC maturation via flow cytometry (FACSCalibur™ Flow Cytometer, BD Biosciences, San Jose, Calif.).

mPEG Modification (PEGylation) of PBMCs and Splenocytes.

Human PBMC and murine splenocytes were derivitized using methoxypoly(-ethylene glycol) succinimidyl valerate (mPEG-SVA; Laysan Bio Inc. Arab, Ala.) with a molecular weight of 20 kDa as described in Example I. Grafting concentrations ranged from 0 to 3.0 mM per $4\times10^6$ cells/mL.

POZ Modification (POZylation) of PBMCs and Splenocytes.

N-hydoxysuccinimidyl ester of polyethyloxazoline propionic acid (SPA-PEOZ; Serina Therapeutics, Huntsville, Ala.) with a molecular weight of 20 kDa were grafted on the cells as described in Example I. Grafting concentrations ranged from 0 to 3.0 mM per $4\times10^6$ cells/mL.

In Vitro and In Vivo Cell Proliferation.

Cell proliferation (both in vitro and in vivo) was assessed via flow cytometry using the CellTrace™ CFSE (Carboxyfluorescein diacetate, succinimidyl ester) Cell Proliferation Kit (Invitrogen by Life Technologies e Molecular probes, Carlsbad, Calif.) as described in Example I.

Mixed Lymphocyte Reaction (MLR)—Control and Conditioned Media.

The effects of polymer grafting (20 kDa SVAmPEG or 20 kDa POZ) on allorecognition in vitro were assessed using two-way MLR (Murad et al, 1999A; Chen et al., 2003; Chen et al., 2006) as described in Example I.

Figure 12:
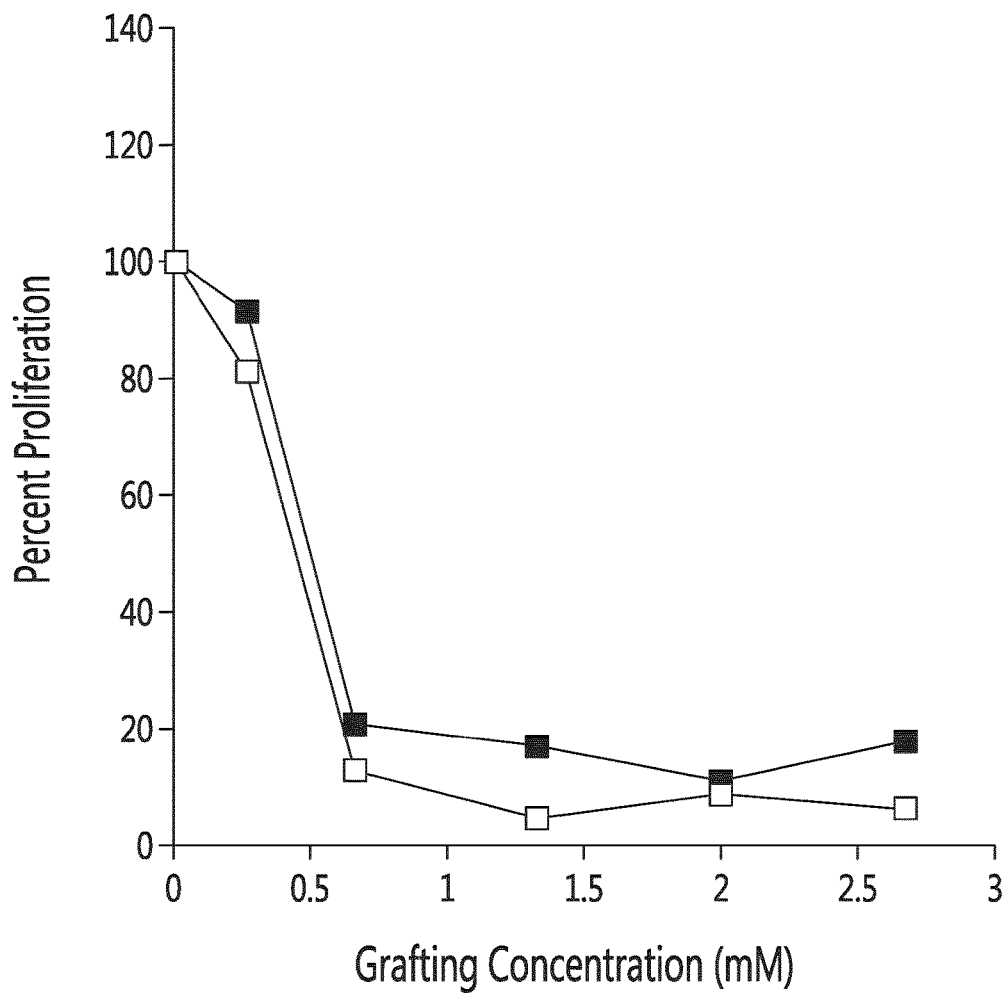
FIG. 12 illustrates cellular proliferation in a 2-way MLR of PEGylated or POZylated cells at day 10. Results are shown for the mPEG-MLR (■) and POZ-MRL (□) as a percentage of proliferation (with respect to the proliferation of the control MLR; i.e., 0 mM) as a function of grafting density.

A 2-way MLR was conducted using either PEGylated or POZylated human cells. As shown on FIG. 12, the grafting of equimolar concentrations of wither 20 kDa mPEG or PEOZ (POZ) on a human mixed lymphocyte reaction (MLR) had similar effects on cellular proliferation.

V—In Vivo Modulation of TREG:Th17 Ratio by Polymer-Modified Lymphocytes

Some of the material and methods referred to in this example are provided in Example I.

Figure 13:
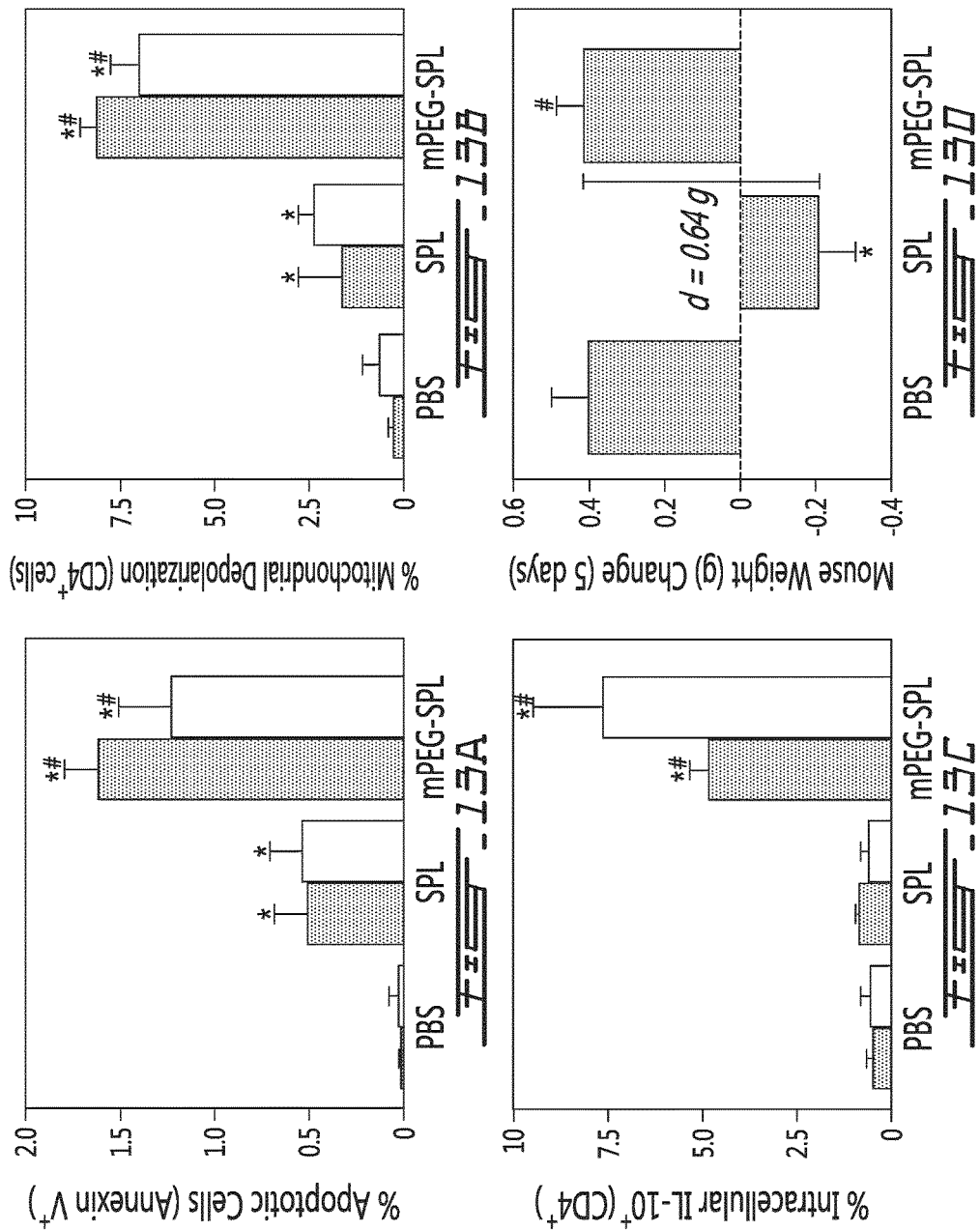
FIG. 13 illustrates the immunomodulatory effects of allogeneic and mPEG-allogeneic splenocytes upon injection in mice. Carrier (PBS), allogeneic splenocytes (SPL) or mPEG allogeneic splenocytes (mPEG-SPL) were injected in mice. (A) In vivo apoptosis is provided as percentage of apoptotic cells (e.g., Annexin V-positive cells) in in the spleen (grey bars) or the lymph node (white bars) in function of type of injection (PBS=control, SPL=unmodified allogeneic splenocytes, mPEG-SPL=mPEG allogeneic splenocytes). (B) Percentage of CD4-positive cells having a depolarized mitochondria in the spleen (grey bars) or the lymph node (white bars) in function of type of injection (PBS=control, SPL=unmodified allogeneic splenocytes, mPEG-SPL=mPEG allogeneic splenocytes). (C) Percentage of intracellular IL-10-positive and CD4-positive cells in the spleen (grey bars) or the lymph node (white bars) in function of type of injection (PBS=control, SPL=unmodified allogeneic splenocytes, mPEG-SPL=mPEG allogeneic splenocytes). (D) 5-day weight gain (g) in mouse in function of type of injection (PBS=control, SPL=unmodifiedallogeneic splenocytes, mPEG-SPL=mPEG allogeneic splenocytes). In (D), the SPL treated mice showed a loss of weight relative to PBS of mPEG-SPL treated mice (0.64 g; approximately a 4% decrease in relative body weight). *=$p<0.01$ relative to PBS treated animal; #=$p<0.01$ relative to unmodified splenocytes.

Non-modified allogeneic splenocytes ($20\times10^6$) and mPEG-modified allogeneic splenocytes ($20\times10^6$) have been intravenously administered to mouse (naïve 8-week old Balb/c mouse; 10 mice per treatment condition). After 5 days, the spleen and the lymph nodes were harvested and the CD4-positive cells they contained were further analyzed by flow cytometry. As shown in FIGS. 13A (annexin V staining) and 13B (mitochondrial depolarization), the administration of mPEG-modified allogeneic splenocytes, when compared to the administration of non-modified allogeneic splenocytes, increased the number of apoptotic CD4-positive cells. As shown in FIG. 13C, the administration of mPEG-modified allogeneic splenocytes, when compared to non-modified allogeneic splenocytes, also increased the intracellular expression of IL-10 in CD4-positive cells. Further, the administration of non-modified allogeneic splenocytes caused a mean decrease in mouse weight whereas the administration of mPEG-modified allogeneic splenocytes caused a mean increase in mouse weight (FIG. 13D).

Figure 14:
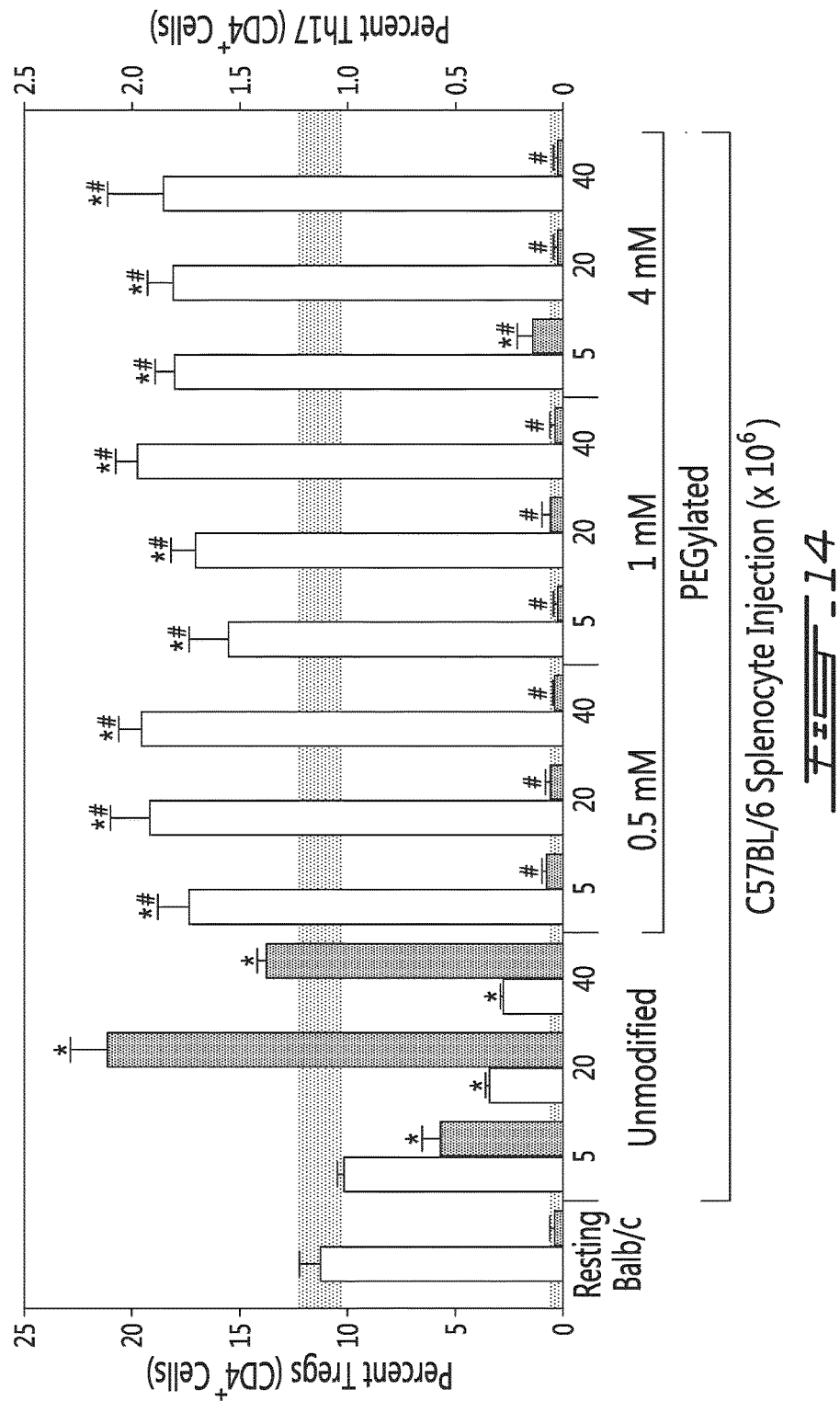
FIG. 14 illustrates the effects of allogeneic splenocytes numbers and grafting density on T cell differentiation in vivo. Percentage of CD4-positive Tregs (white bars, percentage indicated on left y-axis) and Th17 cells (grey bars, percentage indicated on right y-axis) measured in resting Balb/c mice, mice having received unmodified allogeneic (e.g. C57BL/6) splenocytes (5, 20 or $40 \times 10^6$ cells) or mice having received mPEG-modified (at a density of 0.5 mM, 1 mM or 4 mM) allogeneic (e.g. C57BL/6) splenocytes (5, 20 or $40 \times 10^6$ cells). *=$p<0.01$ relative to naive animal; #=$p<0.01$ relative to animal administered unmodified splenocytes.

Non-modified allogeneic splenocytes (either 5, 20 or $40\times10^6$ C57BL/6 cells) and mPEG-modified allogeneic splenocytes (either 5, 20 or $40\times10^6$ C57BL/6 cells grafted at a density of 0.5 mM, 1 mM or 4 mM) have been intravenously administered to mouse (5 Balb/c mice/treatment condition). After 5 days, the spleen and the lymph nodes were harvested and the CD4-positive cells they contained were further analyzed by flow cytometry. As shown in FIG. 14, the administration of mPEG-modified allogeneic splenocytes increased the percentage of Treg cells and decreased the percentage of Th17 cells. As also shown in FIG. 14, the administration of non-modified allogeneic splenocytes decreased the percentage of Treg cells and increased the percentage of Th17 cells. Surprisingly, the increase in Treg cell counts observed after the administration of mPEG-modified allogeneic splenocytes occurred without an increase in spleen weight while the increase in Th17 cell counts observed after the administration of the non-modified allogeneic splenocytes correlated with an increase in spleen weight (a mean 1.5× increase, data not shown).

Figure 15A:
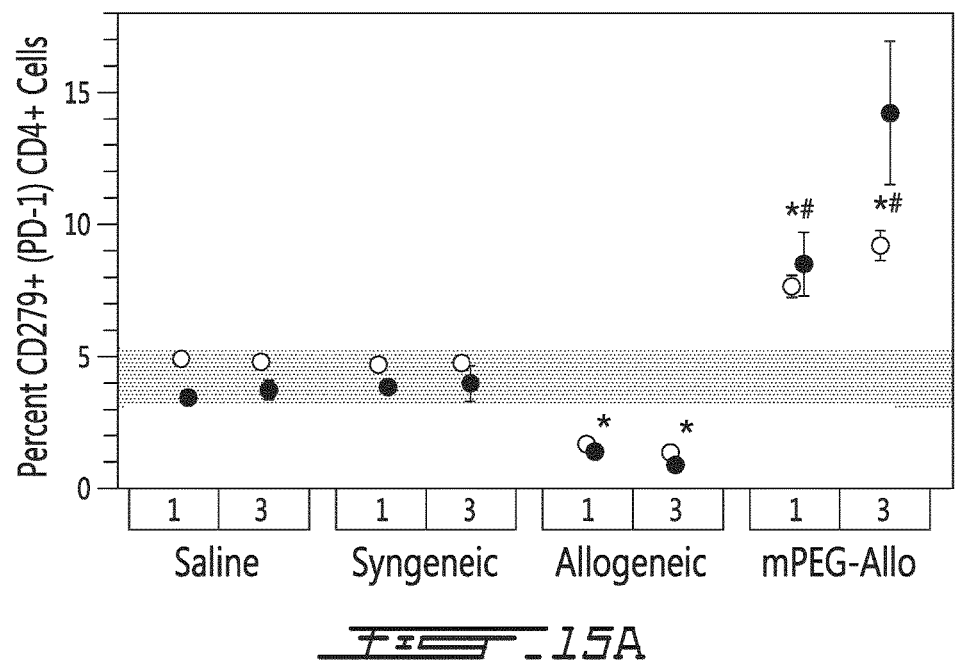
FIG. 15 illustrates the effects of allogeneic splenocytes on CD279 expression of CD4-positive cells in vivo. Saline, syngeneic splenocytes (syngeneic), allogeneic splenocytes (allogeneic) or mPEG-allogeneic splenocytes (mPEG-Allo) have been injected intravenously once (at day 0) or trice (at days 0, 2 and 5) in recipient mice. CD4-positive cells have been harvested 5 (○) or 10 (●) days after the last injection. The percentage of CD4-positive and CD279-positive cells is shown in function of type of injection (saline, syngeneic splenocytes, allogeneic splenocytes or mPEG-allogeneic splenocytes) and number of injections (once=1, trice=3). (A) Results are shown for CD4-positive spleen cells. (B) Results are shown for CD4-positive lymph node cells. *=$p<0.01$ relative to naïve (shaded area) animal; #=$p<0.01$ relative to animal administered unmodified allogneic splenocytes.
Figure 15B:
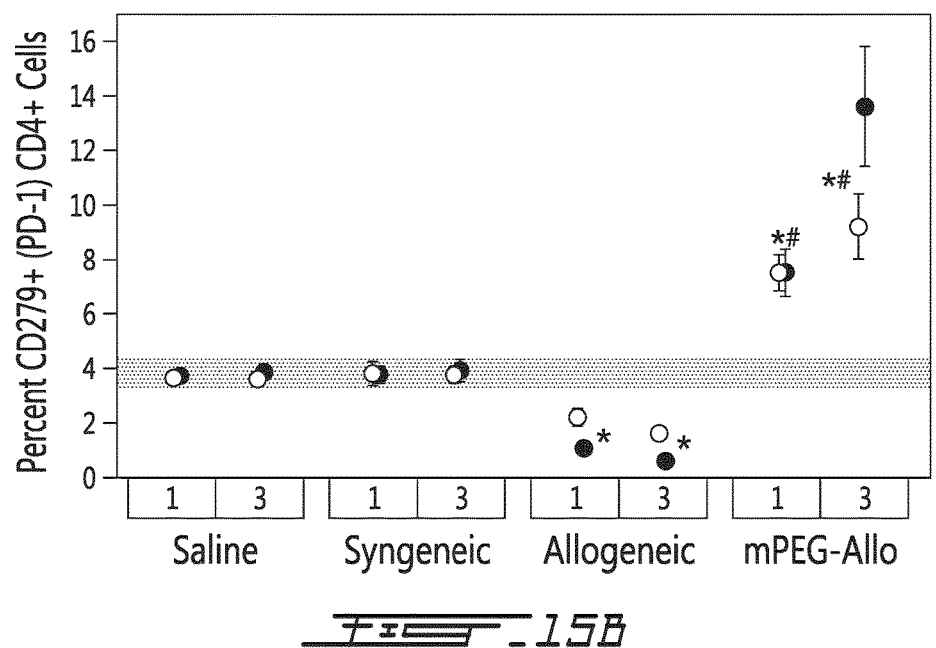
Figure 16:
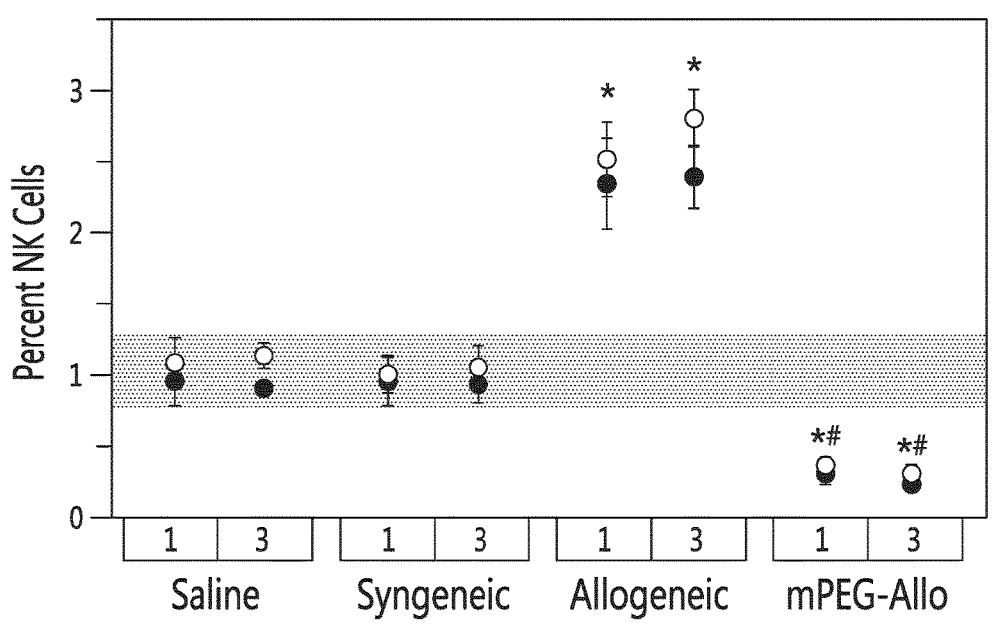
FIG. 16 illustrates the effects of allogeneic splenocytes on the percentage of Natural Killer (NK) cells in vivo. Saline, syngeneic splenocytes (syngeneic), allogeneic splenocytes (allogeneic) or mPEG-allogeneic splenocytes (mPEG-Allo) have been injected intravenously once (at day 0) or trice (at days 0, 2 and 5) in recipient mice. NK cells have been harvested 10 days after the last injection. The percentage of NK cells is shown in function of type of injection (saline, syngeneic splenocytes, allogeneic splenocytes or mPEG-allogeneic splenocytes), number of injections (once=1, trice=3) and location of the NK cells (●=spleen, ○=brachial lymph node). Shaded area refers to the percentage of NK levels in non-treated animals. *=$p<0.01$ relative to naïve (shaded bar) animal; #=$p<0.01$ relative to animal administered unmodified allogneic splenocytes.

Saline, syngeneic splenocytes, non-modified allogeneic splenocytes ($20\times10^6$ C57BL/6 cells) and mPEG-modified allogeneic splenocytes ($20\times10^6$ C57BL/6 cells grafted at a density of 1 mM PEG) have been intravenously administered to mouse either once (at day 0, e.g. condition 1) or thrice (at days 0, 2 and 4, e.g. condition 3) ($20\times10^6$ C57BL/6 cells grafted at a density of 1 mM PEG). After 5 or 10 days, the spleen and lymph nodes were harvested and the CD4-positive cells they contained were further analyzed by flow cytometry with an anti-CD279 antibody. As shown in FIGS. 15A and B, the administration of mPEG-modified allogeneic splenocytes increased the number of CD279-positive cells (with respect to the total number of CD4-positive cells), in the spleen and in the lymph nodes, when compared to mock-treated or syngeneic-treated animals. As also shown in FIGS. 15A and B, the administration of non-modified allogeneic splenocytes decreased the number of CD279-positive cells (with respect to the total number of CD4-positive cells), in the spleen and in the lymph nodes, when compared to mock-treated or syngeneic-treated animals. Ten days after the administration of mPEG-modified allogeneic splenocytes a decrease the percentage of NK cells was observed in both the spleen and the brachial lymph node (FIG. 16). Further, the administration of non-modified allogeneic splenocytes was also shown to increase the percentage of NK cells in both the spleen and the brachial lymph node (FIG. 16). Further, as shown in Table 2 below, the administration of mPEG-allogeneic splenocyte attenuated NK Cell alloresponse and baseline levels in recipient mice (as measured by flow cytometry using a NK1.1 antibody.

TABLE 2

Percentage of NK1.1-positive cells in mice having received saline, syngeneic splenocytes, non-modified allogeneic splenocytes and mPEG-modified allogeneic splenocytes. Cells were harvested 10 days after the last injection

| Type of cells administered ($20 \times 10^6$ cells) | Number of doses | Percentage of NK1.1-positive cells |
|---|---|---|
| None (saline) | 1 | 1.12 |
| None (saline) | 3 | 0.97 |
| Syngeneic | 1 | 0.94 |
| Syngeneic | 3 | 0.91 |
| Non-modified allogeneic | 1 | 2.26 |
| Non-modified allogeneic | 3 | 2.30 |
| mPEG-modified allogeneic | 1 | 0.29 |
| mPEG-modified allogeneic | 3 | 0.21 |

Figure 17A:
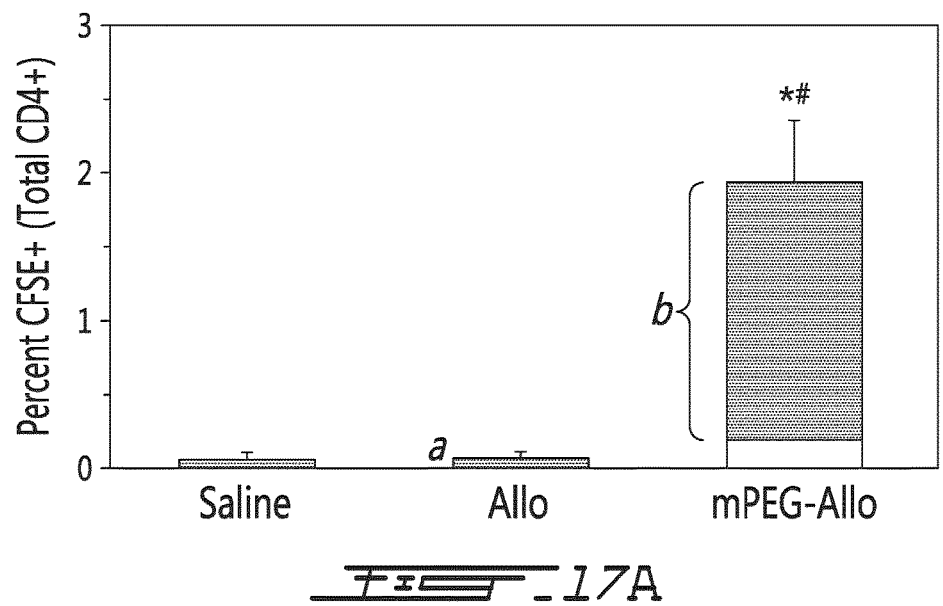
FIG. 17 illustrates the effects of allogeneic splenocytes on the *thymus* in vivo. Saline, allogeneic splenocytes (Allo) or mPEG-allogeneic splenocytes (mPEG-Allo) have been injected intravenously once in recipient mice. Thymic cells have been harvested 5 days after the injection. (A) The percentage of CFSE-positive donor cells (with respect to the total CD4-positive cells) is shown in function of type of injection (saline, allogeneic splenocytes or mPEG-allogeneic splenocytes). White bar in mPEG-Allo sample represents the number of donor Tregs injected. (a) denotes CFSE positive donor cells showing that no thymic microchimerisim is achieved in vivo (i.e., donor cells do not migrate to, or survive in, the recipient *thymus*). (b) denotes the proliferative expansion of the donor Treg yielding thymic microchimerism. * p<0.01 relative to saline treated animal. # p<0.01 relative to allogeneic treated animal. (B) The percentage of Treg cells or CD25-positive cells (with respect to the total CD4-positive cells) is shown in function of type of injection (saline, allogeneic splenocytes or mPEG-allogeneic splenocytes). * p<0.01 relative to saline treated animal. # p<0.01 relative to allogeneic treated animal. (a) denotes decrease in Treg in allogeneic treated animals. (b) denotes increase in Tregs in mPEG-allogeneic treated animals over that of naïve animals. (c) denotes the proliferative expansion of the donor Treg yielding thymic microchimerism. * p<0.01 relative to saline treated animal. # p<0.01 relative to allogeneic treated animal. (C) The percentage of Treg cells (white bars, percentage indicated in left y-axis, with respect to the total CD4-positive cells) and Th17 cells (grey bars, percentage indicated in right y-axis, in view of the total CD4-positive cells) is shown in function of type of injection (saline (naïve), allogeneic splenocytes (Allo), gamma-irradiated allogneneic splenocytes (Ir-Allo), mPEG-allogeneic (mPEG-Allo) or gamma-irradiated allogeneic splenocytes (Ir mPEG-Allo)). Gamma-irradiated donor cells are incapable of proliferation and are non-viable demonstrating that they can also be used to alter the immune response. Changes in T cell subsets in *thymus* are recipient-derived (e.g., CFSE-Negative, data not shown).
Figure 17B:
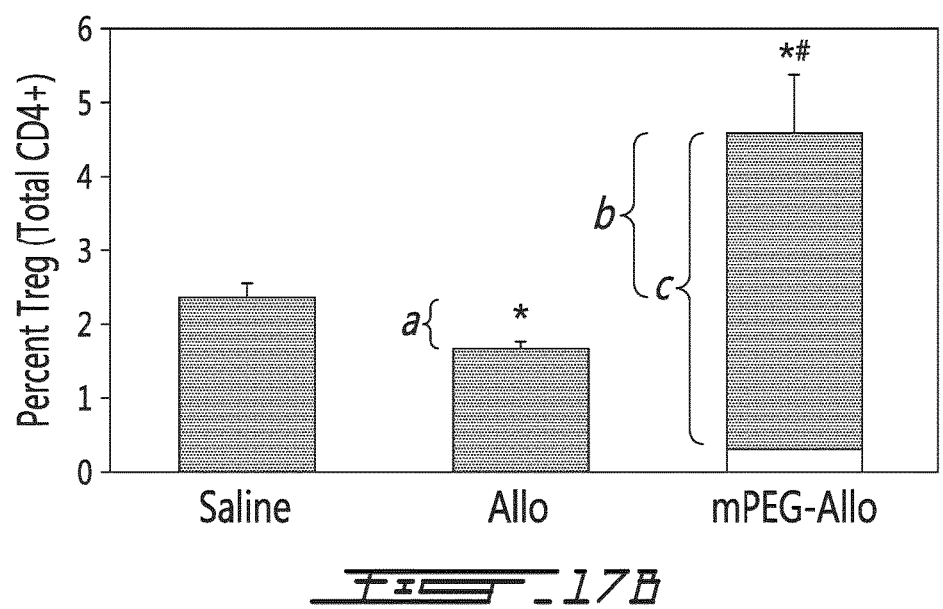
Figure 17C:
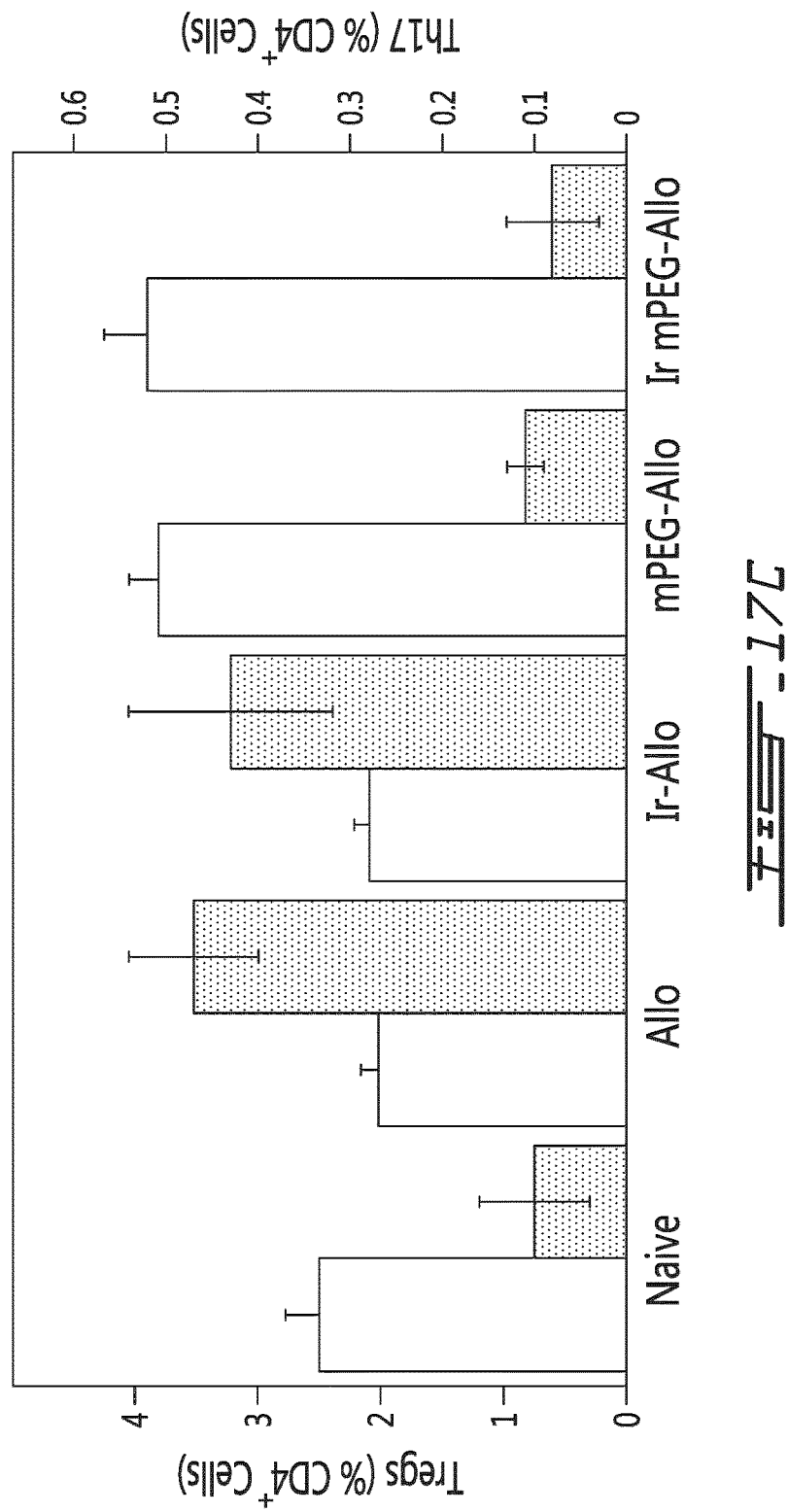

The *thymus* of these animals has also been harvested and the thymic cells characterized. As shown in FIG. 17A, the administration of mPEG-modified allogeneic splenocytes increased microchimerism in the *thymus* of recipient animals as shown by the number of CFSE labeled allogeneic donor cells in the *thymus*. Under normal conditions only 6 to 10% of the injected donor CD4-positive splenocytes are Treg (17A; open bar segment). But as shown in FIG. 17B, the administration of mPEG-modified splenocytes increased the total percentage in thymic Treg cells (donor, open bar; recipient grey bar) in the recipient. In contrast, the administration of non-modified allogeneic splenocytes decreased the in vivo thymic Treg cells. Further, the administration of non-modified allogeneic splenocytes increased the percentage of thymic Th17 cells, while the administration of the mPEG-modified allogeneic splenocytes decreased the percentage of thymic Th17cells (FIG. 17C).

VI—In Vivo Modulation of Treg:Th17 Ratio by Conditioned Media Obtained Via Polymer-Modified Lymphocytes Some of the material and methods referred to in this example are provided in Example I.

Conditioned Serum.

Conditioned serum was obtained (by bleeding the animal and separating the cellular components of blood from the serum via centrifugation) five days after mice (Balb/c; N=5) received saline, unmodified syngeneic splenocytes (Balb/c), unmodified allogeneic splenocytes ($20\times10^6$ C57BL/6 cells) or mPEG-modified allogeneic splenocytes ($20\times10^6$ C57BL/6 cells grafted at a density of 1 mM PEG). The serum from naïve animals was also obtained as a control. The conditioned or naïve serum (100 μl) was then administered (i.v. tail vein injection) once (at day 0) or thrice (at days 0, 2 and 4) to recipient mice (Balb/c; N=5). Five days after the last administration, a blood sample, the spleen and the brachial lymph nodes were obtained from the treated animals and the leukocytes they contained were analyzed.

Figures 18A, 18B:
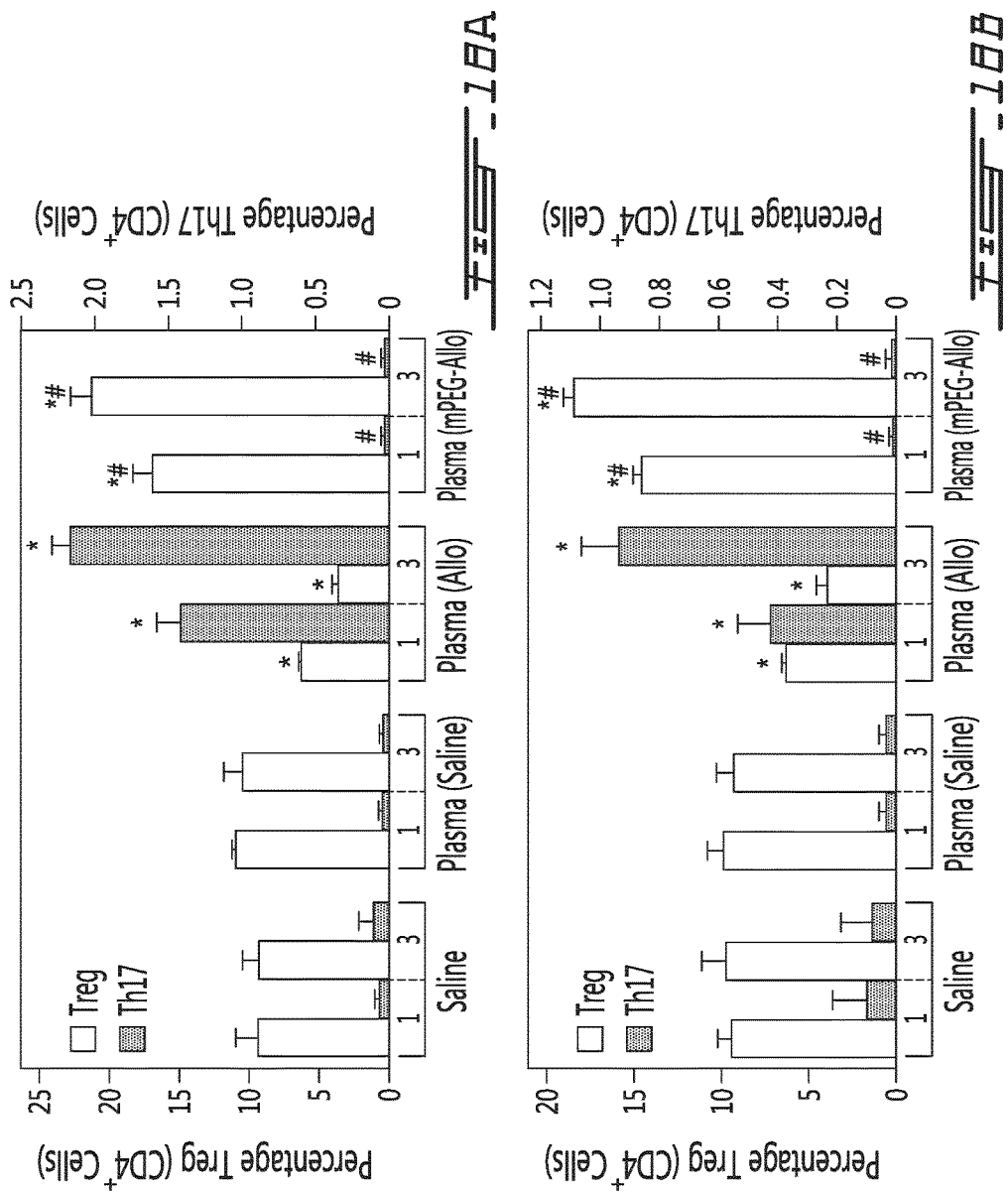
FIG. 18 illustrates that conditioned murine plasma modulates the Treg and Th17 differentiation levels in vivo. Conditioned murine plasma (obtained from donor mice 5 days post leukocyte transfer) was administered once or thrice to mice and Treg/Th17 levels were measured in the spleen and the lymph nodes. (A) Results are shown as the percentage of Treg cells (in function of $CD4^+$ cells) (white bars, left y axis) and as the percentage of Th17 cells (in function of $CD4^+$ cells) (grey bars, right y axis) in the spleen of animals treated once (1) or thrice (3) with a control (Saline), a negative control conditioned plasma from animals having received saline (Plasma (Saline)), a conditioned plasma from animals having received unmodified allogeneic splenocytes (Plasma (Allo)) or a condition plasma from animals having received polymer-modified allogeneic splenocytes (Plasma (mPEG-Allo)). (B) Results are shown as the percentage of Treg cells (in function of $CD4^+$ cells) (white bars, left y axis) and as the percentage of Th17 cells (in function of $CD4^+$ cells) (grey bars, right y axis) in the brachial lymph nodes of animals treated once (1) or thrice (3) with a control (Saline), a negative control conditioned plasma from animals having received saline (Plasma (Saline)), a conditioned plasma from animals having received unmodified allogeneic splenocytes (Plasma (Allo)) or a conditioned plasma from animals having received polymer-modified allogeneic splenocytes (Plasma (mPEG-Allo)). *=p<0.01 relative to saline control animal; #=p<0.01 relative to animal administered with the unmodified allogeneic splenocytes (Plasma (Allo)).

As shown on FIG. 18, the administration of the conditioned serum from animals having received unmodified allogeneic splenocytes caused in vivo a reduction in the levels of Tregs, while increasing the levels of Th17 cells in both the spleen and the lymph nodes. As also shown on FIG. 18, the administration of the conditioned serum from animals having received polymer modified allogeneic splenocytes caused in vivo an increase in the levels of Tregs as well as a decrease in the levels of Th17 cells, both in the spleen and the lymph node.

Figure 19:
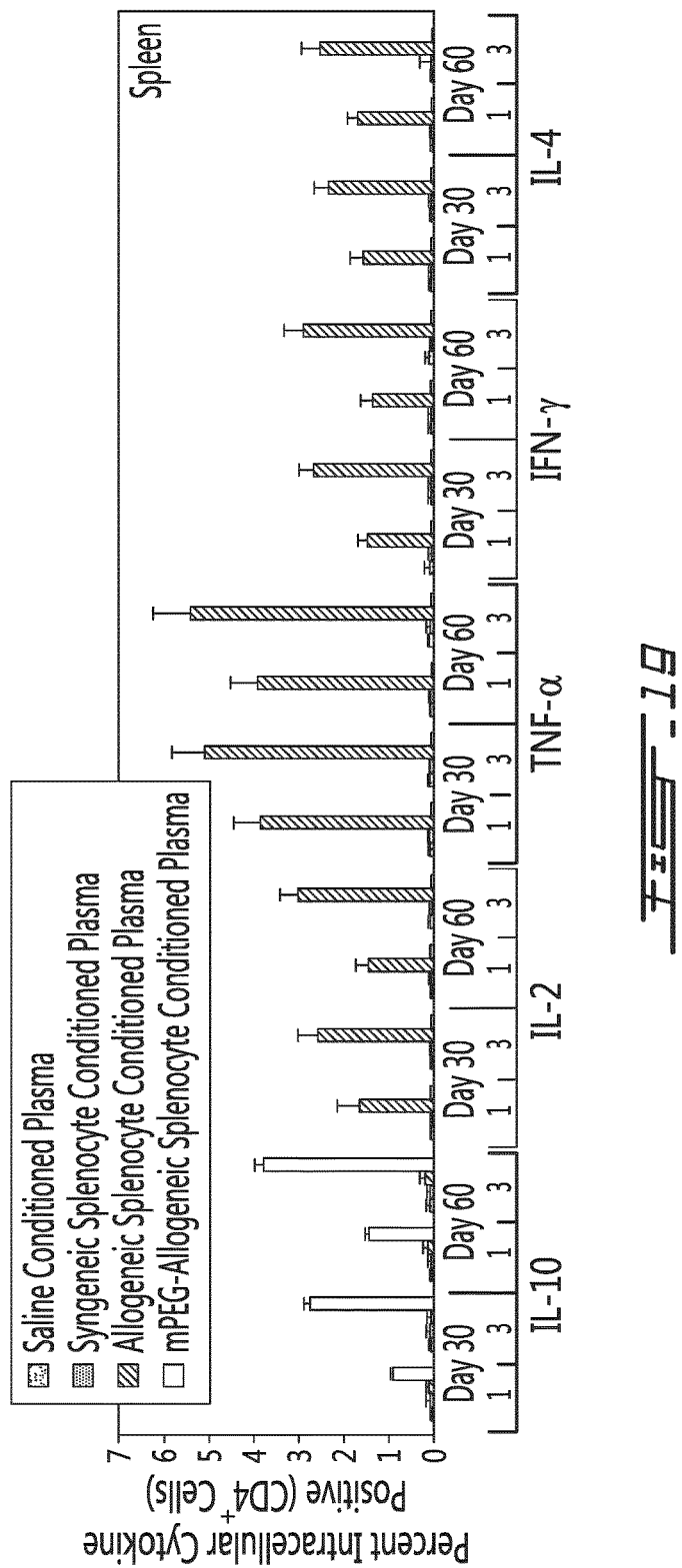
FIG. 19 illustrates that conditioned murine plasma induces long-term changes in cytokines expression levels in vivo. Conditioned murine plasma (obtained from donor mice 5 days post leukocyte transfer) was administered once or thrice to mice and intracellular cytokine positive cells were measured in the spleen and the lymph nodes. Results are shown as the percentage of intracellular cytokine positive cells (in function of $CD4^+$ cells) in the spleen of animals treated once (1) or thrice (3) with a negative conditioned plasma from animals having received saline (light grey bars), a conditioned plasma from animals having received unmodified syngeneic splenocytes (dark gray bars), a conditioned plasma from animals having received unmodified allogeneic splenocytes (hatched bars) and a conditioned plasma from animals having received polymer-modified allogeneic splenocytes (white bars). Results are shown for IL-10, IL-2, TNF-α, IFN-γ and IL-4 either 30 or 60 days following the last administration of the conditioned serum or control. Similar results have been obtained with the leukocytes obtained from the brachial lymph nodes of these treated animals (data not shown).

This modulation in Treg/Th17 ratio was also shown to be associated in the long term modification of the expression of pro-/anti-inflammatory cytokine positive CD4+ lymphocytes. As shown on FIG. 19, the administration of the conditioned serum from animals having received unmodified allogeneic splenocytes caused in vivo an increase in the expression of pro-inflammatory cytokines (IL-2, TNF-α, IFN-γ and IL-4) positive lymphocytes while the administration of the conditioned serum from animals having received polymer modified allogeneic splenocytes caused in vivo an increase in the expression of anti-inflammatory cytokines (IL-10) in CD4+ lymphocytes. These results were observed for at least 30 days and 60 days after the last administration. Similar observations have been observed 270 days after the last administration (data not shown).

Figure 20:
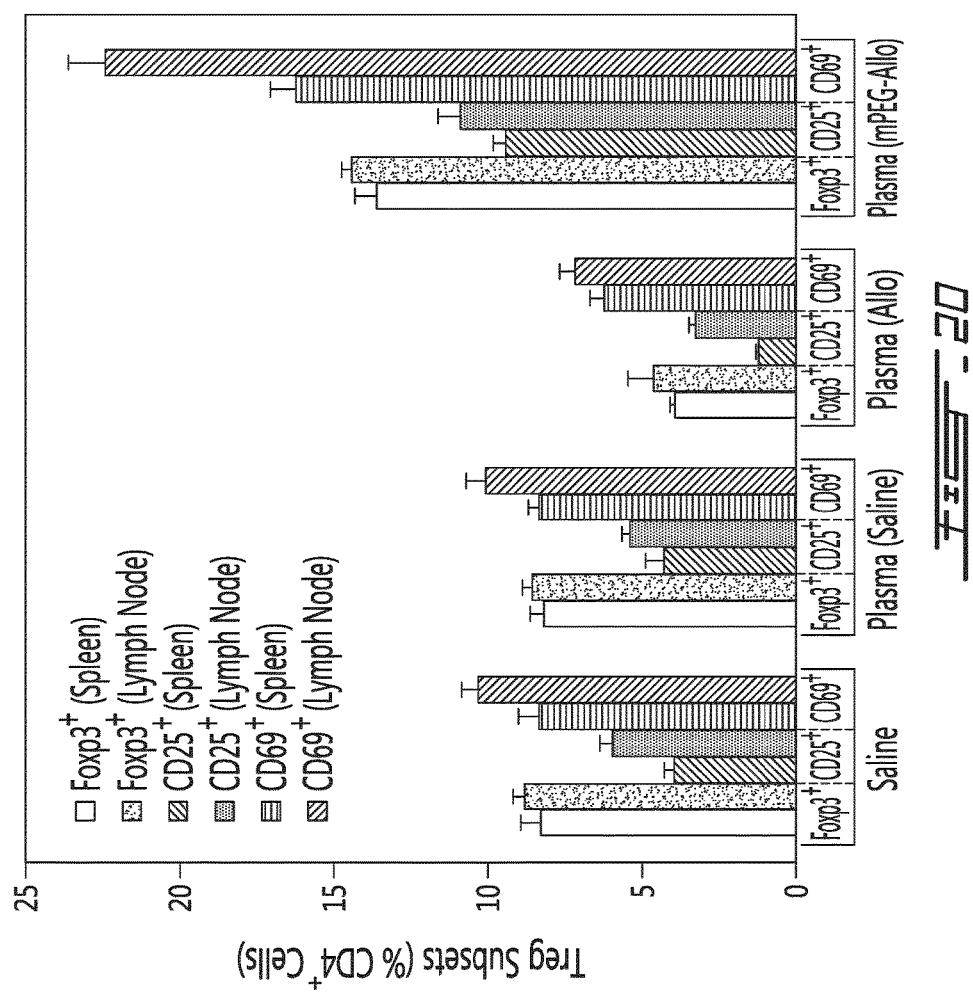
FIG. 20 illustrates that conditioned murine plasma modulates multiple Treg subsets in vivo. Conditioned murine plasma (obtained from donor mice 5 days post allogeneic leukocyte transfer) was administered mice and multiple Treg subset levels were measured in the spleen and the lymph nodes. Results are shown as the percentage of Treg subset (in function of $CD4^+$ cells) in the spleen and brachial lymph node of animals administered with a control (Saline), a negative control conditioned plasma from animals having received saline (Plasma (Saline)), a conditioned plasma from animals having received unmodified allogeneic splenocytes (Plasma (Allo)) or a condition plasma from animals having received polymer-modified allogeneic splenocytes (Plasma (mPEG-Allo)). Results are shown for $Foxp3^+$ cells (white bars in the spleen, light gray bars in the lymph node), $CD25^+$ cells (hatches bars in the spleen, dark grey bars in the lymph node) and $CD69^+$ cells (horizontal hatched bars in the spleen, diagonal hacthed bars in the lymph node).

The administration of the conditioned medium also caused a shift in the Treg subsets. As shown on FIG. 20, the administration of the conditioned serum from animals having received unmodified allogeneic splenocytes caused in vivo decrease in all Treg subsets (Foxp3+, CD25+ and CD69+) in the spleen and the lymph nodes. The administration of the conditioned serum from animals having received polymer modified allogeneic splenocytes caused in vivo an increase all Treg subsets. Surprisingly CD69+ Treg cells demonstrated the most significant increase relative to naïve mice.

As shown on FIG. 21, the administration of the conditioned serum from animals having received unmodified allogeneic splenocytes caused in vivo a reduction in the levels of Tregs, while increasing the levels of Th17 cells in the spleen, the lymph nodes and the blood. As also shown on FIG. 21, the administration of the conditioned serum from animals having received polymer modified allogeneic splenocytes caused in vivo an increase in the levels of Tregs as well as a decrease in the levels of Th17 cells, in the spleen, the lymph node and the blood.

REFERENCES

Bradley A J, Test S T, Murad K L, Mitsuyoshi J, Scott M D. Interactions of IgM ABO antibodies and complement with methoxy-PEG-modified human RBCS. Transfusion 2001; 41:1225-33.

Bradley A J, Scott M D. Immune complex binding by immunocamouflaged [poly(ethylene glycol)-grafted] erythrocytes. Am J Hematol 2007; 82:970-5.

Chen A M, Scott M D. Current and future applications of immunological attenuation via pegylation of cells and tissue. BioDrugs 2001; 15:833-47.

Chen A M, Scott M D. Immunocamouflage: prevention of transfusion-induced graft-versus-host disease via polymer grafting of donor cells. J Biomed Mater Res A 2003; 67:626-36.

Chen A M, Scott M D. Comparative analysis of polymer and linker chemistries on the efficacy of immunocamouflage of murine leukocytes. Artif Cells Blood Substit Immobil Biotechnol 2006; 34:305-22.

Le Y, Scott M D. Immunocamouflage: the biophysical basis of immunoprotection by grafted methoxypoly(ethylene glycol) [mpeg]. Acta Biomater 2010; 6:2631-41.

McCoy L L, Scott M D. Broad spectrum antiviral prophylaxis: inhibition of viral infection by polymer grafting with methoxypoly(ethylene glycol). In: PF T, editor. Antiviral drug discovery for emerging diseases and bioterrorism threats. Hoboken, N.J.: Wiley & Sons; 2005. p. 379-95.

Murad K L, Gosselin E J, Eaton J W, Scott M D. Stealth cells: prevention of major histocompatibility complex class II-mediated T-cell activation by cell surface modification. Blood 1999A; 94:2135-41.

Murad K L, Mahany K L, Brugnara C, Kuypers F A, Eaton J W, Scott M D. Structural and functional consequences of antigenic modulation of red blood cells with methoxypoly (ethylene glycol). Blood 1999B; 93:2121-7.

O'Neill D W, Bhardwaj N. Differentiation of peripheral blood monocytes into dendritic cells. Curr Protoc Immunol; 2005. Chapter 22: Unit 22F.4.

Scott M D, Murad K L, Koumpouras F, Talbot M, Eaton J W. Chemical camouflage of antigenic determinants: stealth erythrocytes. Proc Natl Acad Sci USA 1997; 94:7566-71.

Sutton T C, Scott M D. The effect of grafted methoxypoly (ethylene glycol) chain length on the inhibition of respiratory syncytial virus (RSV) infection and proliferation. Biomaterials 2010; 31:4223-30.

Wang D, Toyofuku W M, Chen A M, Scott M D. Induction of immunotolerance via mPEG grafting to allogeneic leukocytes. Biomaterials. 2011 December; 32(35):9494-503.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of increasing a ratio of the level of endogenous regulatory T (Treg) cells to the level of endogenous pro-inflammatory T cells in a subject in need thereof for treating or alleviating the symptoms associated with an auto-immune disease afflicting the subject, said method comprising administering to the subject a therapeutic amount of:

a first cellular preparation comprising a first leukocyte having a cytoplasmic membrane associated to a low-immunogenic biocompatible polymer, wherein the low-immunogenic biocompatible polymer is covalently associated with the first leukocyte, and wherein the first leukocyte is allogeneic to the subject and is irradiated;

wherein the low-immunogenic biocompatible polymer is polyethylene glycol (PEG), or 2-alkyloxazoline (POZ), or hyperbranched polyglycerol (HPG);

thereby increasing the ratio of the level of Treg cells to the level of pro-inflammatory T cells in the subject for treating or alleviating the symptoms associated with an auto-immune disease afflicting the subject.

2. The method of claim 1, wherein the first leukocyte is a T cell.

3. The method of claim 2, wherein the T cell is a CD4-positive T cell or a CD8-positive T cell.

4. The method of claim 1, wherein the auto-immune disease is at least one of type I diabetes, rheumatoid arthritis, multiple sclerosis, psoriasis, lupus, immune thrombocytopenia, experimental autoimmune encephalomyelitis, autoimmune uveitis, inflammatory bowel disease, scleroderma and Crohn's disease.

5. The method of claim 1, wherein the low-immunogenic biocompatible polymer is polyethylene glycol (PEG).

6. The method of claim 1, wherein the first leukocyte is a peripheral blood mononuclear cell.

7. The method of claim 1, wherein the first leukocyte is a splenocyte.

8. A method of increasing a ratio of the level of endogenous regulatory T (Treg) cells to the level of endogenous pro-inflammatory T cells in a subject in need thereof for treating or alleviating the symptoms associated with an auto-immune disease afflicting the subject, said method comprising:

(i) providing a first leukocyte having a cytoplasmic membrane associated to a low-immunogenic biocompatible polymer, wherein the first leukocyte is allogeneic to the subject;

(ii) culturing the first leukocyte with a leukocyte population comprising T cells from the subject to provide a cultured cellular preparation, wherein the cultured cellular preparation comprises cultured T cells autologous to the subject; and (iii) administering to the subject a therapeutic amount of the cultured T cells autologous to the subject;

wherein the low-immunogenic biocompatible polymer is polyethylene glycol (PEG), or 2-alkyloxazoline (POZ), or hyperbranched polyglycerol (HPG);

thereby increasing the ratio of the level of Treg cells to the level of pro-inflammatory T cells in the subject for treating or alleviating the symptoms associated with an auto-immune disease afflicting the subject.

9. The method of claim 8, wherein the first leukocyte is a T cell.

10. The method of claim 9, wherein the T cell is a CD4-positive T cell or a CD8-positive T cell.

11. The method of claim 8, further comprising expanding the leukocyte population from the subject in vitro prior to step (ii).

12. The method of claim 8, wherein the auto-immune disease is at least one of type I diabetes, rheumatoid arthritis, multiple sclerosis, psoriasis, lupus, immune thrombocytopenia, experimental autoimmune encephalomyelitis, autoimmune uveitis, inflammatory bowel disease, scleroderma and Crohn's disease.

13. The method of claim 8, wherein the low-immunogenic biocompatible polymer is polyethylene glycol (PEG).

14. The method of claim 8, wherein the first leukocyte is or the leukocyte population from a subject comprises a peripheral blood mononuclear cell.

15. The method of claim 8, wherein the first leukocyte is or the leukocyte population from the subject comprises a splenocyte.

16. A method of increasing a ratio of the level of endogenous regulatory T (Treg) cells to the level of endogenous pro-inflammatory T cells in a subject in need thereof for treating or alleviating the symptoms associated with an auto-immune disease afflicting the subject, said method comprising:

(i) providing a first leukocyte having a cytoplasmic membrane associated to a low-immunogenic biocompatible polymer, wherein the first leukocyte is allogeneic to the subject;

(ii) culturing the first leukocyte with a T cell from the subject to provide a cultured cellular preparation, wherein the cultured cellular preparation comprises cultured T cells autologous to the subject; and (iii) administering to the subject a therapeutic amount of the cultured T cells autologous to the subject;

wherein the low-immunogenic biocompatible polymer is polyethylene glycol (PEG), or 2-alkyloxazoline (POZ), or hyperbranched polyglycerol (HPG);

thereby increasing the ratio of the level of Treg cells to the level of pro-inflammatory T cells in the subject for treating or alleviating the symptoms associated with an auto-immune disease afflicting the subject.

17. The method of claim 16, wherein the first leukocyte is a first T cell.

18. The method of claim 17, wherein the first T cell is a CD4-positive T cell or a CD8-positive T cell.

19. The method of claim 16, further comprising expanding the T cell from the subject in vitro prior to step (ii).

20. The method of claim 16, wherein the auto-immune disease is at least one of type I diabetes, rheumatoid arthritis, multiple sclerosis, psoriasis, lupus, immune thrombocytopenia, experimental autoimmune encephalomyelitis, autoimmune uveitis, inflammatory bowel disease, scleroderma and Crohn's disease.

21. The method of claim 16, wherein the low-immunogenic biocompatible polymer is polyethylene glycol (PEG).

22. The method of claim 16, wherein the first leukocyte is a peripheral blood mononuclear cell.

23. The method of claim 16, wherein the first leukocyte is a splenocyte.

* * * * *